US009982046B2

(12) United States Patent
Heldwein et al.

(10) Patent No.: US 9,982,046 B2
(45) Date of Patent: May 29, 2018

(54) METHODS OF TREATING CARDIOVASCULAR DISORDERS WITH LECTIN-LIKE OXIDIZED LDL RECEPTOR 1 ANTIBODIES

(71) Applicant: NOVARTIS AG, Basel (CH)

(72) Inventors: Kurt Alex Heldwein, Belmont, MA (US); Igor Splawski, Winchester, MA (US); Jennifer Brogdon, Sudbury, MA (US); Joshua Goldstein, San Diego, CA (US); William Dole, Ipswich, MA (US); John Trauger, Cambridge, MA (US); Chonghui Zhang, Brookline, MA (US)

(73) Assignee: NOVARTIS AG, Basel (CH)

( * ) Notice: Subject to any disclaimer, the term of this patent is extended or adjusted under 35 U.S.C. 154(b) by 0 days. days.

(21) Appl. No.: 15/346,026

(22) Filed: Nov. 8, 2016

(65) Prior Publication Data

US 2017/0152313 A1 Jun. 1, 2017

Related U.S. Application Data

(62) Division of application No. 14/307,515, filed on Jun. 18, 2014, now Pat. No. 9,512,222.

(60) Provisional application No. 61/837,776, filed on Jun. 21, 2013.

(51) Int. Cl.

| | |
|---|---|
| ***A61P 9/08*** | (2006.01) |
| ***A61P 9/04*** | (2006.01) |
| ***A61P 9/10*** | (2006.01) |
| ***A61P 9/12*** | (2006.01) |
| ***A61K 39/395*** | (2006.01) |
| ***C07K 16/28*** | (2006.01) |
| ***A61K 9/00*** | (2006.01) |
| ***A61K 45/06*** | (2006.01) |
| *C07K 14/47* | (2006.01) |
| *A61K 39/00* | (2006.01) |

(52) U.S. Cl.

CPC ............ *C07K 16/28* (2013.01); *A61K 9/0019* (2013.01); *A61K 39/3955* (2013.01); *A61K 45/06* (2013.01); *A61P 9/04* (2018.01); *A61P 9/08* (2018.01); *A61P 9/10* (2018.01); *A61P 9/12* (2018.01); *C07K 16/2851* (2013.01); *A61K 2039/505* (2013.01); *C07K 14/4726* (2013.01); *C07K 2317/21* (2013.01); *C07K 2317/24* (2013.01); *C07K 2317/33* (2013.01); *C07K 2317/34* (2013.01); *C07K 2317/565* (2013.01); *C07K 2317/76* (2013.01); *C07K 2317/92* (2013.01)

(58) Field of Classification Search

None

See application file for complete search history.

(56) References Cited

U.S. PATENT DOCUMENTS

| | | | |
|---|---|---|---|
| 6,197,937 | B1 | 3/2001 | Sawamura et al. |
| 7,993,643 | B2 | 8/2011 | Kobayashi et al. |
| 8,481,314 | B2 | 7/2013 | Banchereau et al. |
| 9,339,556 | B2 | 5/2016 | Banchereau et al. |
| 9,512,222 | B2 | 12/2016 | Heldwein et al. |
| 9,562,101 | B2 | 2/2017 | Heldwein et al. |
| 2003/0143226 | A1 | 7/2003 | Kobayashi et al. |
| 2008/0152657 | A1 | 6/2008 | Horowitz et al. |
| 2008/0267984 | A1 | 10/2008 | Banchereau et al. |
| 2009/0311270 | A1 | 12/2009 | Allen et al. |
| 2012/0087926 | A1 | 4/2012 | Matsuda et al. |
| 2014/0120617 | A1 | 5/2014 | Banchereau et al. |
| 2014/0377281 | A1 | 12/2014 | Heldwein et al. |
| 2015/0004168 | A1 | 1/2015 | Heldwein et al. |
| 2015/0150945 | A1 | 6/2015 | Francois et al. |
| 2016/0024593 | A1 | 1/2016 | Zheng et al. |
| 2017/0015744 | A1 | 1/2017 | Sawamura et al. |
| 2017/0260272 | A1 | 9/2017 | Heldwein et al. |

FOREIGN PATENT DOCUMENTS

| | | | |
|---|---|---|---|
| EP | 1418234 | A1 | 5/2004 |
| EP | 2048161 | A1 | 4/2009 |
| EP | 2444492 | A1 | 4/2012 |
| EP | 2444492 | A9 | 7/2012 |
| JP | 2000109435 | A | 4/2000 |
| JP | 4497586 | B2 | 7/2010 |
| JP | 2010180212 | A | 8/2010 |
| JP | 2012100585 | A | 5/2012 |
| JP | 5232818 | B2 | 7/2013 |
| JP | 5706669 | B2 | 4/2015 |
| JP | 2015127309 | | 7/2015 |
| WO | 2008103953 | A2 | 8/2008 |
| WO | 2010147171 | A1 | 12/2010 |
| WO | 2012009709 | A1 | 1/2012 |
| WO | 2013063095 | A1 | 5/2013 |
| WO | 2014039840 | A1 | 3/2014 |
| WO | 2014144666 | A2 | 9/2014 |

(Continued)

OTHER PUBLICATIONS

Mehta et al, 2011. Cardiovasc Drugs Ther. 25:495-500.*

Francone, et al., "The hydrophobic tunnel present in LOX-1 is essential for oxidized LDL recognition and binding", Journal of Lipid Research 50(3):546-555 (2009).

Sakamoto et al, "Role of LOX-1 in Monocyte Adhesion-Triggered Redox, Akt/eNOS and CA2+ Signaling Pathways in Endothelial Cells", Journal of Cellular Physiology, 220:706-715 (2009).

Tickle et al., "High-Throughput Screening for High Affinity Antibodies", JALA, 14:303-307 (2009).

(Continued)

*Primary Examiner* — Zachary Howard

(74) *Attorney, Agent, or Firm* — Sherwin Y. Chan

(57) ABSTRACT

The present invention relates to monoclonal antibodies binding to human lectin-like oxidized LDL (low density lipoprotein) receptor 1 (hereinafter, sometimes referred to as "LOX-1"), and pharmaceutical compositions and methods of treatment comprising the same.

41 Claims, 9 Drawing Sheets

(56) References Cited

FOREIGN PATENT DOCUMENTS

| | | | |
|---|---|---|---|
| WO | 2014205300 | A2 | 12/2014 |
| WO | 2014205302 | A2 | 12/2014 |
| WO | 2015098901 | A1 | 7/2015 |
| WO | 2016050889 | A1 | 4/2016 |

OTHER PUBLICATIONS

Rudikoff et al., "Single amino acid substitution altering antigen-binding specificity", Proc. Natl. Acad. Sci. USA, 79:1979-1983 (1982).
MacCallum et al., "Antibody-antigen Interactions; Contact Analysis and Binding Site Topography", Jounral of Molecular Biology, 262:732-745 (1996).
DePascalis et al., "Grafting of 'Abbreviated' Complemntarity-Determining Regions Containing Specificity-Determining Residues Essential for Ligand Contact to Engineer a Less Immunogenic Humanized Monoclonal Antibody", Journal of Immunology, 169:3076-3084 (2002).
Casset et al., "A peptide mimetic of an anti-CD4 monoclonal antibody by rational design", Biochemical and Biophysical Research Communications, 307:198-205 (2003).
Vajdos et al., "Comprehensive Functional Maps of the Antigen-binding Site of an Anti-ErbB2 Antibody Obtained with Shotgun Scanning Mutagenesis", Journal of Molecular Biology, 320:415-428 (2002).
Holm et al., "Functional mapping and single chain construction of the anti-cytokeratin 8 monoclonal antibody TS1", Molecular Immunology, 44:1075-1084 (2007).
Chen et al., "Selection and Analysis of an Optimized Anti-VEGF Antibody: Crystal Structure of an Affinity-matured Fab in Complex with Antigen", Journal of Molecular Biology, 293:865-881 (1999).
Wu et al., "Humanization of a Murine Monoclonal Antibody by Simultaneous Optimization of Framework and CDR Residues", Journal of Molecular Biology, 294:151-162 (1999).
Brown et al., "Tolerance to Single, but Not Multiple, Amino Acid Replacements in Antibody VH CDR", Journal of Immunology, 156(9):3285-3291 (1996).
Ohki et al., "Crystal Structure of Human Lectin-like, Oxidized Low-Density Lipoprotein Receptor 1 Ligand Binding Domain and Its Ligand Recognition Mode to OxLDL", Structure, 13(6):905-917 (2005).
Wark et al., "Latest technologies for the enhancement of antibody affinity", Adv. Drug Deilv. Rev., 58(5-6):657-70 (2006).
Xu et al., "Anti-LOX-1 rescues endothelial function in coronary arterioles in atherosclerotic ApoE knockout mice", Arterioscler Thromb Vasc Biol. 27(4):871-877 (2007).

* cited by examiner

SEQUENCE LISTING

```
<160> NUMBER OF SEQ ID NOS: 147

<210> SEQ ID NO 1
<211> LENGTH: 273
<212> TYPE: PRT
<213> ORGANISM: Homo sapiens

<400> SEQUENCE: 1

Met Thr Phe Asp Asp Leu Lys Ile Gln Thr Val Lys Asp Gln Pro Asp
1               5                   10                  15

Glu Lys Ser Asn Gly Lys Lys Ala Lys Gly Leu Gln Phe Leu Tyr Ser
            20                  25                  30

Pro Trp Trp Cys Leu Ala Ala Ala Thr Leu Gly Val Leu Cys Leu Gly
        35                  40                  45

Leu Val Val Thr Ile Met Val Leu Gly Met Gln Leu Ser Gln Val Ser
    50                  55                  60

Asp Leu Leu Thr Gln Glu Gln Ala Asn Leu Thr His Gln Lys Lys Lys
65                  70                  75                  80

Leu Glu Gly Gln Ile Ser Ala Arg Gln Gln Ala Glu Glu Ala Ser Gln
                85                  90                  95

Glu Ser Glu Asn Glu Leu Lys Glu Met Ile Glu Thr Leu Ala Arg Lys
            100                 105                 110

Leu Asn Glu Lys Ser Lys Glu Gln Met Glu Leu His His Gln Asn Leu
        115                 120                 125

Asn Leu Gln Glu Thr Leu Lys Arg Val Ala Asn Cys Ser Ala Pro Cys
    130                 135                 140

Pro Gln Asp Trp Ile Trp His Gly Glu Asn Cys Tyr Leu Phe Ser Ser
```

145 150 155 160

Gly Ser Phe Asn Trp Glu Lys Ser Gln Glu Lys Cys Leu Ser Leu Asp
165 170 175

Ala Lys Leu Leu Lys Ile Asn Ser Thr Ala Asp Leu Asp Phe Ile Gln
180 185 190

Gln Ala Ile Ser Tyr Ser Ser Phe Pro Phe Trp Met Gly Leu Ser Arg
195 200 205

Arg Asn Pro Ser Tyr Pro Trp Leu Trp Glu Asp Gly Ser Pro Leu Met
210 215 220

Pro His Leu Phe Arg Val Arg Gly Ala Val Ser Gln Thr Tyr Pro Ser
225 230 235 240

Gly Thr Cys Ala Tyr Ile Gln Arg Gly Ala Val Tyr Ala Glu Asn Cys
245 250 255

Ile Leu Ala Ala Phe Ser Ile Cys Gln Lys Lys Ala Asn Leu Arg Ala
260 265 270

Gln

<210> SEQ ID NO 2
<211> LENGTH: 819
<212> TYPE: DNA
<213> ORGANISM: Homo sapiens

<400> SEQUENCE: 2
atgacttttg atgacctaaa gatccagact gtgaaggacc agcctgatga gaagtcaaat 60
ggaaaaaaag ctaaaggtct tcagtttctt tactctccat ggtggtgcct ggctgctgcg 120
actctagggg tcctttgcct gggattagta gtgaccatta tggtgctggg catgcaatta 180
tcccaggtgt ctgacctcct aacacaagag caagcaaacc taactcacca gaaaaagaaa 240
ctggagggac agatctcagc ccggcaacaa gcagaagaag cttcacagga gtcagaaaac 300
gaactcaagg aaatgataga aacccttgct cggaagctga atgagaaatc caaagagcaa 360
atggaacttc accaccagaa tctgaatctc caagaaacac tgaagagagt agcaaattgt 420
tcagctcctt gtccgcaaga ctggatctgg catggagaaa actgttacct attttcctcg 480
ggctcattta actgggaaaa gagccaagag aagtgcttgt ctttggatgc caagttgctg 540
aaaattaata gcacagctga tctggacttc atccagcaag caatttccta ttccagtttt 600
ccattctgga tggggctgtc tcggaggaac cccagctacc catggctctg ggaggacggt 660
tctcctttga tgccccactt atttagagtc cgaggcgctg tctcccagac atacccttca 720
ggtacctgtg catatataca acgaggagct gtttatgcgg aaaactgcat tttagctgcc 780
ttcagtatat gtcagaagaa ggcaaaccta agagcacag 819

<210> SEQ ID NO 3
<211> LENGTH: 19
<212> TYPE: PRT
<213> ORGANISM: Homo sapiens

<400> SEQUENCE: 3

Phe Arg Val Arg Gly Ala Val Ser Gln Thr Tyr Pro Ser Gly Thr Cys
1 5 10 15

Ala Tyr Ile

<210> SEQ ID NO 4
<211> LENGTH: 10
<212> TYPE: PRT
<213> ORGANISM: Homo sapiens

<400> SEQUENCE: 4

```
Asn Glu Leu Lys Glu Met Ile Glu Thr Leu
1               5                   10
```

<210> SEQ ID NO 5
<211> LENGTH: 12
<212> TYPE: PRT
<213> ORGANISM: Homo sapiens

<400> SEQUENCE: 5

```
Ser Arg Arg Asn Pro Ser Tyr Pro Trp Leu Trp Glu
1               5                   10
```

<210> SEQ ID NO 6
<211> LENGTH: 232
<212> TYPE: PRT
<213> ORGANISM: Homo sapiens

<400> SEQUENCE: 6

```
Glu Phe Arg His Gly Leu Asn Asp Ile Phe Glu Ala Gln Lys Ile Glu
1               5                   10                  15

Trp His Glu Ser Gln Val Ser Asp Leu Leu Thr Gln Glu Gln Ala Asn
            20                  25                  30

Leu Thr His Gln Lys Lys Lys Leu Glu Gly Gln Ile Ser Ala Arg Gln
        35                  40                  45

Gln Ala Glu Glu Ala Ser Gln Glu Ser Glu Asn Glu Leu Lys Glu Met
    50                  55                  60

Ile Glu Thr Leu Ala Arg Lys Leu Asn Glu Lys Ser Lys Glu Gln Met
65                  70                  75                  80

Glu Leu His His Gln Asn Leu Asn Leu Gln Glu Thr Leu Lys Arg Val
                85                  90                  95

Ala Asn Cys Ser Ala Pro Cys Pro Gln Asp Trp Ile Trp His Gly Glu
            100                 105                 110

Asn Cys Tyr Leu Phe Ser Ser Gly Ser Phe Asn Trp Glu Lys Ser Gln
        115                 120                 125

Glu Lys Cys Leu Ser Leu Asp Ala Lys Leu Leu Lys Ile Asn Ser Thr
    130                 135                 140

Ala Asp Leu Asp Phe Ile Gln Gln Ala Ile Ser Tyr Ser Ser Phe Pro
145                 150                 155                 160

Phe Trp Met Gly Leu Ser Arg Arg Asn Pro Ser Tyr Pro Trp Leu Trp
                165                 170                 175

Glu Asp Gly Ser Pro Leu Met Pro His Leu Phe Arg Val Arg Gly Ala
            180                 185                 190

Val Ser Gln Thr Tyr Pro Ser Gly Thr Cys Ala Tyr Ile Gln Arg Gly
        195                 200                 205

Ala Val Tyr Ala Glu Asn Cys Ile Leu Ala Ala Phe Ser Ile Cys Gln
    210                 215                 220

Lys Lys Ala Asn Leu Arg Ala Gln
225                 230
```

<210> SEQ ID NO 7
<211> LENGTH: 750
<212> TYPE: DNA
<213> ORGANISM: Homo sapiens

<400> SEQUENCE: 7

```
atgcccctgc tgctgctcct ccccctgctg tgggctggcg ccctggccga gttccggcac     60
```

```
ggcctgaacg acatcttcga ggcccagaaa atcgagtggc acgagagcca ggtgtccgat    120

ctgctgaccc aggaacaggc caacctgacc caccagaaga agaagctgga aggccagatc    180

agcgccagac agcaggccga ggaagccagc caggaaagcg agaacgagct gaaagagatg    240

atcgagacac tggcccggaa gctgaacgag aagtccaaag aacagatgga actgcaccac    300

cagaacctga atctgcagga aaccctgaag cgggtcgcca actgcagcgc cccctgcccc    360

caggactgga tctggcacgg cgagaactgc tacctgttca gcagcggcag cttcaactgg    420

gagaagtccc aggaaaagtg cctgagcctg gacgccaagc tgctgaagat caacagcacc    480

gccgacctgg acttcatcca gcaggccatc agctacagca gcttcccttt ctggatgggc    540

ctgagccggc ggaaccccag ctacccttgg ctctgggagg acggcagccc cctgatgccc    600

cacctgttca gagtgcgggg agctgtgagc cagacctacc ccagcggcac ctgtgcctac    660

atccagcgcg gagccgtgta cgccgagaac tgcatcctgg ccgccttcag catctgccag    720

aagaaggcca atctgcgggc ccagtaataa                                     750
```

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 8

```
Asp Tyr Glu Val His
1               5
```

<210> SEQ ID NO 9
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 9

```
Ala Ile His Pro Gly Ser Gly Gly Ala Ala Tyr Val Gln Lys Phe Gln
1               5                   10                  15

Gly
```

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 10

```
Trp Leu Pro Met Asp Tyr
1               5
```

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 11

```
Gly Tyr Thr Phe Thr Asp Tyr
1               5


<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

His Pro Gly Ser Gly Gly
1               5


<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Trp Leu Pro Met Asp Tyr
1               5


<210> SEQ ID NO 14
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Val His Trp Val Arg Gln Ala Pro Gly Gln Gly Leu Glu Trp Met
        35                  40                  45

Gly Ala Ile His Pro Gly Ser Gly Gly Ala Ala Tyr Val Gln Lys Phe
    50                  55                  60

Gln Gly Arg Val Thr Met Thr Arg Asp Thr Ser Thr Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Trp Leu Pro Met Asp Tyr Trp Gly Gln Gly Thr Leu Val Thr
            100                 105                 110

Val Ser Ser
        115


<210> SEQ ID NO 15
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15

caggtgcagc tggtgcagtc tggcgccgaa gtgaagaaac ctggcgcctc cgtgaaggtg     60
```

```
tcctgcaagg cttccggcta cacctttacc gactacgagg tgcactgggt gcgacaggct    120

ccaggccagg gactggaatg gatgggcgct atccatcctg gctctggcgg cgctgcttac    180

gtgcagaaat tccagggcag agtgaccatg acccgggaca cctctacctc caccgcctac    240

atggaactgt cctccctgcg gagcgacgac accgccgtgt actactgtgc ccggtggctg    300

cccatggact attggggcca gggcaccctc gtgaccgtgt cctct                   345


<210> SEQ ID NO 16
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Val His Trp Val Arg Gln Ala Pro Gly Gln Gly Leu Glu Trp Met
        35                  40                  45

Gly Ala Ile His Pro Gly Ser Gly Gly Ala Ala Tyr Val Gln Lys Phe
    50                  55                  60

Gln Gly Arg Val Thr Met Thr Arg Asp Thr Ser Thr Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Trp Leu Pro Met Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300
```

```
Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445
```

<210> SEQ ID NO 17
<211> LENGTH: 1335
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 17

```
caggtgcagc tggtgcagtc tggcgccgaa gtgaagaaac ctggcgcctc cgtgaaggtg     60

tcctgcaagg cttccggcta cacctttacc gactacgagg tgcactgggt gcgacaggct    120

ccaggccagg gactggaatg gatgggcgct atccatcctg gctctggcgg cgctgcttac    180

gtgcagaaat tccagggcag agtgaccatg acccgggaca cctctacctc caccgcctac    240

atggaactgt cctccctgcg gagcgacgac accgccgtgt actactgtgc ccggtggctg    300

cccatggact attggggcca gggcaccctc gtgaccgtgt cctctgcttc taccaagggc    360

ccttccgtgt tccctctggc cccttccagc aagtctacct ctggcggcac cgcagctctg    420

ggctgcctgg tgaaggacta cttccctgag cctgtgacag tgtcctggaa ctctggcgcc    480

ctgaccagcg gagtgcacac cttccctgcc gtgctgcagt cctccggcct gtactccctg    540

tcctccgtgg tgacagtgcc ttcctccagc ctgggcacac agacctacat ctgcaacgtg    600

aaccacaagc cttccaacac caaggtggac aagcgggtgg agcctaagtc ctgcgacaag    660

acccacacct gtcctccatg tcctgcccct gaagccgctg gcggcccttc tgtgtttctg    720

ttccccccaa agcccaagga caccctgatg atctcccgga cccctgaagt gacctgcgtg    780

gtggtggacg tgtcccacga ggatcctgaa gtgaagttca attggtacgt ggacggcgtg    840

gaggtgcaca acgccaagac caagcctcgg gaggaacagt acaactccac ctaccgggtg    900

gtgtccgtgc tgaccgtgct gcaccaggac tggctgaacg gcaaagaata caagtgcaag    960

gtgtccaaca aggccctgcc tgcccctatc gaaaagacca tctccaaggc caagggccag   1020

cctagggaac cccaggtgta caccctgcca cccagccggg aagaaatgac caagaaccag   1080

gtgtccctga cctgtctggt gaagggcttc tacccttccg atatcgccgt ggagtgggag   1140

tctaacggcc agcctgagaa caactacaag accacccctc ctgtgctgga ctccgacggc   1200

tccttcttcc tgtactccaa actgaccgtg gacaagtccc ggtggcagca gggcaacgtg   1260
```

ttctcctgct ctgtgatgca cgaggccctg cacaaccact acacccagaa gtccctgtcc 1320
ctgtctcccg gcaag 1335

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 18

Arg Ala Ser Gln Gly Ile Asn Asn Trp Leu Val
1 5 10

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 19

Ala Ala Ser Ser Leu Gln Ser
1 5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 20

Gln Gln Tyr Leu Ile Thr Pro Tyr Thr
1 5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 21

Ser Gln Gly Ile Asn Asn Trp
1 5

<210> SEQ ID NO 22
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 22

Ala Ala Ser
1

<210> SEQ ID NO 23
<211> LENGTH: 6
<212> TYPE: PRT

<213> ORGANISM: Artificial Sequence
<220> FEATURE:
<223> OTHER INFORMATION: Description of Artificial Sequence: Synthetic peptide

<400> SEQUENCE: 23

```
Tyr Leu Ile Thr Pro Tyr
1               5
```

<210> SEQ ID NO 24
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 24

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Asn Asn Trp
            20                  25                  30

Leu Val Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Ala Asp Tyr Thr Leu Thr Ile Ser Ser Leu Gln Pro
65                  70                  75                  80

Glu Asp Phe Ala Thr Tyr Tyr Cys Gln Gln Tyr Leu Ile Thr Pro Tyr
                85                  90                  95

Thr Phe Gly Gln Gly Thr Lys Leu Glu Ile Lys
            100                 105
```

<210> SEQ ID NO 25
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 25

```
gacatccaga tgacccagtc cccctcctcc gtgtctgctt ccgtgggcga cagagtgacc     60

atcacctgta gagcctccca gggcatcaac aactggctcg tgtggtatca gcagaagccc    120

ggcaaggccc ccaagctgct gatctacgct gcctccagtc tgcagtccgg cgtgccctct    180

agattctccg gctctggctc tggcgccgac tataccctga ccatctccag cctgcagccc    240

gaggacttcg ccacctacta ctgccagcag tacctgatca ccccctacac cttcggccag    300

ggcaccaagc tggaaatcaa g                                              321
```

<210> SEQ ID NO 26
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 26

```
Asp Ile Gln Met Thr Gln Ser Pro Ser Ser Val Ser Ala Ser Val Gly
1               5                   10                  15
```

```
Asp Arg Val Thr Ile Thr Cys Arg Ala Ser Gln Gly Ile Asn Asn Trp
            20                  25                  30

Leu Val Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Ala Asp Tyr Thr Leu Thr Ile Ser Ser Leu Gln Pro
65                  70                  75                  80

Glu Asp Phe Ala Thr Tyr Tyr Cys Gln Gln Tyr Leu Ile Thr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 27
<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 27

```
gacatccaga tgacccagtc cccctcctcc gtgtctgctt ccgtgggcga cagagtgacc     60

atcacctgta gagcctccca gggcatcaac aactggctcg tgtggtatca gcagaagccc    120

ggcaaggccc ccaagctgct gatctacgct gcctccagtc tgcagtccgg cgtgccctct    180

agattctccg gctctggctc tggcgccgac tataccctga ccatctccag cctgcagccc    240

gaggacttcg ccacctacta ctgccagcag tacctgatca ccccctacac cttcggccag    300

ggcaccaagc tggaaatcaa gcgtacggtg gccgctccca gcgtgttcat cttccccccca    360

agcgacgagc agctgaagag cggcaccgcc agcgtggtgt gtctgctgaa caacttctac    420

cccagggagg ccaaggtgca gtggaaggtg gacaacgccc tgcagagcgg caacagccag    480

gagagcgtca ccgagcagga cagcaaggac tccacctaca gcctgagcag caccctgacc    540

ctgagcaagg ccgactacga gaagcacaag gtgtacgcct gtgaggtgac ccaccagggc    600

ctgtccagcc ccgtgaccaa gagcttcaac aggggcgagt gc                         642
```

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 28

Asp Tyr Glu Val His
1 5

<210> SEQ ID NO 29
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 29

Ala Ile His Pro Gly Ser Gly Gly Ala Ala Tyr Val Gln Lys Phe Gln
1 5 10 15

Gly

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 30

Trp Leu Pro Met Asp Tyr
1 5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 31

Gly Tyr Thr Phe Thr Asp Tyr
1 5

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 32

His Pro Gly Ser Gly Gly
1 5

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 33

Trp Leu Pro Met Asp Tyr
1 5

<210> SEQ ID NO 34
<211> LENGTH: 115
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 34

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Val His Trp Val Arg Gln Ala Pro Gly Gln Gly Leu Glu Trp Met
        35                  40                  45

Gly Ala Ile His Pro Gly Ser Gly Gly Ala Ala Tyr Val Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Trp Leu Pro Met Asp Tyr Trp Gly Gln Gly Thr Leu Val Thr
            100                 105                 110

Val Ser Ser
        115
```

<210> SEQ ID NO 35
<211> LENGTH: 345
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 35

```
caggtgcagc tggtgcagtc tggcgccgaa gtgaagaaac ctggcgcctc cgtgaaggtg     60

tcctgcaagg cttccggcta cacctttacc gactacgagg tgcactgggt gcgacaggct    120

ccaggccagg gactggaatg gatgggcgct atccatcctg gctctggcgg cgctgcttac    180

gtgcagaaat tccagggcag agtgaccatg acccgggaca cctccatctc caccgcctac    240

atggaactgt cccggctgag atccgacgac accgccgtgt actactgcgc cagatggctg    300

cccatggact actggggcca gggcacactc gtgaccgtgt cctct                    345
```

<210> SEQ ID NO 36
<211> LENGTH: 445
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 36

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Val His Trp Val Arg Gln Ala Pro Gly Gln Gly Leu Glu Trp Met
        35                  40                  45

Gly Ala Ile His Pro Gly Ser Gly Gly Ala Ala Tyr Val Gln Lys Phe
```

```
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Trp Leu Pro Met Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445
```

<210> SEQ ID NO 37
<211> LENGTH: 1335
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 37

```
caggtgcagc tggtgcagtc tggcgccgaa gtgaagaaac ctggcgcctc cgtgaaggtg     60

tcctgcaagg cttccggcta cacctttacc gactacgagg tgcactgggt gcgacaggct    120

ccaggccagg gactggaatg gatgggcgct atccatcctg gctctggcgg cgctgcttac    180

gtgcagaaat tccagggcag agtgaccatg acccgggaca cctccatctc caccgcctac    240

atggaactgt cccggctgag atccgacgac accgccgtgt actactgcgc cagatggctg    300

cccatggact actggggcca gggcacactc gtgaccgtgt cctctgcttc caccaagggc    360

ccttccgtgt tccctctggc cccttccagc aagtctacct ctggcggcac cgcagctctg    420

ggctgcctgg tgaaggacta cttccctgag cctgtgacag tgtcctggaa ctctggcgcc    480

ctgaccagcg gagtgcacac cttccctgcc gtgctgcagt cctccggcct gtactccctg    540

tcctccgtgg tgacagtgcc ttcctccagc ctgggcacac agacctacat ctgcaacgtg    600

aaccacaagc cttccaacac caaggtggac aagcgggtgg agcctaagtc ctgcgacaag    660

acccacacct gtcctccatg tcctgcccct gaagccgctg gcggcccttc tgtgtttctg    720

ttccccccaa agcccaagga caccctgatg atctcccgga cccctgaagt gacctgcgtg    780

gtggtggacg tgtcccacga ggatcctgaa gtgaagttca attggtacgt ggacggcgtg    840

gaggtgcaca acgccaagac caagcctcgg gaggaacagt acaactccac ctaccgggtg    900

gtgtccgtgc tgaccgtgct gcaccaggac tggctgaacg gcaaagaata caagtgcaag    960

gtgtccaaca aggccctgcc tgcccctatc gaaaagacca tctccaaggc caagggccag   1020

cctagggaac cccaggtgta caccctgcca cccagccggg aagaaatgac caagaaccag   1080

gtgtccctga cctgtctggt gaagggcttc tacccttccg atatcgccgt ggagtgggag   1140

tctaacggcc agcctgagaa caactacaag accacccctc ctgtgctgga ctccgacggc   1200

tccttcttcc tgtactccaa actgaccgtg gacaagtccc ggtggcagca gggcaacgtg   1260

ttctcctgct ctgtgatgca cgaggccctg cacaaccact acacccagaa gtccctgtcc   1320

ctgtctcccg gcaag                                                    1335
```

<210> SEQ ID NO 38
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 38

```
Arg Ala Ser Gln Gly Ile Asn Asn Trp Leu Val
1               5                   10
```

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 39

```
Ala Ala Ser Ser Leu Gln Ser
1               5
```

```
<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gln Gln Tyr Leu Ile Thr Pro Tyr Thr
1               5


<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ser Gln Gly Ile Asn Asn Trp
1               5


<210> SEQ ID NO 42
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ala Ala Ser
1


<210> SEQ ID NO 43
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Tyr Leu Ile Thr Pro Tyr
1               5


<210> SEQ ID NO 44
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Asn Asn Trp
            20                  25                  30

Leu Val Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60
```

Ser Gly Ser Gly Ala Asp Tyr Thr Leu Thr Ile Ser Ser Leu Gln Pro
65 70 75 80

Glu Asp Phe Ala Thr Tyr Tyr Cys Gln Gln Tyr Leu Ile Thr Pro Tyr
85 90 95

Thr Phe Gly Gln Gly Thr Lys Leu Glu Ile Lys
100 105

<210> SEQ ID NO 45
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 45
gacatccaga tgacccagtc cccctcctcc gtgtctgctt ccgtgggcga cagagtgacc 60
atcacctgta gagcctccca gggcatcaac aactggctcg tgtggtatca gcagaagccc 120
ggcaaggccc ccaagctgct gatctacgct gcctccagtc tgcagtccgg cgtgccctct 180
agattctccg gctctggctc tggcgccgac tataccctga ccatctccag cctgcagccc 240
gaggacttcg ccacctacta ctgccagcag tacctgatca ccccctacac cttcggccag 300
ggcaccaagc tggaaatcaa g 321

<210> SEQ ID NO 46
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 46

Asp Ile Gln Met Thr Gln Ser Pro Ser Ser Val Ser Ala Ser Val Gly
1 5 10 15

Asp Arg Val Thr Ile Thr Cys Arg Ala Ser Gln Gly Ile Asn Asn Trp
20 25 30

Leu Val Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Ala Asp Tyr Thr Leu Thr Ile Ser Ser Leu Gln Pro
65 70 75 80

Glu Asp Phe Ala Thr Tyr Tyr Cys Gln Gln Tyr Leu Ile Thr Pro Tyr
85 90 95

Thr Phe Gly Gln Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

```
Ala Cys Glu Val Thr His Gln Gly Leu Ser Ser Pro Val Thr Lys Ser
        195                 200                 205

Phe Asn Arg Gly Glu Cys
    210


<210> SEQ ID NO 47
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47

gacatccaga tgacccagtc cccctcctcc gtgtctgctt ccgtgggcga cagagtgacc      60

atcacctgta gagcctccca gggcatcaac aactggctcg tgtggtatca gcagaagccc     120

ggcaaggccc ccaagctgct gatctacgct gcctccagtc tgcagtccgg cgtgccctct     180

agattctccg gctctggctc tggcgccgac tataccctga ccatctccag cctgcagccc     240

gaggacttcg ccacctacta ctgccagcag tacctgatca ccccctacac cttcggccag     300

ggcaccaagc tggaaatcaa gcgtacggtg gccgctccca gcgtgttcat cttccccccca     360

agcgacgagc agctgaagag cggcaccgcc agcgtggtgt gtctgctgaa caacttctac     420

cccagggagg ccaaggtgca gtggaaggtg gacaacgccc tgcagagcgg caacagccag     480

gagagcgtca ccgagcagga cagcaaggac tccacctaca gcctgagcag caccctgacc     540

ctgagcaagg ccgactacga gaagcacaag gtgtacgcct gtgaggtgac ccaccagggc     600

ctgtccagcc ccgtgaccaa gagcttcaac aggggcgagt gc                        642


<210> SEQ ID NO 48
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Asp Tyr Glu Val His
1               5


<210> SEQ ID NO 49
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ala Ile His Pro Gly Ser Gly Gly Ala Ala Tyr Val Gln Lys Phe Gln
1               5                   10                  15

Gly


<210> SEQ ID NO 50
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 50

```
Trp Leu Pro Met Asp Tyr
1               5
```

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 51

```
Gly Tyr Thr Phe Thr Asp Tyr
1               5
```

<210> SEQ ID NO 52
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 52

```
His Pro Gly Ser Gly Gly
1               5
```

<210> SEQ ID NO 53
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 53

```
Trp Leu Pro Met Asp Tyr
1               5
```

<210> SEQ ID NO 54
<211> LENGTH: 115
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 54

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Val His Trp Val Arg Gln Ala Pro Gly Gln Gly Leu Glu Trp Met
        35                  40                  45

Gly Ala Ile His Pro Gly Ser Gly Gly Ala Ala Tyr Val Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Trp Leu Pro Met Asp Tyr Trp Gly Gln Gly Thr Leu Val Thr
            100                 105                 110
```

```
Val Ser Ser
        115


<210> SEQ ID NO 55
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55

caggtgcagc tggtgcagtc tggcgccgaa gtgaagaaac ctggcgcctc cgtgaaggtg      60

tcctgcaagg cttccggcta cacctttacc gactacgagg tgcactgggt gcgacaggct     120

ccaggccagg gactggaatg gatgggcgct atccatcctg gctctggcgg cgctgcttac     180

gtgcagaaat tccagggcag agtgaccatg acccgggaca cctccatctc caccgcctac     240

atggaactgt cccggctgag atccgacgac accgccgtgt actactgcgc cagatggctg     300

cccatggact actggggcca gggcacactc gtgaccgtgt cctct                     345


<210> SEQ ID NO 56
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Val His Trp Val Arg Gln Ala Pro Gly Gln Gly Leu Glu Trp Met
        35                  40                  45

Gly Ala Ile His Pro Gly Ser Gly Gly Ala Ala Tyr Val Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Trp Leu Pro Met Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220
```

```
Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445
```

```
<210> SEQ ID NO 57
<211> LENGTH: 1335
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57

caggtgcagc tggtgcagtc tggcgccgaa gtgaagaaac ctggcgcctc cgtgaaggtg     60

tcctgcaagg cttccggcta cacctttacc gactacgagg tgcactgggt gcgacaggct    120

ccaggccagg gactggaatg gatgggcgct atccatcctg gctctggcgg cgctgcttac    180

gtgcagaaat tccagggcag agtgaccatg acccgggaca cctccatctc caccgcctac    240

atggaactgt cccggctgag atccgacgac accgccgtgt actactgcgc cagatggctg    300

cccatggact actggggcca gggcacactc gtgaccgtgt cctctgcttc caccaagggc    360

ccttccgtgt tccctctggc cccttccagc aagtctacct ctggcggcac cgcagctctg    420

ggctgcctgg tgaaggacta cttccctgag cctgtgacag tgtcctggaa ctctggcgcc    480

ctgaccagcg gagtgcacac cttccctgcc gtgctgcagt cctccggcct gtactccctg    540

tcctccgtgg tgacagtgcc ttcctccagc ctgggcacac agacctacat ctgcaacgtg    600

aaccacaagc cttccaacac caaggtggac aagcgggtgg agcctaagtc ctgcgacaag    660

acccacacct gtcctccatg tcctgcccct gaagccgctg gcggcccttc tgtgtttctg    720

ttccccccaa agcccaagga caccctgatg atctcccgga cccctgaagt gacctgcgtg    780
```

```
gtggtggacg tgtcccacga ggatcctgaa gtgaagttca attggtacgt ggacggcgtg    840

gaggtgcaca acgccaagac caagcctcgg gaggaacagt acaactccac ctaccgggtg    900

gtgtccgtgc tgaccgtgct gcaccaggac tggctgaacg gcaaagaata caagtgcaag    960

gtgtccaaca aggccctgcc tgcccctatc gaaaagacca tctccaaggc caagggccag   1020

cctagggaac cccaggtgta caccctgcca cccagccggg aagaaatgac caagaaccag   1080

gtgtccctga cctgtctggt gaagggcttc tacccttccg atatcgccgt ggagtgggag   1140

tctaacggcc agcctgagaa caactacaag accacccctc ctgtgctgga ctccgacggc   1200

tccttcttcc tgtactccaa actgaccgtg gacaagtccc ggtggcagca gggcaacgtg   1260

ttctcctgct ctgtgatgca cgaggccctg cacaaccact acacccagaa gtccctgtcc   1320

ctgtctcccg gcaag                                                    1335


<210> SEQ ID NO 58
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Arg Ala Ser Gln Gly Ile Thr Asn Trp Leu Ala
1               5                   10


<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ala Ala Ser Ile Leu Glu Ser
1               5


<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gln Gln Tyr Leu Ile Thr Pro Tyr Thr
1               5


<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ser Gln Gly Ile Thr Asn Trp
1               5


<210> SEQ ID NO 62
<211> LENGTH: 3
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ala Ala Ser
1


<210> SEQ ID NO 63
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Tyr Leu Ile Thr Pro Tyr
1               5


<210> SEQ ID NO 64
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Thr Asn Trp
            20                  25                  30

Leu Ala Trp Tyr Gln Gln Lys Pro Gly Lys Ala Pro Lys Leu Leu Ile
        35                  40                  45

Tyr Ala Ala Ser Ile Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Ile Ala Thr Tyr Tyr Cys Gln Gln Tyr Leu Ile Thr Pro Tyr
                85                  90                  95

Thr Phe Gly Gln Gly Thr Lys Leu Glu Ile Lys
            100                 105


<210> SEQ ID NO 65
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65

gacatccaga tgacccagtc cccctcctcc gtgtctgctt ccgtgggcga cagagtgacc      60

atcacctgta gagcctccca gggcatcacc aactggctgg cctggtatca gcagaagccc     120

ggcaaggccc ccaagctgct gatctacgcc gcctccatcc tggaatccgg cgtgccctct     180

agattctccg gctctggctc tggcaccgac tataccctga ccatctccag cctgcagccc     240

gaggatatcg ccacctacta ctgccagcag tacctgatca cccctacac cttcggccag     300

ggcaccaagc tggaaatcaa g                                               321
```

<210> SEQ ID NO 66
<211> LENGTH: 214
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 66

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Thr Asn Trp
            20                  25                  30

Leu Ala Trp Tyr Gln Gln Lys Pro Gly Lys Ala Pro Lys Leu Leu Ile
        35                  40                  45

Tyr Ala Ala Ser Ile Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Ile Ala Thr Tyr Tyr Cys Gln Gln Tyr Leu Ile Thr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 67
<211> LENGTH: 642
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 67

```
gacatccaga tgacccagtc cccctcctcc gtgtctgctt ccgtgggcga cagagtgacc      60

atcacctgta gagcctccca gggcatcacc aactggctgg cctggtatca gcagaagccc     120

ggcaaggccc ccaagctgct gatctacgcc gcctccatcc tggaatccgg cgtgccctct     180

agattctccg gctctggctc tggcaccgac tataccctga ccatctccag cctgcagccc     240

gaggatatcg ccacctacta ctgccagcag tacctgatca ccccctacac cttcggccag     300

ggcaccaagc tggaaatcaa gcgtacggtg gccgctccca gcgtgttcat cttcccccca     360

agcgacgagc agctgaagag cggcaccgcc agcgtggtgt gtctgctgaa caacttctac     420
```

```
cccagggagg ccaaggtgca gtggaaggtg gacaacgccc tgcagagcgg caacagccag    480

gagagcgtca ccgagcagga cagcaaggac tccacctaca gcctgagcag caccctgacc    540

ctgagcaagg ccgactacga gaagcacaag gtgtacgcct gtgaggtgac ccaccagggc    600

ctgtccagcc ccgtgaccaa gagcttcaac aggggcgagt gc                       642


<210> SEQ ID NO 68
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Asp Tyr Glu Val His
1               5


<210> SEQ ID NO 69
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Ala Ile His Pro Gly Ser Gly Gly Ala Ala Tyr Val Gln Lys Phe Gln
1               5                   10                  15

Gly


<210> SEQ ID NO 70
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Trp Leu Pro Met Asp Tyr
1               5


<210> SEQ ID NO 71
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gly Tyr Thr Phe Thr Asp Tyr
1               5


<210> SEQ ID NO 72
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

His Pro Gly Ser Gly Gly
1               5
```

<210> SEQ ID NO 73
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 73

```
Trp Leu Pro Met Asp Tyr
1               5
```

<210> SEQ ID NO 74
<211> LENGTH: 115
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 74

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Val His Trp Val Arg Gln Ala Pro Gly Gln Gly Leu Glu Trp Met
        35                  40                  45

Gly Ala Ile His Pro Gly Ser Gly Gly Ala Ala Tyr Val Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Trp Leu Pro Met Asp Tyr Trp Gly Gln Gly Thr Leu Val Thr
            100                 105                 110

Val Ser Ser
        115
```

<210> SEQ ID NO 75
<211> LENGTH: 345
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 75

```
caggtgcagc tggtgcagtc tggcgccgaa gtgaagaaac ctggcgcctc cgtgaaggtg     60

tcctgcaagg cttccggcta cacctttacc gactacgagg tgcactgggt gcgacaggct    120

ccaggccagg gactggaatg gatgggcgct atccatcctg gctctggcgg cgctgcttac    180

gtgcagaaat tccagggcag agtgaccatg acccgggaca cctccatctc caccgcctac    240

atggaactgt cccggctgag atccgacgac accgccgtgt actactgcgc cagatggctg    300

cccatggact actggggcca gggcacactc gtgaccgtgt cctct                    345
```

<210> SEQ ID NO 76
<211> LENGTH: 445
<212> TYPE: PRT
<213> ORGANISM: Artificial Sequence
<220> FEATURE:

<223> OTHER INFORMATION: Description of Artificial Sequence: Synthetic polypeptide

<400> SEQUENCE: 76

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Val His Trp Val Arg Gln Ala Pro Gly Gln Gly Leu Glu Trp Met
        35                  40                  45

Gly Ala Ile His Pro Gly Ser Gly Gly Ala Ala Tyr Val Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Trp Leu Pro Met Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400
```

Ser Phe Phe Leu Tyr Ser Lys Leu Thr Val Asp Lys Ser Arg Trp Gln
405 410 415

Gln Gly Asn Val Phe Ser Cys Ser Val Met His Glu Ala Leu His Asn
420 425 430

His Tyr Thr Gln Lys Ser Leu Ser Leu Ser Pro Gly Lys
435 440 445

<210> SEQ ID NO 77
<211> LENGTH: 1335
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 77
caggtgcagc tggtgcagtc tggcgccgaa gtgaagaaac ctggcgcctc cgtgaaggtg 60
tcctgcaagg cttccggcta cacctttacc gactacgagg tgcactgggt gcgacaggct 120
ccaggccagg gactggaatg gatgggcgct atccatcctg gctctggcgg cgctgcttac 180
gtgcagaaat tccagggcag agtgaccatg acccgggaca cctccatctc caccgcctac 240
atggaactgt cccggctgag atccgacgac accgccgtgt actactgcgc cagatggctg 300
cccatggact actggggcca gggcacactc gtgaccgtgt cctctgcttc caccaagggc 360
ccttccgtgt tccctctggc cccttccagc aagtctacct ctggcggcac cgcagctctg 420
ggctgcctgg tgaaggacta cttccctgag cctgtgacag tgtcctggaa ctctggcgcc 480
ctgaccagcg gagtgcacac cttccctgcc gtgctgcagt cctccggcct gtactccctg 540
tcctccgtgg tgacagtgcc ttcctccagc ctgggcacac agacctacat ctgcaacgtg 600
aaccacaagc cttccaacac caaggtggac aagcgggtgg agcctaagtc ctgcgacaag 660
acccacacct gtcctccatg tcctgcccct gaagccgctg gcggcccttc tgtgtttctg 720
ttccccccaa agcccaagga caccctgatg atctcccgga cccctgaagt gacctgcgtg 780
gtggtggacg tgtcccacga ggatcctgaa gtgaagttca attggtacgt ggacggcgtg 840
gaggtgcaca acgccaagac caagcctcgg gaggaacagt acaactccac ctaccgggtg 900
gtgtccgtgc tgaccgtgct gcaccaggac tggctgaacg gcaaagaata caagtgcaag 960
gtgtccaaca aggccctgcc tgcccctatc gaaaagacca tctccaaggc caagggccag 1020
cctagggaac cccaggtgta caccctgcca cccagccggg aagaaatgac caagaaccag 1080
gtgtccctga cctgtctggt gaagggcttc tacccttccg atatcgccgt ggagtgggag 1140
tctaacggcc agcctgagaa caactacaag accacccctc ctgtgctgga ctccgacggc 1200
tccttcttcc tgtactccaa actgaccgtg gacaagtccc ggtggcagca gggcaacgtg 1260
ttctcctgct ctgtgatgca cgaggccctg cacaaccact acacccagaa gtccctgtcc 1320
ctgtctcccg gcaag 1335

<210> SEQ ID NO 78
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 78

Arg Ala Ser Gln Gly Ile Asn Asn Trp Leu Val 1 5 10

<210> SEQ ID NO 79
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 79

Ala Ala Ser Arg Leu Glu Ser
1 5

<210> SEQ ID NO 80
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 80

Gln Gln Tyr Leu Ile Thr Pro Tyr Thr
1 5

<210> SEQ ID NO 81
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 81

Ser Gln Gly Ile Asn Asn Trp
1 5

<210> SEQ ID NO 82
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 82

Ala Ala Ser
1

<210> SEQ ID NO 83
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 83

Tyr Leu Ile Thr Pro Tyr
1 5

<210> SEQ ID NO 84
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 84

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Asn Asn Trp
            20                  25                  30

Leu Val Trp Tyr Gln Gln Lys Pro Gly Lys Ala Pro Lys Leu Leu Leu
        35                  40                  45

Tyr Ala Ala Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Ile Ala Thr Tyr Tyr Cys Gln Gln Tyr Leu Ile Thr Pro Tyr
                85                  90                  95

Thr Phe Gly Gln Gly Thr Lys Leu Glu Ile Lys
            100                 105
```

<210> SEQ ID NO 85
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 85

```
gacatccaga tgacccagtc cccctcctcc gtgtctgctt ccgtgggcga cagagtgacc     60

atcacctgta gagcctccca gggcatcaac aactggctcg tgtggtatca gcagaagccc    120

ggcaaggccc ccaaactgct gctgtacgcc gcctccagac tggaatctgg cgtgccctcc    180

agattctccg gctctggctc tggcaccgac tataccctga ccatctccag cctgcagccc    240

gaggatatcg ccacctacta ctgccagcag tacctgatca cccccctacac cttcggccag    300

ggcaccaagc tggaaatcaa g                                              321
```

<210> SEQ ID NO 86
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 86

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Asn Asn Trp
            20                  25                  30

Leu Val Trp Tyr Gln Gln Lys Pro Gly Lys Ala Pro Lys Leu Leu Leu
        35                  40                  45

Tyr Ala Ala Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Ile Ala Thr Tyr Tyr Cys Gln Gln Tyr Leu Ile Thr Pro Tyr
                85                  90                  95

Thr Phe Gly Gln Gly Thr Lys Leu Glu Ile Lys Arg Thr Val Ala Ala
            100                 105                 110
```

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 87
<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 87

```
gacatccaga tgacccagtc cccctcctcc gtgtctgctt ccgtgggcga cagagtgacc     60

atcacctgta gagcctccca gggcatcaac aactggctcg tgtggtatca gcagaagccc    120

ggcaaggccc ccaaactgct gctgtacgcc gcctccagac tggaatctgg cgtgccctcc    180

agattctccg gctctggctc tggcaccgac tataccctga ccatctccag cctgcagccc    240

gaggatatcg ccacctacta ctgccagcag tacctgatca ccccctacac cttcggccag    300

ggcaccaagc tggaaatcaa gcgtacggtg gccgctccca gcgtgttcat cttcccccca    360

agcgacgagc agctgaagag cggcaccgcc agcgtggtgt gtctgctgaa caacttctac    420

cccagggagg ccaaggtgca gtggaaggtg gacaacgccc tgcagagcgg caacagccag    480

gagagcgtca ccgagcagga cagcaaggac tccacctaca gcctgagcag caccctgacc    540

ctgagcaagg ccgactacga gaagcacaag gtgtacgcct gtgaggtgac ccaccagggc    600

ctgtccagcc ccgtgaccaa gagcttcaac aggggcgagt gc                       642
```

<210> SEQ ID NO 88
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 88

```
Asp Tyr Glu Val His
1               5
```

<210> SEQ ID NO 89
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 89

```
Ala Ile His Pro Gly Ser Gly Gly Ala Ala Tyr Val Gln Lys Phe Gln
1               5                   10                  15

Gly


<210> SEQ ID NO 90
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Trp Leu Pro Ile Asp Tyr
1               5


<210> SEQ ID NO 91
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Gly Tyr Thr Phe Thr Asp Tyr
1               5


<210> SEQ ID NO 92
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

His Pro Gly Ser Gly Gly
1               5


<210> SEQ ID NO 93
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Trp Leu Pro Ile Asp Tyr
1               5


<210> SEQ ID NO 94
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30
```

```
Glu Val His Trp Val Arg Gln Ala Pro Gly Gln Gly Leu Glu Trp Met
        35                  40                  45

Gly Ala Ile His Pro Gly Ser Gly Gly Ala Ala Tyr Val Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Trp Leu Pro Ile Asp Tyr Trp Gly Gln Gly Thr Leu Val Thr
            100                 105                 110

Val Ser Ser
        115


<210> SEQ ID NO 95
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 95

caggtgcagc tggtgcagtc tggcgccgaa gtgaagaaac ctggcgcctc cgtgaaggtg      60

tcctgcaagg cttccggcta cacctttacc gactacgagg tgcactgggt gcgacaggct     120

ccaggccagg gactggaatg gatgggcgct atccatcctg gctctggcgg cgctgcttac     180

gtgcagaaat tccagggcag agtgaccatg acccgggaca cctccatctc caccgcctac     240

atggaactgt cccggctgag atccgacgac accgccgtgt actactgcgc cagatggctg     300

cccatcgact actggggcca gggcacactc gtgaccgtgt cctct                     345


<210> SEQ ID NO 96
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Val His Trp Val Arg Gln Ala Pro Gly Gln Gly Leu Glu Trp Met
        35                  40                  45

Gly Ala Ile His Pro Gly Ser Gly Gly Ala Ala Tyr Val Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Trp Leu Pro Ile Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140
```

```
Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445
```

<210> SEQ ID NO 97
<211> LENGTH: 1335
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 97

```
caggtgcagc tggtgcagtc tggcgccgaa gtgaagaaac ctggcgcctc cgtgaaggtg     60

tcctgcaagg cttccggcta cacctttacc gactacgagg tgcactgggt gcgacaggct    120

ccaggccagg gactggaatg gatgggcgct atccatcctg gctctggcgg cgctgcttac    180

gtgcagaaat tccagggcag agtgaccatg acccgggaca cctccatctc caccgcctac    240

atggaactgt cccggctgag atccgacgac accgccgtgt actactgcgc cagatggctg    300

cccatcgact actggggcca gggcacactc gtgaccgtgt cctctgcttc caccaagggc    360
```

```
ccttccgtgt tccctctggc cccttccagc aagtctacct ctggcggcac cgcagctctg    420

ggctgcctgg tgaaggacta cttccctgag cctgtgacag tgtcctggaa ctctggcgcc    480

ctgaccagcg gagtgcacac cttccctgcc gtgctgcagt cctccggcct gtactccctg    540

tcctccgtgg tgacagtgcc ttcctccagc ctgggcacac agacctacat ctgcaacgtg    600

aaccacaagc cttccaacac caaggtggac aagcgggtgg agcctaagtc ctgcgacaag    660

acccacacct gtcctccatg tcctgcccct gaagccgctg gcggcccttc tgtgtttctg    720

ttcccccaa agcccaagga caccctgatg atctcccgga cccctgaagt gacctgcgtg     780

gtggtggacg tgtcccacga ggatcctgaa gtgaagttca attggtacgt ggacggcgtg    840

gaggtgcaca acgccaagac caagcctcgg gaggaacagt acaactccac ctaccgggtg    900

gtgtccgtgc tgaccgtgct gcaccaggac tggctgaacg gcaaagaata caagtgcaag    960

gtgtccaaca aggccctgcc tgcccctatc gaaaagacca tctccaaggc caagggccag   1020

cctagggaac cccaggtgta caccctgcca cccagccggg aagaaatgac caagaaccag   1080

gtgtccctga cctgtctggt gaagggcttc tacccttccg atatcgccgt ggagtgggag   1140

tctaacggcc agcctgagaa caactacaag accacccctc ctgtgctgga ctccgacggc   1200

tccttcttcc tgtactccaa actgaccgtg gacaagtccc ggtggcagca gggcaacgtg   1260

ttctcctgct ctgtgatgca cgaggccctg cacaaccact acacccagaa gtccctgtcc   1320

ctgtctcccg gcaag                                                    1335
```

```
<210> SEQ ID NO 98
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Arg Ala Ser Gln Gly Ile Asn Asn Trp Leu Val
1               5                   10


<210> SEQ ID NO 99
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Ala Ala Ser Arg Leu Glu Ser
1               5


<210> SEQ ID NO 100
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Gln Gln Tyr Leu Ile Thr Pro Tyr Thr
1               5


<210> SEQ ID NO 101
```

<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 101

Ser Gln Gly Ile Asn Asn Trp
1 5

<210> SEQ ID NO 102
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 102

Ala Ala Ser
1

<210> SEQ ID NO 103
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 103

Tyr Leu Ile Thr Pro Tyr
1 5

<210> SEQ ID NO 104
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 104

Asp Ile Gln Met Thr Gln Ser Pro Ser Ser Val Ser Ala Ser Val Gly
1 5 10 15

Asp Arg Val Thr Ile Thr Cys Arg Ala Ser Gln Gly Ile Asn Asn Trp
20 25 30

Leu Val Trp Tyr Gln Gln Lys Pro Gly Lys Ala Pro Lys Leu Leu Leu
35 40 45

Tyr Ala Ala Ser Arg Leu Glu Ser Gly Val Pro Ser Arg Phe Ser Gly
50 55 60

Ser Gly Ser Gly Thr Asp Tyr Thr Leu Thr Ile Ser Ser Leu Gln Pro
65 70 75 80

Glu Asp Ile Ala Thr Tyr Tyr Cys Gln Gln Tyr Leu Ile Thr Pro Tyr
85 90 95

Thr Phe Gly Gln Gly Thr Lys Leu Glu Ile Lys
100 105

<210> SEQ ID NO 105
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 105

```
gacatccaga tgacccagtc cccctcctcc gtgtctgctt ccgtgggcga cagagtgacc      60

atcacctgta gagcctccca gggcatcaac aactggctcg tgtggtatca gcagaagccc     120

ggcaaggccc ccaaactgct gctgtacgcc gcctccagac tggaatctgg cgtgccctcc     180

agattctccg gctctggctc tggcaccgac tataccctga ccatctccag cctgcagccc     240

gaggatatcg ccacctacta ctgccagcag tacctgatca ccccctacac cttcggccag     300

ggcaccaagc tggaaatcaa g                                               321
```

<210> SEQ ID NO 106
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 106

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Asn Asn Trp
            20                  25                  30

Leu Val Trp Tyr Gln Gln Lys Pro Gly Lys Ala Pro Lys Leu Leu Leu
        35                  40                  45

Tyr Ala Ala Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Ile Ala Thr Tyr Tyr Cys Gln Gln Tyr Leu Ile Thr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 107
<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 107

```
gacatccaga tgacccagtc cccctcctcc gtgtctgctt ccgtgggcga cagagtgacc     60

atcacctgta gagcctccca gggcatcaac aactggctcg tgtggtatca gcagaagccc    120

ggcaaggccc ccaaactgct gctgtacgcc gcctccagac tggaatctgg cgtgccctcc    180

agattctccg gctctggctc tggcaccgac tataccctga ccatctccag cctgcagccc    240

gaggatatcg ccacctacta ctgccagcag tacctgatca ccccctacac cttcggccag    300

ggcaccaagc tggaaatcaa gcgtacggtg gccgctccca gcgtgttcat cttcccccca    360

agcgacgagc agctgaagag cggcaccgcc agcgtggtgt gtctgctgaa caacttctac    420

cccagggagg ccaaggtgca gtggaaggtg gacaacgccc tgcagagcgg caacagccag    480

gagagcgtca ccgagcagga cagcaaggac tccacctaca gcctgagcag caccctgacc    540

ctgagcaagg ccgactacga gaagcacaag gtgtacgcct gtgaggtgac ccaccagggc    600

ctgtccagcc ccgtgaccaa gagcttcaac aggggcgagt gc                       642
```

```
<210> SEQ ID NO 108
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Asp Tyr Glu Met His
1               5


<210> SEQ ID NO 109
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Ala Ile His Pro Gly Ser Gly Gly Ala Ala Tyr Ile Gln Lys Phe Lys
1               5                   10                  15

Gly


<210> SEQ ID NO 110
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Trp Leu Pro Met Asp Tyr
1               5


<210> SEQ ID NO 111
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Gly Tyr Thr Phe Thr Asp Tyr
```

1 5

<210> SEQ ID NO 112
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 112

His Pro Gly Ser Gly Gly
1 5

<210> SEQ ID NO 113
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 113

Trp Leu Pro Met Asp Tyr
1 5

<210> SEQ ID NO 114
<211> LENGTH: 115
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 114

Gln Val Gln Leu Gln Gln Ser Gly Ala Glu Leu Val Arg Pro Gly Ala
1 5 10 15

Ser Val Lys Leu Ser Cys Lys Ala Leu Gly Tyr Thr Phe Thr Asp Tyr
20 25 30

Glu Met His Trp Val Lys Gln Thr Pro Val His Gly Leu Glu Trp Ile
35 40 45

Gly Ala Ile His Pro Gly Ser Gly Gly Ala Ala Tyr Ile Gln Lys Phe
50 55 60

Lys Gly Lys Ala Thr Leu Thr Ala Asp Lys Ser Ser Ser Thr Ala His
65 70 75 80

Met Glu Leu Ser Ser Leu Thr Ser Glu Asp Ser Ala Val Tyr Tyr Cys
85 90 95

Thr Arg Trp Leu Pro Met Asp Tyr Trp Gly Gln Gly Thr Ser Val Thr
100 105 110

Val Ser Ser
115

<210> SEQ ID NO 115
<211> LENGTH: 345
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 115
caggtccagc tgcagcagtc aggagccgaa ctggtgcggc ccggagcttc tgtcaaactg 60
agctgcaagg cactgggcta caccttcaca gactatgaga tgcactgggt gaaacagacc 120

```
cccgtccatg gactggaatg gatcggagca attcaccctg gaagcggagg agcagcttac    180

atccagaagt ttaaagggaa ggcaactctg accgccgaca agagctcctc tacagcccat    240

atggagctga gttcactgac tagcgaagat agcgccgtgt actattgtac ccgctggctg    300

cctatggact attggggaca ggggacttca gtgacagtga gttca                    345


<210> SEQ ID NO 116
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Lys Ala Ser Asp His Ile Asn Asn Trp Leu Ala
1               5                   10


<210> SEQ ID NO 117
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Gly Ala Thr Ser Leu Glu Thr
1               5


<210> SEQ ID NO 118
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Gln Gln Tyr Leu Ile Thr Pro Tyr Thr
1               5


<210> SEQ ID NO 119
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Ser Asp His Ile Asn Asn Trp
1               5


<210> SEQ ID NO 120
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Gly Ala Thr
1
```

<210> SEQ ID NO 121
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 121

```
Tyr Leu Ile Thr Pro Tyr
1               5
```

<210> SEQ ID NO 122
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 122

```
Asp Ile Gln Met Thr Gln Ser Ser Ser Tyr Leu Ser Val Ser Leu Gly
1               5                   10                  15

Gly Arg Val Thr Ile Thr Cys Lys Ala Ser Asp His Ile Asn Asn Trp
            20                  25                  30

Leu Ala Trp Tyr Gln Gln Lys Pro Gly Asn Ala Pro Arg Leu Leu Ile
        35                  40                  45

Ser Gly Ala Thr Ser Leu Glu Thr Gly Val Pro Ser Arg Phe Ser Gly
    50                  55                  60

Ser Gly Ser Gly Lys Asp Tyr Thr Leu Ser Ile Thr Gly Leu Gln Thr
65                  70                  75                  80

Glu Asp Val Ala Thr Tyr Tyr Cys Gln Gln Tyr Leu Ile Thr Pro Tyr
                85                  90                  95

Thr Phe Gly Gly Gly Thr Lys Leu Glu Ile Lys
            100                 105
```

<210> SEQ ID NO 123
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 123

```
gatattcaga tgacccagag tagttcttac ctgagcgtgt ccctgggagg aagggtcacc     60

atcacatgca aggcaagcga ccacattaac aattggctgg cctggtacca gcagaaacca    120

ggaaacgcac ctcgactgct gatcagcgga gctacttccc tggagaccgg cgtgccctct    180

agattctctg gaagtggctc agggaaggac tatacactga gcattactgg cctgcagacc    240

gaagatgtcg ctacatacta ttgtcagcag tacctgatta caccctacac tttcggcggc    300

ggaactaaac tggagattaa g                                              321
```

<210> SEQ ID NO 124
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 124

```
Glu Phe Arg His Gly Leu Asn Asp Ile Phe
1               5                   10


<210> SEQ ID NO 125
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Glu Phe Arg His Gly Leu Asn Asp Ile Phe Glu
1               5                   10


<210> SEQ ID NO 126
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Glu Ala Gln Lys Ile Glu Trp His Glu Ser Gln Val Ser Asp Leu
1               5                   10                  15


<210> SEQ ID NO 127
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Ala Gln Lys Ile Glu Trp His Glu Ser Gln Val Ser Asp Leu
1               5                   10


<210> SEQ ID NO 128
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Leu Thr Gln Glu Gln Ala Asn Leu Thr His Gln Lys Lys Lys Leu Glu
1               5                   10                  15

Gly Gln Ile Ser Ala Arg Gln Gln Ala Glu Glu Ala Ser Gln Glu Ser
            20                  25                  30

Glu Asn Glu Leu Lys Glu
        35


<210> SEQ ID NO 129
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Leu Thr Gln Glu Gln Ala Asn Leu Thr His Gln Lys Lys Lys Leu Glu
1               5                   10                  15
```

```
Gly Gln Ile Ser Ala Arg Gln Gln Ala Glu Glu Ala Ser Gln Glu Ser
            20                  25                  30

Glu Asn Glu Leu Lys Glu Met Ile Glu Thr Leu
        35                  40


<210> SEQ ID NO 130
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Ala Ser Gln Glu Ser Glu Asn Glu Leu Lys Glu Met Ile Glu Thr Leu
1               5                   10                  15


<210> SEQ ID NO 131
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Asn Glu Leu Lys Glu Met Ile Glu Thr Leu
1               5                   10


<210> SEQ ID NO 132
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Phe Ser Ser Gly Ser Phe Asn Trp Glu Lys Ser Gln Glu Lys Cys
1               5                   10                  15


<210> SEQ ID NO 133
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Phe Ser Ser Gly Ser Phe Asn Trp Glu Lys Ser Gln Glu Lys Cys Leu
1               5                   10                  15

Ser Leu


<210> SEQ ID NO 134
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Ile Gln Gln Ala Ile Ser Tyr
1               5
```

```
<210> SEQ ID NO 135
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Ser Arg Arg Asn Pro Ser Tyr Pro Trp Leu Trp Glu Asp Gly Ser Pro
1               5                   10                  15

Leu Met Pro His Leu
            20


<210> SEQ ID NO 136
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Trp Glu Asp Gly Ser Pro Leu Met Pro His Leu
1               5                   10


<210> SEQ ID NO 137
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Phe Arg Val Arg Gly Ala Val Ser Gln Thr Tyr Pro Ser Gly Thr Cys
1               5                   10                  15

Ala Tyr Ile Gln Arg Gly Ala Val Tyr Ala Glu Asn Cys Ile Leu Ala
            20                  25                  30

Ala Phe Ser Ile Cys Gln Lys Lys Ala Asn Leu Arg Ala Gln
        35                  40                  45


<210> SEQ ID NO 138
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Tyr Ile Gln Arg Gly Ala Val Tyr Ala Glu Asn
1               5                   10


<210> SEQ ID NO 139
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Ile Gln Arg Gly Ala Val Tyr Ala Glu Asn
1               5                   10
```

```
<210> SEQ ID NO 140
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Ala Ala Phe Ser Ile Cys Gln Lys Lys Ala Asn Leu
1               5                   10


<210> SEQ ID NO 141
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Ala Ala Phe Ser Ile Cys Gln Lys Lys Ala Asn Leu Arg Ala Gln
1               5                   10                  15


<210> SEQ ID NO 142
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Phe Ser Ile Cys Gln Lys Lys Ala Asn Leu
1               5                   10


<210> SEQ ID NO 143
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Phe Ser Ile Cys Gln Lys Lys Ala Asn Leu Arg Ala Gln
1               5                   10


<210> SEQ ID NO 144
<211> LENGTH: 15
<212> TYPE: PRT
<213> ORGANISM: Homo sapiens

<400> SEQUENCE: 144

Gly Leu Asn Asp Ile Phe Glu Ala Gln Lys Ile Glu Trp His Glu
1               5                   10                  15


<210> SEQ ID NO 145
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 145

His His His His His His
```

```
1               5


<210> SEQ ID NO 146
<211> LENGTH: 232
<212> TYPE: PRT
<213> ORGANISM: Macaca fascicularis

<400> SEQUENCE: 146

Glu Phe Arg His Gly Leu Asn Asp Ile Phe Glu Ala Gln Lys Ile Glu
1               5                   10                  15

Trp His Glu Ser Gln Val Ser Asn Leu Leu Lys Gln Gln Gln Thr Asn
            20                  25                  30

Leu Thr His Gln Lys Asn Lys Leu Glu Gly Gln Ile Ser Ala Arg Gln
        35                  40                  45

Gln Ala Glu Glu Ala Ser Gln Glu Ser Gln Asn Glu Leu Lys Glu Met
    50                  55                  60

Ile Glu Thr Leu Ala Trp Lys Leu Asn Glu Lys Ser Lys Glu Gln Met
65                  70                  75                  80

Glu Leu His His Gln Asn Leu Asn Leu Gln Glu Thr Leu Lys Arg Val
                85                  90                  95

Ala Asn Cys Ser Ala Pro Cys Pro Gln Asp Trp Ile Trp His Glu Glu
            100                 105                 110

Asn Cys Tyr Leu Phe Ser Thr Gly Ser Phe Asn Trp Glu Lys Ser Gln
        115                 120                 125

Glu Lys Cys Leu Ser Leu Asp Ala Lys Leu Leu Lys Ile Asn Ser Thr
    130                 135                 140

Ala Asp Leu Asp Phe Ile Gln Gln Ala Ile Ser Tyr Ser Ser Phe Pro
145                 150                 155                 160

Phe Trp Met Gly Leu Ser Arg Arg Asn Pro Ser Tyr Pro Trp Leu Trp
                165                 170                 175

Glu Asp Gly Ser Pro Leu Met Pro His Leu Phe Arg Ile Arg Gly Ala
            180                 185                 190

Val Ser Gln Thr Tyr Pro Ser Gly Thr Cys Ala Tyr Ile Gln Arg Gly
        195                 200                 205

Ala Val Tyr Ala Glu Asn Cys Ile Leu Ala Ala Phe Ser Ile Cys Gln
    210                 215                 220

Lys Lys Ala Asn Leu Arg Ala Gln
225                 230


<210> SEQ ID NO 147
<211> LENGTH: 9
<212> TYPE: PRT
<213> ORGANISM: Artificial Sequence
<220> FEATURE:
<223> OTHER INFORMATION: Description of Artificial Sequence: Synthetic
      9xHis tag

<400> SEQUENCE: 147

His His His His His His His His His
1               5
```

METHODS OF TREATING CARDIOVASCULAR DISORDERS WITH LECTIN-LIKE OXIDIZED LDL RECEPTOR 1 ANTIBODIES

This application is a divisional of U.S. application Ser. No. 14/307,515, filed on Jun. 18, 2014, which claims the benefit of U.S. Provisional Application No. 61/837,776, filed on Jun. 21, 2013, each of which is hereby incorporated by reference in its entirety.

BACKGROUND OF THE INVENTION

Vascular disease remains one of the leading causes of morbidity and mortality worldwide. Drugs targeting conventional risk factors lower part of the vascular risk. However, experimental and clinical data suggest that other novel factors may explain the greater part of the risk for coronary, cerebral and peripheral arterial diseases and their clinical manifestations.

Dysregulated uptake of oxidatively modified low density lipoprotein (LDL) particles (oxLDL) by vascular cells mediated by scavenger receptors is considered to be a crucial step in atherogenesis. In addition to mediating the uptake of oxidized lipids, the scavenger receptors can mediate activation of pro-oxidant and pro-inflammatory signaling pathways which are involved in activation of endothelial cells and macrophages, and which lead to progression of atherosclerosis and plaque erosion/rupture as well as to microvascular dysfunction with impaired tissue perfusion and oxygen delivery/utilization, resulting in myocardial or lower limb ischemia.

The lectin-like oxidized low density lipoprotein receptor 1 (LOX-1) is a multifunctional scavenger receptor which is expressed on vascular endothelial cells, monocytes and macrophages, vascular smooth muscle cells, and platelets. LOX-1 binds oxLDL and other oxidized lipids, resulting in activation of NADPH oxidase and generation of reactive oxygen species including superoxide anion. Superoxide anion inactivates endothelial nitric oxide and activates MAP kinase and NF-κB. This in turn induces expression of inflammatory adhesion molecules, cytokines and chemokines, as well as matrix metalloproteinases and pro-apoptotic mediators.

The pro-inflammatory, pro-oxidant and pro-apoptotic consequences of oxLDL-LOX-1 mediated signaling in endothelial cells, smooth muscle cells, and macrophages are thought to play a key role in progression of atherosclerosis and plaque instability and may also play a role in impaired tissue perfusion and oxygen delivery, resulting in ischemia. The clinical consequences of advanced atherosclerosis and organ ischemia include: acute coronary syndromes, myocardial infarction, unstable angina, stroke, angina, claudication and critical limb ischemia. In addition, oxidative stress, vascular inflammation and resulting microvascular dysfunction are thought to contribute to diabetic vascular disease, including nephropathy and retinopathy.

While basal LOX-1 endothelial expression levels are relatively low under normal physiological conditions, vascular LOX-1 expression is upregulated in conditions associated with vascular disease. Endothelial LOX-1 levels have been shown to be increased by oxidative stress, pro-inflammatory cytokines, C-reactive protein (CRP) and angiotensin II. LOX-1 is also upregulated in the endothelium of atherosclerotic and diabetic animals and in monocytes/macrophages isolated from patients with vascular disease. Hyperglycemia, advanced glycated endproducts and atherogenic lipoproteins also upregulate LOX-1 expression, providing a specific molecular mechanistic link between diabetes and vascular complications.

The upregulation of LOX-1 by cytokines and CRP also suggests a link between conventional vascular risk factors and accelerated vascular disease in high risk patients and diabetics. Both CRP and soluble LOX-1 are elevated in patients with acute coronary syndromes. In vitro data have shown that anti-LOX-1 antibodies prevent CRP mediated monocyte adhesion to human aortic endothelial cells, further supporting a role for LOX-1 as an adhesion molecule relevant to vascular inflammation (Li et al., Circulation Research 2004, 95: 877-883).

Increased expression of LOX-1 coupled to elevated levels of oxLDL and other oxidized lipoproteins induces endothelial dysfunction, in part, by activating NADPH oxidase and generation of reactive oxygen species. Experimentally, oxidant stress induced endothelial dysfunction can be reversed with a neutralizing anti-LOX-1 antibody in ApoE-knockout mice (Xu et al., Arteriosclerosis, Thrombosis and Vascular Biology 2007, 27:871-877). In this study, anti-LOX-1 antibody increased both bioavailable nitric oxide and eNOS protein expression.

Experimental in vivo data indicate that overexpression of vascular and macrophage LOX-1 in the presence of oxidized lipids contributes to atherosclerosis and microvascular dysfunction by activating pro-oxidant and pro-inflammatory signaling pathways. Thus, inhibition of LOX-1 is expected to prevent development and progression of atherosclerosis and its acute complications such as acute coronary syndromes, myocardial infarction and unstable angina. In addition LOX-1 inhibition is also expected to ameliorate microvascular dysfunction, preventing clinical manifestations of tissue ischemic such as chronic angina, refractory angina, claudication and critical limb ischemia.

LOX-1 inhibition is useful not only in the treatment and prevention of atherosclerotic vascular disease, but also in treatment of other pathologic conditions characterized by oxidative stress and inflammation such as rheumatoid arthritis, various forms of vasculitis, uveitis, age related macular degeneration, and prevention of cardiovascular events in autoimmune diseases (e.g. lupus erythematosis, psoriasis).

In summary, experimental and clinical data suggest that LOX-1 may be the critical oxidized lipid receptor linking oxidative stress, inflammation and vascular disease. The anti-LOX-1 antibodies and antigen binding fragments described in this invention inhibit binding of oxLDL and other oxidized lipids/lipoproteins to LOX-1, preventing activation of LOX-1, thereby reducing vascular oxidative stress and inflammation. These antibodies are expected to prevent and ameliorate the acute and chronic manifestations of vascular disease and to prevent and ameliorate other diseases characterized by oxidative stress and inflammation.

SUMMARY OF THE INVENTION

The present invention relates to monoclonal antibodies binding to human lectin-like oxidized LDL (low density lipoprotein) receptor 1 (hereinafter, sometimes referred to as "LOX-1"), and pharmaceutical compositions and methods of treatment comprising the same.

The isolated anti-LOX-1 antibodies, or antigen binding fragments, described herein bind LOX-1, with an equilibrium dissociation constant ($K_D$) of less than or equal to 100 pM. For example, the isolated antibodies or antigen binding fragments described herein may bind to human LOX-1 with a $K_D$ of less than or equal to 100 pM, less than or equal to 50 pM, less than or equal to 45 pM, less than or equal to 40 pM, less than or equal to 35 pM. More specifically, the isolated antibodies or antigen binding fragments described herein may also bind human LOX-1 with a $K_D$ of less than or equal to 34 pM, as measured by BIACORE™, or less than or equal to 4 pM, as measured by solution equilibrium titration assay (SET); and may also bind cynomolgus monkey LOX-1 with a $K_D$ of less than or equal to 53 pM, as measured by BIACORE™, or less than or equal to 4 pM, as measured by SET.

The present invention relates to an isolated antibody, or antigen binding fragments thereof, that binds to human and cynomolgus monkey LOX-1. The invention also relates to an isolated antibody, or antigen binding fragments thereof, that binds to the LOX-1 C-terminal lectin-like domain (oxLDL binding domain). The invention also relates to an isolated antibody, or antigen binding fragments thereof, that binds an epitope comprising amino acid residues 228-246 from human LOX-1 (FRVRGAVSQTYPSGTCAYI; SEQ ID NO:3). The present invention also includes an isolated antibody, or antigen binding fragments thereof, that binds an epitope on human LOX-1 comprising amino acid residues Arg229 and Arg231 of human LOX-1 (SEQ ID NO:1).

The present invention also relates to an isolated antibody, or antigen binding fragments thereof, that binds LOX-1 and further competes for binding with an antibody as described in Table 1. The present invention also further relates to an isolated antibody, or antigen binding fragments thereof, that binds the same epitope as an antibody as described in Table 1.

The binding affinity of isolated antibodies and antigen binding fragments described herein can be determined by solution equilibrium titration (SET). Methods for SET are known in the art and are described in further detail below. Alternatively, binding affinity of the isolated antibodies, or fragments, described herein can be determined by BIACORE™ assay. Methods for BIACORE™ kinetic assays are known in the art and are described in further detail below.

The isolated anti-LOX-1 antibodies and antigen binding fragments described herein can be used to inhibit LOX-1 binding to oxLDL (also known as modified LDL).

The isolated anti-LOX-1 antibodies and antigen binding fragments described herein can be used to inhibit LOX-1 binding to multiple forms of modified LDL (low density lipoproteins) with an $IC_{50}$ of less than or equal to 100 nM, less than or equal to 50 nM, less than or equal to 35 nM, less than or equal to 25 nM, less than or equal to 10 nM, or less than or equal to 5.2 nM. More specifically, an isolated antibody or antigen binding fragments thereof as described herein can inhibit LOX-1 binding to copper sulfate oxidatively modified LDL (ox-LDLs) with an $IC_{50}$ of less than or equal to 100 nM, less than or equal to 50 nM, less than or equal to 35 nM, less than or equal to 25 nM, less than or equal to 10 nM, or less than or equal to 5.2 nM. More specifically, an isolated antibody or antigen binding fragments thereof as described herein can inhibit LOX-1 binding to malondialdehyde modified LDL with an $IC_{50}$ of less than or equal to 100 nM, less than or equal to 50 nM, less than or equal to 35 nM, less than or equal to 25 nM, less than or equal to 20 nM, or less than or equal to 18 nM. More specifically, an isolated antibody or antigen binding fragments thereof as described herein can inhibit LOX-1 binding to hypochlorite modified LDL with an $IC_{50}$ of less than or equal to 100 nM, less than or equal to 50 nM, less than or equal to 35 nM, less than or equal to 25 nM, less than or equal to 10 nM, or less than or equal to 5 nM.

The isolated anti-LOX-1 antibodies, or antigen binding fragments thereof, may be used to reduce the expression of LOX-1 and/or NADPH oxidase (NADPH is the reduced form of NADP, or nicotinamide adenine dinucleotide phosphate).

The isolated anti-LOX-1 antibodies, or antigen binding fragments thereof, may be used to inhibit (e.g., block the induction of) oxidative stress, e.g., via inhibiting binding of oxLDLs to LOX-1. The isolated anti-LOX-1 antibodies, or antigen binding fragments thereof, may be used to block oxLDL-stimulated reactive oxygen species (ROS) production. Vascular oxidative stress, which the isolated antibodies, or antigen binding fragments thereof, may be used to prevent, treat, or ameliorate, causes myocardial ischemic by inducing vasoconstriction, impairing vasodilation, and increasing oxygen demand.

The isolated anti-LOX-1 antibodies, or antigen binding fragments thereof, may be used to restore endothelial nitric oxide synthase (eNOS) levels to a healthy, homeostatic state. Endothelial NOS is a nitric oxide synthase that generates nitric oxide (NO) in blood vessels and is involved in regulating vascular tone by inhibiting smooth muscle contraction and platelet aggregation; its downregulation is associated with LOX-1-related endothelial cell dysfunction.

The isolated anti-LOX-1 antibodies, or antigen binding fragments thereof, as described herein can be monoclonal antibodies, human or humanized antibodies, chimeric antibodies, single chain antibodies, Fab fragments, Fv fragments, F(ab')2 fragments, or scFv fragments, and/or IgG isotypes.

The isolated anti-LOX-1 antibodies, or antigen binding fragments thereof, as described herein can also include a framework in which an amino acid has been substituted into the antibody framework from the respective human VH or VL germline sequences.

Another aspect of the invention includes an isolated antibody or antigen binding fragments thereof having the full heavy and light chain sequences of Fabs described in Table 1. More specifically, the isolated antibody or antigen binding fragments thereof can have the heavy and light chain sequences of Fab FF1, FF3, FF4, FF5, and FF6.

A further aspect of the invention includes an isolated antibody or antigen binding fragments thereof having the heavy and light chain variable domain sequences of Fabs described in Table 1. More specifically, the isolated antibody or antigen binding fragment thereof can have the heavy and light chain variable domain sequence of Fab FF1, FF3, FF4, FF5, and FF6.

The invention also relates to an isolated antibody or antigen binding fragments thereof that includes a heavy chain CDR1 selected from the group consisting of SEQ ID NOs: 8, 28, 48, 68, and 88; a heavy chain CDR2 selected from the group consisting of SEQ ID NOs: 9, 29, 49, 69, and 89; and a heavy chain CDR3 selected from the group consisting of SEQ ID NOs: 10, 30, 50, 70, and 90, wherein the isolated antibody or antigen binding fragments thereof binds to human LOX-1. In another aspect, such isolated antibody or antigen binding fragments thereof further includes a light chain CDR1 selected from the group consisting of SEQ ID NOs: 18, 38, 58, 78, and 98; a light chain CDR2 selected from the group consisting of SEQ ID NOs: 19, 39, 59, 79, and 99; and a light chain CDR3 selected from the group consisting of SEQ ID NOs: 20, 40, 60, 80, and 100.

The invention also relates to an isolated antibody or antigen binding fragments thereof that includes a light chain CDR1 selected from the group consisting of SEQ ID NOs:

18, 38, 58, 78, and 98; a light chain CDR2 selected from the group consisting of SEQ ID NOs: 19, 39, 59, 79, and 99; and a light chain CDR3 selected from the group consisting of SEQ ID NOs: 20, 40, 60, 80, and 100, wherein the isolated antibody or antigen binding fragments thereof binds to human LOX-1.

The invention also relates to an isolated antibody or antigen binding fragments thereof that binds LOX-1 having HCDR1, HCDR2, and HCDR3 and LCDR1, LCDR2, and LCDR3, wherein HCDR1, HCDR2, and HCDR3 comprises SEQ ID NOs: 8, 9, and 10, and LCDR1, LCDR2, LCDR3 comprises SEQ ID NOs: 18, 19, and 20; or HCDR1, HCDR2, and HCDR3 comprises SEQ ID NOs: 28, 29, and 30, and LCDR1, LCDR2, LCDR3 comprises SEQ ID NOs: 38, 39, and 40; or HCDR1, HCDR2, and HCDR3 comprises SEQ ID NOs: 48, 49, and 50, and LCDR1, LCDR2, LCDR3 comprises SEQ ID NOs: 58, 59, and 60; or HCDR1, HCDR2, and HCDR3 comprises SEQ ID NOs: 68, 69, and 70, and LCDR1, LCDR2, LCDR3 comprises SEQ ID NOs: 78, 79, and 80; or HCDR1, HCDR2, and HCDR3 comprises SEQ ID NOs: 88, 89, and 90, and LCDR1, LCDR2, LCDR3 comprises SEQ ID NOs: 98, 99, and 100.

The invention also relates to an antibody or antigen binding fragment having HCDR1, HCDR2, and HCDR3 of the variable heavy chain of SEQ ID NOs: 14, 34, 54, 74, or 94, and the LCDR1, LCDR2 and LCDR3 of the variable light chain of SEQ ID NOs: 24, 44, 64, 84, or 104, as defined by Chothia. In another aspect of the invention the antibody or antigen binding fragment may have the HCDR1, HCDR2, and HCDR3 of the heavy chain variable domain sequence of SEQ ID NOs: 14, 34, 54, 74, or 94, and the LCDR1, LCDR2 and LCDR3 of the light chain variable domain sequence of SEQ ID NOs: 24, 44, 64, 84, or 104, as defined by Kabat.

In one aspect of the inventions the isolated antibody or antigen binding fragments thereof includes a heavy chain variable domain sequence selected from the group consisting of SEQ ID NOs: 14, 34, 54, 74, and 94. The isolated antibody or antigen binding fragment further can comprise a light chain variable domain sequence wherein the heavy chain variable domain and light chain variable domain combine to form and antigen binding site for LOX-1. In particular the light chain variable domain sequence can be selected from SEQ ID NOs: 24, 44, 64, 84, and 104 wherein said isolated antibody or antigen binding fragments thereof binds LOX-1.

The invention also relates to an isolated antibody or antigen binding fragments thereof that includes a light chain variable domain sequence selected from the group consisting of SEQ ID NOs: 24, 44, 64, 84, and 104, wherein said isolated antibody or antigen binding fragments thereof binds to human LOX-1. The isolated antibody or antigen binding fragment may further comprise a heavy chain variable domain sequence wherein the light chain variable domain and heavy chain variable domain combine to form and antigen binding site for LOX-1.

In particular, the isolated antibody or antigen binding fragments thereof that binds LOX-1, may have heavy and light chain variable domains comprising the sequences of SEQ ID NOs: 14 and 24; 34 and 44; 54 and 64; 74 and 84; or 94 and 104, respectively.

The invention further relates to an isolated antibody or antigen binding fragments thereof, that includes a heavy chain variable domain having at least 90% sequence identity to a sequence selected from the group consisting of SEQ ID NOs: 14, 34, 54, 74, and 94, wherein said antibody binds to LOX-1. In one aspect, the isolated antibody or antigen binding fragments thereof also includes a light chain variable domain having at least 90% sequence identity to a sequence selected from the group consisting of SEQ ID NOs: 24, 44, 64, 84, and 104. In a further aspect of the invention, the isolated antibody or antigen binding fragment has an HCDR1, HCDR2, HCDR3, LCDR1, LCDR2 and LCDR3 as defined by Kabat and as described in Table 1.

The invention also relates to an isolated antibody or antigen binding fragments thereof, having a light chain variable domain having at least 90% sequence identity to a sequence selected from the group consisting of SEQ ID NOs: 24, 44, 64, 84, and 104, wherein said antibody binds LOX-1.

In another aspect of the invention, the isolated antibody, or antigen binding fragments thereof, that binds to LOX-1 may have a heavy chain comprising the sequence of SEQ ID NOs: 16, 36, 56, 76, or 96. The isolated antibody can also includes a light chain that can combine with the heavy chain to form an antigen binding site to human LOX-1. In particular, the light chain may have a sequence comprising SEQ ID NOs: 26, 46, 66, 86, or 106. In particular, the isolated antibody or antigen binding fragments thereof that binds LOX-1, may have a heavy chain and a light chain comprising the sequences of SEQ ID NOs: 16 and 26; 36 and 46; 56 and 66; 76 and 86; or 96 and 106, respectively.

The invention still further relates to an isolated antibody or antigen binding fragments thereof that includes a heavy chain having at least 90% sequence identity to a sequence selected from the group consisting of SEQ ID NOs: 16, 36, 56, 76, or 96, wherein said antibody binds to LOX-1. In one aspect, the isolated antibody or antigen binding fragments thereof also includes a light chain having at least 90% sequence identity to a sequence selected from the group consisting of SEQ ID NOs: 26, 46, 66, 86, or 106.

The invention still further relates to an isolated antibody or antigen binding fragments thereof that includes a light chain having at least 90% sequence identity to a sequence selected from the group consisting of SEQ ID NOs: 26, 46, 66, 86, or 106, wherein said antibody binds LOX-1.

The invention also relates to compositions comprising the isolated antibody, or antigen binding fragments thereof, described herein. As well as, antibody compositions in combination with a pharmaceutically acceptable carrier. Specifically, the invention further includes pharmaceutical compositions comprising an antibody or antigen binding fragments thereof of Table 1, such as, for example antibody FF1, FF3, FF4, FF5, and FF6. The invention also relates to pharmaceutical compositions comprising a combination of two or more of the isolated antibodies or antigen binding fragments thereof of Table 1.

The invention also relates to an isolated nucleic acid sequence encoding the variable heavy chain having a sequence selected from SEQ ID NOs: 14, 34, 54, 74, and 94. In particular the nucleic acid has a sequence at least 90% sequence identity to a sequence selected from the group consisting of SEQ ID NOs: 15, 35, 55, 75, and 95. In a further aspect of the invention the sequence is SEQ ID NOs: 15, 35, 55, 75, and 95.

The invention also relates to an isolated nucleic acid sequence encoding the variable light chain having a sequence selected from SEQ ID NOs: 25, 45, 65, 85, and 105. In particular the nucleic acid has a sequence at least 90% sequence identity to a sequence selected from the group consisting of SEQ ID NOs: 25, 45, 65, 85, and 105. In a further aspect of the invention the sequence is SEQ ID NOs: 25, 45, 65, 85, and 105.

The invention also relates to an isolated nucleic acid comprising a sequence encoding a polypeptide that includes a light chain variable domain having at least 90% sequence identity to a sequence selected from the group consisting of SEQ ID NOs: 25, 45, 65, 85, and 105.

The invention also relates to a vector that includes one or more of the nucleic acid molecules described herein.

The invention also relates to an isolated host cell that includes a recombinant DNA sequence encoding a heavy chain of the antibody described above, and a second recombinant DNA sequence encoding a light chain of the antibody described above, wherein said DNA sequences are operably linked to a promoter and are capable of being expressed in the host cell. It is contemplated that the antibody can be a human monoclonal antibody. It is also contemplated that the host cell is a non-human mammalian cell.

The invention also relates to a method of reducing LOX-1 expression, and/or NADPH oxidase expression, wherein the method includes the step of contacting a cell with an effective amount of a composition comprising the isolated antibody or antigen binding fragments thereof described herein.

The invention also relates to a method of inhibiting the binding of oxidized LDL (oxLDL) to a human oxidized LDL receptor (LOX-1) or to inhibit the human oxidized LDL receptor-mediated incorporation of oxidized LDL into cells, wherein the method includes the step of contacting a cell with an effective amount of a composition comprising the isolated antibody or antigen binding fragments thereof described herein.

It is contemplated that the cell is a human cell. It is further contemplated that the cell is in a subject. In one embodiment, it is contemplated that the cell is an endothelial cell. In other embodiments, the cell may be one or more of macrophages, monocytes, dendritic cells, vascular smooth muscle cells (SMC), chondrocytes, and cardiac myocytes. It is still further contemplated that the subject is human.

The invention also relates to a method of treating, improving, or preventing a LOX-1-associated disorder in a subject, wherein the method includes the step of administering to the subject an effective amount of a composition comprising the antibody or antigen binding fragments thereof described herein. In one aspect, the LOX-1-associated disorder is associated with claudication (e.g., intermittent claudication, Rutherford Class II/III Claudication). In one aspect, the LOX-1-associated disorder is associated with angina (e.g., refractory angina). It is contemplated that the subject is human.

Any of the foregoing isolated antibodies or antigen binding fragments thereof may be a monoclonal antibody or antigen binding fragments thereof.

Definitions

Unless defined otherwise, all technical and scientific terms used herein have the same meaning as commonly understood by those of ordinary skill in the art to which this invention pertains.

The term "LOX-1 protein" or "LOX-1 antigen" or "LOX-1" or "Lox1" are used interchangeably, and refers to the Lectin-Like Oxidized LDL Receptor1 (LOX-1) protein in different species. For example, human LOX-1 has the sequence as set out in Table 1 (SEQ ID NO:1), and has been described in previous reports and literature (Nature, Vol. 386, p. 73-77, 1997; Genomics, Vol. 54, No. 2, p. 191-199, 1998; Biochem. J., Vol. 339, Part 1, P. 177-184, 1999; Genbank Accession No. NP 002534). It is a class E scavenger receptor that mediates the uptake of oxLDL by vascular cells and oxLDL signaling in vascular cells, and as such, is a mediator of the toxic effects of oxLDL. LOX-1 is expressed on the surface of vascular endothelial cells and has been implicated in the accumulation of monocytes and macrophages on vascular endothelial cells.

In addition, in the context of this invention, the term "LOX-1" includes mutants of the natural human oxidized-LDL receptor, which have substantially the same amino acid sequence as that of the native primary structure (amino acid sequence) described in the above-mentioned reports. Herein, the term "mutants of the natural human oxidized-LDL receptor having substantially the same amino acid sequence" refers to such mutant proteins.

Multiple forms of modified LDL formed in vitro and/or in vivo have been shown to bind to LOX-1. As used herein, the term "modified LDL" and "oxidized LDL" (and "oxLDL") are used interchangeably to describe low density lipoproteins which are oxidized by cells, such as vascular endothelial cells, in combination with various chemical and physical factors (e.g., heat). LDL is oxidized, for example, within the vascular wall under atherogenic conditions to form oxLDL. The term "modified LDL" can encompass the following: oxidized LDL, copper sulfate oxidatively modified LDL, acetyl LDL, chlorinated LDL (e.g., LDL modified via a chemical chlorination reaction), myeloperoxidase modified LDL, hypochlorite modified LDL, succinyl LDL, and malondialdehyde modified LDL (i.e., LDL modified via reaction with malondialdehyde, which is produced in vivo as a consequence of oxidative stress).

The term "antibody" as used herein means a whole antibody and any antigen binding fragment (i.e., "antigen-binding portion") or single chain thereof. A whole antibody is a glycoprotein comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen binding portion" or "antigen binding fragment" of an antibody, as used herein, refers to one or more fragments of an intact antibody that retain the ability to specifically bind to a given antigen (e.g., human oxidized LDL receptor (LOX-1)). Antigen binding functions of an antibody can be performed by fragments of an intact antibody. Examples of binding fragments encompassed within the term antigen binding portion or antigen binding fragment of an antibody include a Fab fragment, a monovalent fragment consisting of the VL, VH, CL and CH1 domains; a $F(ab)_2$ fragment, a bivalent fragment comprising two Fab fragments linked by a disulfide bridge at the hinge region; an Fd fragment consisting of the VH and CH1 domains; an Fv fragment consisting of the VL and VH domains of a single arm of an antibody; a single domain antibody (dAb) fragment (Ward et al., 1989 Nature 341:544-546), which consists of a VH domain or a VL domain; and an isolated complementarity determining region (CDR).

Furthermore, although the two domains of the Fv fragment, VL and VH, are coded for by separate genes, they can be joined, using recombinant methods, by an artificial peptide linker that enables them to be made as a single protein chain in which the VL and VH regions pair to form monovalent molecules (known as single chain Fv (scFv); see, e.g., Bird et al., 1988 Science 242:423-426; and Huston et al., 1988 Proc. Natl. Acad. Sci. 85:5879-5883). Such single chain antibodies include one or more antigen binding portions or fragments of an antibody. These antibody fragments are obtained using conventional techniques known to those of skill in the art, and the fragments are screened for utility in the same manner as are intact antibodies.

Antigen binding fragments can also be incorporated into single domain antibodies, maxibodies, minibodies, intrabodies, diabodies, triabodies, tetrabodies, v-NAR and bis-scFv (see, e.g., Hollinger and Hudson, 2005, Nature Biotechnology, 23, 9, 1126-1136). Antigen binding portions of antibodies can be grafted into scaffolds based on polypeptides such as Fibronectin type III (Fn3) (see U.S. Pat. No. 6,703, 199, which describes fibronectin polypeptide monobodies).

Antigen binding fragments can be incorporated into single chain molecules comprising a pair of tandem Fv segments (VH-CH1-VH-CH1) which, together with complementary light chain polypeptides, form a pair of antigen binding regions (Zapata et al., 1995 Protein Eng. 8(10):1057-1062; and U.S. Pat. No. 5,641,870).

As used herein, the term "affinity" refers to the strength of interaction between antibody and antigen at single antigenic sites. Within each antigenic site, the variable region of the antibody "arm" interacts through weak non-covalent forces with antigen at numerous sites; the more interactions, the stronger the affinity. As used herein, the term "high affinity" for an antibody or antigen binding fragments thereof (e.g., a Fab fragment) generally refers to an antibody, or antigen binding fragment, having a KD of $10^{-9}$M or less.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an alpha carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The term "binding specificity" as used herein refers to the ability of an individual antibody combining site to react with only one antigenic determinant.

The phrase "specifically (or selectively) binds" to an antibody (e.g., a LOX-1-binding antibody) refers to a binding reaction that is determinative of the presence of a cognate antigen (e.g., a human LOX-1 or cynomolgus LOX-1) in a heterogeneous population of proteins and other biologics. The phrases "an antibody recognizing an antigen" and "an antibody specific for an antigen" are used interchangeably herein with the term "an antibody which binds specifically to an antigen".

The term "LOX-1 mediated" refers to the fact that the LOX-1 receptor mediates the cellular response upon binding of a LOX-1 ligand, e.g., oxLDL, to LOX-1 on the cell surface, which then triggers the cell to increase production of certain pro-inflammatory molecules. The term "pro-inflammatory gene" refers to a gene encoding any molecule, such as, but not limited to, a cytokine, a chemokine, or a cell-adhesion molecule, which plays a role in an inflammatory process. Exemplary "pro-inflammatory" genes include, but are not limited to, interleukin-8 (IL-8), intercellular adhesion molecule-1 (ICAM-1), vascular cell adhesion molecule-1 (VCAM-1) and monocyte chemotactic protein-1 (MCP-1).

A "LOX-1-associated disorder," "LOX-1-associated condition," "disease or condition associated with elevated levels of LOX-1," or similar terms as used herein, refer to any number of conditions or diseases in which the LOX-1 protein levels are aberrantly high and/or in which a reduction of LOX-1 protein levels is sought. These conditions include but are not limited to cardiovascular disorders, endothelial cell dysfunction, endothelial cell disorders, atherosclerosis, arteriosclerosis, hypertension, hyperlipidemia, hypercholesterolemia, diabetes mellitus, nitric oxide deficiency, myocardial infarction, vascular oxidative stress, myocardial ischemia, ischemia-reperfusion, sepsis, diabetic nephropathy, renal disease, cardiomyopathy, heart failure, peripheral artery disease, coronary heart disease, claudication (e.g., intermittent claudication, Rutherford Class II/III Claudication), peripheral artery disease (PAD), angina (e.g., refractory angina), coronary artery disease (CAD) (e.g., due to atherosclerosis of the arteries feeding the heart), stroke, and abnormal endothelium-dependent vasodilation.

"Endothelial cell dysfunction," as used herein, means the inability of an endothelial cell to maintain its normal function. The endothelium plays a critical role in regulating vascular smooth tone and growth, vascular permeability, the inflammatory response, coagulation, and platelet adhesion. Non-limiting examples of endothelial cell function include maintaining balanced vascular tone, inhibiting thrombosis, inhibiting pro-inflammatory processes, maintaining vascular integrity (e.g., non-leakiness of the vasculature), and maintaining an anti-proliferative state in both the endothelium and smooth muscle cells. Common conditions and risk factors predisposing to atherosclerosis, such as dyslipidemia, hypertension, diabetes, and smoking are all associated with endothelial dysfunction, which promotes the development, progression, and complications of atherosclerosis. Endothelial dysfunction has generally been assessed as impaired endothelium-dependent vasodilation. This assumes that endothelium-dependent vasodilation is a surrogate marker for other important endothelial functions. The basis for this assumption is the observation that endothelium-derived nitric oxide, synthesized by the endothelial NO synthase (eNOS) from L-arginine, mediates endothelium-dependent vasodilation and other endothelial vasculoprotective functions. A growing clinical database suggests that endothelial dysfunction (impaired endothelial dependent vasodilation) is closely associated with major adverse cardiovascular events including myocardial ischemia and infarction, acute coronary syndromes, claudication and critical limb ischemic, transient ischemic attacks and stroke.

Accumulating experimental data also suggests that endothelial and endocardial impaired eNOS-derived NO availability not only may lead to abnormal left ventricular remodeling and dysfunction contributing to development and progression of heart failure.

An "endothelial cell disorder," as used herein, is any disorder that is characterized by endothelial cell dysfunction. Non-limiting examples of diseases or disorders that are characterized by endothelial cell dysfunction include angiogenic disorders such as cancers which require neovascularization to support tumor growth, infectious diseases, autoimmune disorders, vascular malformations, DiGeorge syndrome, HHT, cavernous hemangioma, transplant arteriopathy, vascular access stenosis associated with hemodialysis, vasculitis, vasculitidis, vascular inflammatory disorders, atherosclerosis, obesity, psoriasis, warts, allergic dermatitis, scar keloids, pyogenic granulomas, blistering disease, Kaposi sarcoma, persistent hyperplastic vitreous syndrome, retinopathy of prematurity, choroidal neovascularization, macular degeneration, diabetic retinopathy, ocular neovascularization, primary pulmonary hypertension, asthma, nasal polyps, inflammatory bowel and periodontal disease, ascites, peritoneal adhesions, contraception, endometriosis, uterine bleeding, ovarian cysts, ovarian hyperstimulation, arthritis, rheumatoid arthritis, chronic articular rheumatism, synovitis, osteoarthritis, osteomyelitis, osteophyte formation, sepsis, and vascular leak. Endothelial cell dysfunction can be determined using assays known in the art including detecting the increased expression of endothelial adhesion molecules or decreased expression or biological activity of nitric oxide synthase (eNOS).

"Claudication," as used herein, includes severe claudication and other like terms, and describes a mobility impairment and high unmet medical need. Claudication is a condition characterized by lower extremity ischemia, causing muscle fatigue, pain on exertion relieved by rest, limited mobility, and reduced quality of life, and is caused by atherosclerosis and abnormal (e.g., impaired) endothelium-dependent vasodilation. Its prevalence in the US is 8-12 million patients. Among patients with intermittent claudication, 7% will undergo lower extremity bypass surgery, 4% will require major amputations, and 16% will develop worsening claudication. Cardiovascular events, such as myocardial infarction and stroke, occur in 20% of severe claudication sufferers over 5 years. The current therapy is surgical, and treatment through less invasive means, such as the administration of the anti-LOX-1 antibodies of the invention, would represent an enormous therapeutic breakthrough.

"Refractory angina," as used herein, is a condition marked by chest pain due to ischemia of the heart muscle, generally due to obstruction or spasm of the coronary arteries (e.g., from coronary artery disease), with debilitating symptoms, very limited physical activity and poor quality of life. The 1-1.8 million patients refractory angina sufferers in the US experience increased cardiovascular mortality at a rate of 10% per year; at least 100,000 new refractory angina cases arise per year.

The term "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. For example, a mouse antibody can be modified by replacing its constant region with the constant region from a human immunoglobulin. Due to the replacement with a human constant region, the chimeric antibody can retain its specificity in recognizing the antigen while having reduced antigenicity in human as compared to the original mouse antibody.

The term "conservatively modified variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

For polypeptide sequences, "conservatively modified variants" include individual substitutions, deletions or additions to a polypeptide sequence which result in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine Methionine (M) (see, e.g., Creighton, Proteins (1984)). In some embodiments, the term "conservative sequence modifications" are used to refer to amino acid modifications that do not significantly affect or alter the binding characteristics of the antibody containing the amino acid sequence.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

The term "human antibody", as used herein, is intended to include antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences. The human antibodies of the invention may include amino acid residues not encoded by human sequences (e.g., mutations introduced by random or site-specific mutagenesis in vitro or by somatic mutation in vivo).

The term "human monoclonal antibody" refers to antibodies displaying a single binding specificity which have variable regions in which both the framework and CDR regions are derived from human sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

A "humanized" antibody is an antibody that retains the reactivity of a non-human antibody while being less immunogenic in humans. This can be achieved, for instance, by retaining the non-human CDR regions and replacing the remaining parts of the antibody with their human counterparts (i.e., the constant region as well as the framework portions of the variable region). See, e.g., Morrison et al., Proc. Natl. Acad. Sci. USA, 81:6851-6855, 1984; Morrison and Oi, Adv. Immunol., 44:65-92, 1988; Verhoeyen et al., Science, 239:1534-1536, 1988; Padlan, Malec. Immun., 28:489-498, 1991; and Padlan, Malec. Immun., 31:169-217, 1994. Other examples of human engineering technology include, but are not limited to Xoma technology disclosed in U.S. Pat. No. 5,766,886.

The terms "identical" or percent "identity," in the context of two or more nucleic acids or polypeptide sequences, refer to two or more sequences or subsequences that are the same. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) Adv. Appl. Math. 2:482c, by the homology alignment algorithm of Needleman and Wunsch, J. Mol. Biol. 48:443, 1970, by the search for similarity method of Pearson and Lipman, Proc. Nat'l. Acad. Sci. USA 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Brent et al., Current Protocols in Molecular Biology, John Wiley & Sons, Inc. (Ringbou ed., 2003)).

Two examples of algorithms that are suitable for determining percent sequence identity and sequence similarity are the BLAST and BLAST 2.0 algorithms, which are described in Altschul et al., Nuc. Acids Res. 25:3389-3402, 1977; and Altschul et al., J. Mol. Biol. 215:403-410, 1990, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are hatted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (w) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff, Proc. Natl. Acad. Sci. USA 89:10915, 1989) alignments (B) of 50, expectation (E) of 10, M=5, N=−4, and a comparison of both strands.

The BLAST algorithm also performs a statistical analysis of the similarity between two sequences (see, e.g., Karlin and Altschul, Proc. Natl. Acad. Sci. USA 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The percent identity between two amino acid sequences can also be determined using the algorithm of E. Meyers and W. Miller (Comput. Appl. Biosci., 4:11-17, 1988) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol, Biol. 48:444-453, 1970) algorithm which has been incorporated into the GAP program in the GCG software package (available on the world wide web at gcg.com), using either a Blossom 62 matrix or a PAM250 matrix, and a gap weight of 16, 14, 12, 10, 8, 6, or 4 and a length weight of 1, 2, 3, 4, 5, or 6.

Other than percentage of sequence identity noted above, another indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "isolated antibody" refers to an antibody that is substantially free of other antibodies having different antigenic specificities (e.g., an isolated antibody that specifically binds LOX-1 is substantially free of antibodies that specifically bind antigens other than LOX-1). An isolated antibody that specifically binds LOX-1 may, however, have cross-reactivity to other antigens. Moreover, an isolated antibody may be substantially free of other cellular material and/or chemicals.

The term "isotype" refers to the antibody class (e.g., IgM, IgE, IgG such as IgG1 or IgG4) that is provided by the heavy chain constant region genes. Isotype also includes modified versions of one of these classes, where modifications have been made to alter the Fc function, for example, to enhance or reduce effector functions or binding to Fc receptors.

The term "$k_{assoc}$" or "$k_a$", as used herein, is intended to refer to the association rate of a particular antibody-antigen interaction, whereas the term "$k_{dis}$" or "$k_d$," as used herein, is intended to refer to the dissociation rate of a particular antibody-antigen interaction. The term "$K_D$", as used herein, is intended to refer to the dissociation constant, which is obtained from the ratio of $k_d$ to $k_a$ (i.e. $k_d/k_a$) and is expressed as a molar concentration (M). $K_D$ values for antibodies can be determined using methods well established in the art. Methods for determining the $K_D$ of an antibody include measuring surface plasmon resonance using a biosensor system such as a BIACORE™ system, or measuring affinity in solution by solution equilibrium titration (SET).

The terms "monoclonal antibody" or "monoclonal antibody composition" as used herein refer to a preparation of antibody molecules of single molecular composition. A monoclonal antibody composition displays a single binding specificity and affinity for a particular epitope.

The term "nucleic acid" is used herein interchangeably with the term "polynucleotide" and refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, as detailed below, degenerate codon substitutions may be achieved by generating sequences in which the third position of one or more selected (or all) codons is substituted with mixed-base and/or deoxyinosine residues (Batzer et al., Nucleic Acid Res. 19:5081, 1991; Ohtsuka et al., J. Biol. Chem. 260:2605-2608, 1985; and Rossolini et al., Mol. Cell. Probes 8:91-98, 1994).

The term "operably linked" refers to a functional relationship between two or more polynucleotide (e.g., DNA) segments. Typically, the term refers to the functional relationship of a transcriptional regulatory sequence to a transcribed sequence. For example, a promoter or enhancer sequence is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, they are cis-acting. However, some transcriptional regulatory sequences, such as enhancers, need not be physically contiguous or located in close proximity to the coding sequences whose transcription they enhance.

As used herein, the term, "optimized" means that a nucleotide sequence has been altered to encode an amino acid sequence using codons that are preferred in the production cell or organism, generally a eukaryotic cell, for example, a cell of *Pichia*, a Chinese Hamster Ovary cell (CHO) or a human cell. The optimized nucleotide sequence is engineered to retain completely or as much as possible the amino acid sequence originally encoded by the starting nucleotide sequence, which is also known as the "parental" sequence. The optimized sequences herein have been engineered to have codons that are preferred in mammalian cells. However, optimized expression of these sequences in other eukaryotic cells or prokaryotic cells is also envisioned herein. The amino acid sequences encoded by optimized nucleotide sequences are also referred to as optimized.

The terms "polypeptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Unless otherwise indicated, a particular polypeptide sequence also implicitly encompasses conservatively modified variants thereof.

The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the human antibody, e.g., from a transfectoma, antibodies isolated from a recombinant, combinatorial human antibody library, and antibodies prepared, expressed, created or isolated by any other means that involve splicing of all or a portion of a human immunoglobulin gene, sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "recombinant host cell" (or simply "host cell") refers to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "subject" includes human and non-human animals. Non-human animals include all vertebrates (e.g.: mammals and non-mammals) such as, non-human primates (e.g.: cynomolgus monkey), sheep, dog, cow, chickens, amphibians, and reptiles. Except when noted, the terms "patient" or "subject" are used herein interchangeably. As used herein, the terms "cyno" or "cynomolgus" refer to the cynomolgus monkey (*Macaca fascicularis*).

As used herein, the term "treating" or "treatment" of any disease or disorder (e.g., LOX-1 associated disorder) refers in one embodiment, to ameliorating the disease or disorder (i.e., slowing or arresting or reducing the development of the disease or at least one of the clinical symptoms thereof). In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

"Prevention" as it relates to indications described herein, including, e.g., LOX-1 associated disorder, means any action that prevents or slows a worsening in e.g., LOX-1 associated disease parameters, as described below, in a patient at risk for said worsening.

The term "vector" is intended to refer to a polynucleotide molecule capable of transporting another polynucleotide to which it has been linked. One type of vector is a "plasmid", which refers to a circular double stranded DNA loop into which additional DNA segments may be ligated. Another type of vector is a viral vector, such as an adeno-associated viral vector (AAV, or AAV2), wherein additional DNA segments may be ligated into the viral genome. Certain vectors are capable of autonomous replication in a host cell into which they are introduced (e.g., bacterial vectors having a bacterial origin of replication and episomal mammalian vector). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

BRIEF DESCRIPTION OF THE DRAWINGS

FIG. 1A shows high binding OxLDL, FIG. 1B shows malondialdehyde-LDL, and FIG. 1C shows hypochlorite modified LDL, all as described herein.

FIG. 4A shows antibody FF1, FIG. 4B shows antibody FF3, FIG. 4D shows antibody FF4, FIG. 4D shows antibody FF5, FIG. 4E shows antibody FF6, and FIG. 4F shows control hlgG1-LALA.

FIG. 6A depicts data for human LOX-1, and FIG. 6B depicts data for cyno LOX-1.

DETAILED DESCRIPTION

Figure 1A:
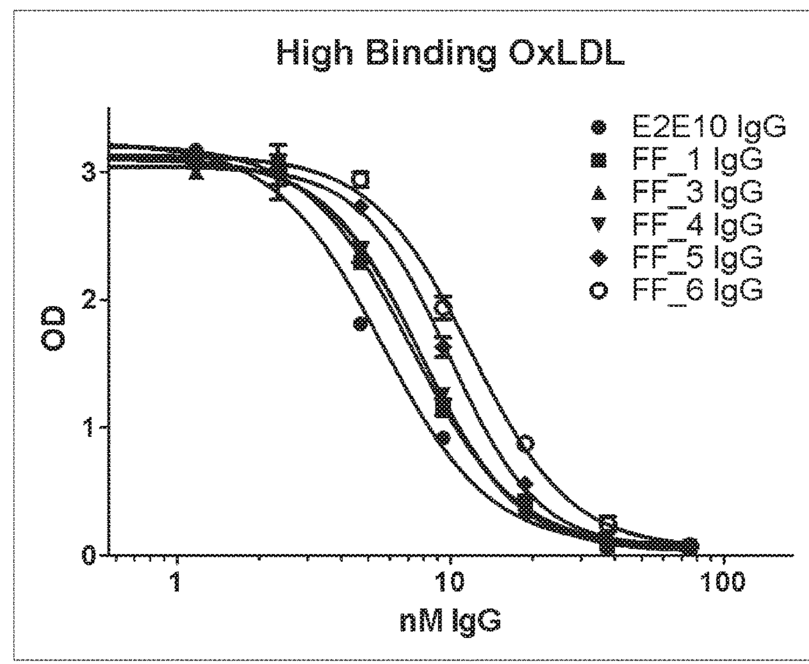
FIGS. 1A-1C depicts the inhibition of OxLDL binding to LOX-1 protein by the LOX-1 antibodies of the invention.

The present invention is based, in part, on the discovery of antibody molecules that specifically bind to LOX-1 and inhibit its biological activities. The invention relates to both full IgG format antibodies as well as antigen binding fragments thereof, such as Fab fragments (e.g., antibodies E2E10, FF1, FF3, FF4, FF5, FF6).

Accordingly, the present invention provides antibodies that specifically bind to LOX-1 (e.g., human LOX-1 and cynomolgus monkey LOX-1), pharmaceutical compositions, production methods, and methods of use of such antibodies and compositions.

LOX-1 Proteins

The present invention provides antibodies that specifically bind to LOX-1 and inhibit its biological activities, including its pro-oxidative and pro-inflammatory activities. LOX-1, a receptor for oxidatively modified LDLs (oxLDLs), is expressed on the surface of vascular cells (endothelial cells and smooth muscle cells), neutrophils, monocytes and macrophages, and platelets. Furthermore, LOX-1 is upregulated in vascular diseases, including in human and animal atherosclerotic lesions (Kataoka H, et al., Circulation 99; 3114-3117). LOX-1 is also upregulated in systemic inflammatory/autoimmune diseases (e.g., rheumatoid arthritis, uveitis, age-related macular degeneration, and pre-eclampsia). OxLDLs are implicated in the pathogenesis of vascular disease. In addition to oxLDLs, LOX-1 binds other ligands including acetylated LDL, advanced glycation end products (AGEs), heat shock protein 70, (HSP70), apoptotic cells, aged red blood cells, leukocytes, activated platelets, bacteria, phosphatidylserine, and C reactive protein (CRP).

LOX-1 is a type-II membrane protein which belongs to the C-type lectin family. LOX-1 also is classified as a class E scavenger receptor. LOX-1 consists of 4 domains: a short N-terminal cytoplasmic domain, a transmembrane region, a connecting neck, and a lectin-like domain at the C-terminus. The C-terminal lectin-like domain (CTLD; also referred to as the oxLDL binding domain) is the ligand binding domain (Sawamura T, et al., Nature 386; 73-77; Shi X, et al., J Cell Sci. 114; 1273-1282). Human LOX-1 has the sequence as set out in Table 1 (SEQ ID NO:1), and has been described in previous reports and literature (Nature, Vol. 386, p. 73-77, 1997; Genomics, Vol. 54, No. 2, p. 191-199, 1998; Biochem. J., Vol. 339, Part 1, P. 177-184, 1999; Genbank Accession No. NP 002534).

The oxLDL/LOX-1 pathway contributes to oxidative stress, vascular inflammation, atherosclerosis, and impaired tissue blood flow and oxygen delivery. Activation of LOX-1 by binding of LOX-1 ligands (e.g., oxLDLs) results in generation of reactive oxygen species due to activation of NADPH oxidase, and subsequent activation of NFkB and MAP kinase pathways resulting in inflammation. The oxLDL/LOX-1 signaling pathway acts as a positive feedback loop, in that LOX-1 induced reactive oxygen species results in formation of additional oxLDL and upregulates LOX-1 expression. Binding of oxLDLs to LOX-1 expressed on the surface of macrophages also results in uptake of oxLDL which contributes to foam cell formation and atherosclerosis. Importantly, vascular inflammation is thought to be critical to the pathobiology of acute thrombotic complications of atherosclerosis including myocardial infarction and ischemic stroke. LOX-1 activation has also been shown to alter vasomotor function by impairing vasodilation by a mechanism involving NADPH oxidase. Impaired vasodilation has been shown to occur in patients with chronic coronary artery disease and angina, and in patients with peripheral artery disease and claudication.

Studies with LOX-1 knockout mice and LOX-1 antagonist antibodies have shown that inhibition of LOX-1 can have beneficial cardiovascular effects. For example, knocking out LOX-1 prevents oxLDL-mediated impairment of vasorelaxation and reduces atherosclerosis (Mehta et al, Circulation Research 2007, 100: 1634). In addition, anti-LOX-1 antibodies have been shown to (i) block oxLDL-induced oxidative stress in human endothelial cells (Ou et al., J Appl Phys 2010, 108: 1745); and (ii) inhibit superoxide production and restore eNOS expression, resulting in improved NO bioavailability and vasodilation (Xu et al., Arteriosclerosis, Thrombosis and Vascular Biology 2007, 27: 871-877).

We propose that inhibiting LOX-1, for example through administration of the anti-LOX-1 antibodies of the invention, will improve blood flow and oxygen delivery to ischemic tissue, resulting in therapeutic benefit to patients with chronic vascular disease, including angina, claudication, and critical limb ischemic. Inhibiting LOX-1, for example through administration of the anti-LOX-1 antibodies of the invention, may also slow or reverse the progression of atherosclerosis and reduce the incidence of its acute thrombotic complications (e.g., acute coronary syndrome, unstable angina, myocardial infarction, and ischemic stroke).

LOX-1 Antibodies & Antigen Binding Fragments

The present invention provides antibodies that specifically bind to LOX-1. In some embodiments, the present invention provides antibodies that specifically bind to human and cynomolgus monkey LOX-1. Antibodies of the invention include, but are not limited to, the human monoclonal antibodies and Fabs, isolated as described in the Examples.

The present invention provides antibodies that specifically bind a LOX-1 protein (e.g., human and cynomolgus monkey LOX-1), wherein the antibodies comprise a VH domain having an amino acid sequence of SEQ ID NOs: 14, 34, 54, 74, or 94. The present invention also provides antibodies that specifically bind to a LOX-1 protein, wherein the antibodies comprise a VH CDR having an amino acid sequence of any one of the VH CDRs listed in Table 1, infra. In particular, the invention provides antibodies that specifically bind to an LOX-1 protein (e.g., human and cynomolgus monkey LOX-1), wherein the antibodies comprise (or alternatively, consist of) one, two, three, or more VH CDRs having an amino acid sequence of any of the VH CDRs listed in Table 1, infra.

The present invention provides antibodies that specifically bind to a LOX-1 protein, said antibodies comprising a VL domain having an amino acid sequence of SEQ ID NOs: 24, 44, 64, 84, or 104. The present invention also provides antibodies that specifically bind to an LOX-1 protein (e.g., human and cynomolgus monkey LOX-1), said antibodies comprising a VL CDR having an amino acid sequence of any one of the VL CDRs listed in Table 2, infra. In particular, the invention provides antibodies that specifically bind to an LOX-1 protein (e.g., human and cynomolgus monkey LOX-1), said antibodies comprising (or alternatively, consisting of) one, two, three or more VL CDRs having an amino acid sequence of any of the VL CDRs listed in Table 1, infra.

Other antibodies of the invention include amino acids that have been mutated, yet have at least 60, 70, 80, 85, 90 or 95 percent identity in the CDR regions with the CDR regions depicted in the sequences described in Table 2. In some embodiments, it includes mutant amino acid sequences wherein no more than 1, 2, 3, 4 or 5 amino acids have been mutated in the CDR regions when compared with the CDR regions depicted in the sequence described in Table 1.

The present invention also provides nucleic acid sequences that encode VH, VL, the full length heavy chain, and the full length light chain of the antibodies that specifically bind to a LOX-1 protein (e.g., human and cynomolgus monkey LOX-1). Such nucleic acid sequences can be optimized for expression in mammalian cells (for example, Table 1 shows the optimized nucleic acid sequences for the heavy chain and light chain of antibodies of the invention).

TABLE 1

Examples of LOX-1 Antibodies, Fabs and LOX-1 Proteins

| Sequence Description | Sequence Identified (SEQ ID NO:) | Amino acid or polynucleotide sequence |
|---|---|---|
| Human LOX-1 full-length protein aeciuence (NCBI Reference Sequence: NM_002543.3) | 1 | MTFDDLKIQTVKDQPDEKSNGKKAKGLQFLYSPWWCLAAATLGVLCLGLVVTIM VLGMQLSQVSDLLTQEQANLTHQKKKLEGQISARQQAEEASQESENELKENTET LARKLNEKSKEQMELHHQNLNLQETLKRVANCSAPCPQDWIWHGENCYLFSSGS FNWEKSQEKCLSLDAKLLKINSTADLDFIQQATSYSSFPFWMGLSRRNPSYPWL WEDGSPLMPHLFRVRGAVSQTYPSGTCAYIQRGAVYAENCILAAFSICQKKANL RAQ |

TABLE 1 -continued

| Examples of LOX-1 Antibodies, Fabs and LOX-1 Proteins | | |
|---|---|---|
| Sequence Description | Sequence Identified (SEQ ID NO:) | Amino acid or polynucleotide sequence |
| Human LOX-1 full-lengLh nucleotide sequence (NCBI Reference Sequence: NM_002543.3) | 2 | ATGACTTTTGATGACCTAAAGATCCAGACTGTGAAGGACCAGCCTGATGAGAAG<br>TCAAATGGAAAAAAAGCTAAAGGTCTTCAGTTTCTTTACTCTCCATGGTGGTGC<br>CTGGCTGCTGCGACTCTAGGGGTCCTTTGCCTGGGATTAGTAGTGACCATTATG<br>GTGCTGGGCATGCAATTATCCCAGGTGTCTGACCTCCTAACACAAGAGCAAGCA<br>AACCTAACTCACCAGAAAAAGAAACTGGAGGGACAGATCTCAGCCCGGCAACAA<br>GCAGAAGAAGCTTCACAGGAGTCAGAAAACGAACTCAAGGAAATGATAGAAACC<br>CTTGCTCGGAAGCTGAATGAGAAATCCAAAGAGCAAATGGAACTTCACCACCAG<br>AATCTGAATCTCCAAGAAACACTGAAGAGAGTAGCAAATTGTTCAGCTCCTTGT<br>CCGCAAGACTGGATCTGGCATGGAGAAAACTGTTACCTATTTTCCTCGGGCTCA<br>TTTAACTGGGAAAAGAGCCAAGAGAAGTGCTTGTCTTTGGATGCCAAGTTGCTG<br>AAAATTAATAGCACAGCTGATCTGGACTTCATCCAGCAAGCAATTTCCTATTCC<br>AGTTTTCCATTCTGGATGGGGCTGTCTCGGAGGAACCCCAGCTACCCATGGCTC<br>TGGGAGGACGGTTCTCCTTTGATGCCCCACTTATTTAGAGTCCGAGGCGCTGTC<br>TCCCAGACATACCCTTCAGGTACCTGTGCATATATACAACGAGGAGCTGTTTAT<br>GCGGAAAACTGCATTTTAGCTGCCTTCAGTATATGTCACAAGAAGGCAAACCTA<br>AGAGCACAG |
| Amino Acid Sequence of mature APP-Avi-soluble human LOX-1 (61-273) (APP and Avi tags underlined) | 6 | EFRHGLNDIFEAQKIEWHESQVSDLLTQEQANLTHQKKKLEGQISARQQ<br>AEEASQESENELKEMIETLARKLNEKSKEQMELHHQNLNLQETLKRVAN<br>CSAPCPQDWIWHGENCYLFSSGSFNWEKSQEKCLSLDAKLLKINSTADL<br>DFIQQAISYSSFPFWMGLSRRNPSYPWLWEDGSPLMPHLFRVRGAVSQT<br>YPSGTCAYIQRGAVYAENCILLAFSICQKKANLRAQ |
| Nucleotide sequence of APP-Avi-soluble human LOX-1 (61-272) (Plasnova # NPL014428) | 7 | ATGCCCCTGCTGCTGCTCCTCCCCCTGCTGTGGGCTGGCGCCCTGGCCGAGTTC<br>CGGCACGGCCTGAACGACATCTTCGAGGCCCAGAAAATCGAGTGGCACGAGAGC<br>CAGGTGTCCGATCTGCTGACCCAGGAACAGGCCAACCTGACCCACCAGAAGAAG<br>AAGCTGGAAGGCCAGATCAGCGCCAGACAGCAGGCCGAGGAAGCCAGCCAGGAA<br>AGCGAGAACGAGCTGAAAGAGATGATCGAGACACTGGCCCGGAAGCTGAACGAG<br>AAGTCCALAGAACAGATGGAACTGCACCACCAGAACCTGAATCTGCAGGAAACC<br>CTGAAGCGGGTCGCCAACTGCAGCGCCCCCTGCCCCCAGGACTGGATCTGGCAC<br>GGCGAGAACTGCTACCTGTTCAGCAGCGGCAGCTTCAACTGGGAGAAGTCCCAG<br>GAAAAGTGCCTGAGCCTGGACGCCAAGCTGCTGAAGATCAACAGCACCGCCGAC<br>CTGGACTTCATCCAGCAGGCCATCAGCTACAGCAGCTICCCTITCTGGATGGGC<br>CTGAGCCGGCGGAACCCCAGCTACCCTTGGCTCTGGGAGGACGGCAGCCCCCTG<br>ATGCCCCACCTGTTCAGAGTGCGGGGAGCTGTGAGCCAGACCTACCCCAGCGGC<br>ACCTGTGCCTACATCCAGCGCGGAGCCGTGTACGCCGAGAACTGCATCCTGGCC<br>GCCTTCAGCATCTGCCAGAAGAAGGCCAATCTGCGGGCCCAGTAATAA |
| FF1 | | |
| HCDR1 (Kabat) | 8 | DYEVH |
| HCDR2 (Kabat) | 9 | AIHPGSGGAAYVQKFQG |
| HCDR3 (Kabat) | 10 | WLPMDY |
| HCDR1 (Chothia) | 11 | GYTFTDY |
| HCDR2 (Chothia) | 12 | HPGSGG |
| HCDR3 (Chothia) | 13 | WLPMDY |
| VH | 14 | QVQLVQSGAEVKKPGASVKVSCKASGYTFTDYEVHWVRQAPGQGLEWMGAIHPG<br>SGGAAYVQKFQGRVTMTRDTSTSTAYMELSSLRSDDTAVYYCARWLPMDYWGQG<br>TLVTVSS |
| DNA encoding VH | 15 | caggtgcagctggtgcagtctggcgccgaagtgaagaaacctggcgcctccgtg<br>aaggtgtcctgcaaggcttccggctacacctttaccgactacgaggtgcactgg<br>gtgcgacaggctccaggccagggactggaatggatgggcgctatccatcctggc<br>tctggcggcgctgcttacgtgcagaaattccagggcagagtgaccatgacccgg<br>gacacctctacctccaccgcctacatggaactgtcctccctgcggagcgacgac<br>accgccgtgtactactgtgcccggtggctgcccatggactattggggccagggc<br>accctcgtgaccgtgtcctct |
| Heavy Chain | 16 | QVQLVQSGAEVKKPGASVKVSCKASGYTFTDYEVHWVRQAPGQGLEWMGAIHPG<br>SGGAAYVQKFQGRVTMTRDTSTSTAYMELSSLRSDDTAVYYCARWLPMDYWGQG<br>TLVTVSSASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKVDKRVEPK<br>SCDKTHTCPPCPAPEAAGGPSVFLFPPKPKDTLMISRTPEVTCVVVDVSHEDPE<br>VKFNWYVDGVEVHNAKTKPREEQYNSTYRVVSVETVLEQDWLNGKEYKCKVSNK<br>ALPAPIEKTISKAKGQPREPQVYTLPPSREEMTKNQVSLTCLVNGFYPSDIAVE<br>WESNGQPENNYKTTPPVLDSDGSFFLYSKLTVDKSRWQQGNVFSCSVMHEALHN<br>HYTQKSLSLSPGK |
| DNA Encoding Heavy Chain | 17 | caggtgcagctggtgcagtctggcgccgaagtgaagaaacctggcgcctccgtg<br>aaggtgtcctgcaaggcttccggctacacctttaccgactacgaggtgcactgg<br>gtgcgacaggctccaggccagggactggaatggatgggcgctatccatcctggc<br>tctggcggcgctgcttacgtgcagaaattccagggcagagtgaccatgacccgg<br>gacacctctacctccaccgcctacatggaactgtcctccctgcggagcgacgac<br>accgccgtgtactactgtgcccggtggctgcccatggactattggggccagggc<br>accctcgtgaccgtgtcctctgcttctaccaagggcccttccgtgttccctctg |

TABLE 1 -continued

Examples of LOX-1 Antibodies, Fabs and LOX-1 Proteins

| Sequence Description | Sequence Identified (SEQ ID NO:) | Amino acid or polynucleotide sequence |
|---|---|---|
| | | gccccttccagcaagtctacctctggcggcaccgcagctctgggctgcctggtg<br>aaggactacttccctgagcctgtgacagtgtcctggaactctggcgccctgacc<br>agcggagtgcacaccttccctgccgtgctgcagtcctccggcctgtactccctg<br>tcctccgtggtgacagtgccttcctccagcctgggcacacagacctacatctgc<br>aacgtgaaccacaagccttccaacaccaaggtggacaagcgggtggagcctaag<br>tcctgcgacaagacccacacctgtcctccatgtcctgcccctgaagccgctggc<br>ggcccttctgtgtttctgttccccccaaagcccaaggacaccctgatgatctcc<br>cggacccctgaagtgacctgcgtggtggtggacgtgtcccacgaggatcctgaa<br>gtgaagttcaattggtacgtggacggcgtggaggtgcacaacgccaagaccaag<br>cctcgggaggaacagtacaactccacctaccgggtggtgtccgtgctgaccgtg<br>ctgcaccaggactggctgaacggcaaagaatacaagtgcaaggtgtccaacaag<br>gccctgcctgcccctatcgaaaagaccatctccaaggccaagggccagcctagg<br>gaaccccaggtgtacaccctgccacccagccgggaagaaatgaccaagaaccag<br>gtgtccctgacctgtctggtgaagggcttctacccttccgatatcgccgtggag<br>tgggagtctaacggccagcctgagaacaactacaagaccacccctcctgtgctg<br>gactccgacggctccttcttcctgtactccaaactgaccgtggacaagtcccgg<br>tggcagcagggcaacgtgttctcctgctctgtgatgcacgaggccctgcacaac<br>cactacacccagaagtccctgtccctgtctcccggcaag |
| LCDR1 (Kabat) | 18 | RASQGINNWLV |
| LCDR2 (Kabat) | 19 | AASSLQS |
| LCDR3 (Kabat) | 20 | QQYLITPYT |
| LCDR1 (Chothia) | 21 | SQGINNW |
| LCDR2 (Chothia) | 22 | AAS |
| LCD33 (Thothia) | 23 | YLITPY |
| VL | 24 | DIQMTQSPSSVSASVGDRVTITCRASQGINNWLVWYQQKPGKAPKLLIYAASSL<br>QSGVPSRFSGSGSGADYTLTISSLQPEDFATYYCQQYLITPYTFGQGTKLEIK |
| DNA Encoding VL | 25 | gacatccagatgacccagtcccccctcctccgtgtctgcttccgtgggcgacaga<br>gtgaccatcacctgtagagcctcccagggcatcaacaactggctcgtgtggtat<br>cagcagaagcccggcaaggcccccaagctgctgatctacgctgcctccagtctg<br>cagtccggcgtgccctctagattctccggctctggctctggcgccgactatacc<br>ctgaccatctccagcctgcagcccgaggacttcgccacctactactgccagcag<br>tacctgatcacccccctacaccttcggccagggcaccaagctggaaatcaag |
| | 26 | DIQMTQSPSSVSASVGDRVTITCRASQGINNWLVWYQQKPGKAPKLLIYAASSL<br>QSGVPSRFSGSGSGADYTLTISSLQPEDFATYYCQQYLITPYTFGQGTKLEIKR<br>TVAAPSVFIFPPSDEQLKSGTASVVCLLNNFYPREAKVQWKVDNALQSGNSQES<br>VTEQDSKDSTYSLSSTLTLSKADYEKHKVYACEVTHQGLSSPVTKSFNRGEC |
| | 27 | gacatccagatgacccagtcccccctcctccgtgtctgcttccgtgggcgacaga<br>gtgaccatcacctgtagagcctcccagggcatcaacaactggctcgtgtggtat<br>cagcagaagcccggcaaggcccccaagctgctgatctacgctgcctccagtctg<br>cagtccggcgtgccctctagattctccggctctggctctggcgccgactatacc<br>ctgaccatctccagcctgcagcccgaggacttcgccacctactactgccagcag<br>tacctgatcacccccctacaccttcggccagggcaccaagctggaaatcaagcgt<br>acggtggccgctcccagcgtgttcatcttccccccaagcgacgagcagctgaag<br>agcggcaccgccagcgtggtgtgtctgctgaacaacttctacccccagggaggcc<br>aaggtgcagtggaaggtggacaacgccctgcagagcggcaacagccaggagagc<br>gtcaccgagcaggacagcaaggactccacctacagcctgagcagcaccctgacc<br>ctgagcaaggccgactacgagaagcacaaggtgtacgcctgtgaggtgacccac<br>cagggcctgtccagccccgtgaccaagagcttcaacaggggcgagtgc |
| FF3 | | |
| HCDR1 (Kabat) | 28 | DYEVH |
| HCDR2 (Kabat) | 29 | AIHPGSGGAAYVQKFQG |
| HCDR3 (Kabat) | 30 | WLPMDY |
| HCDR1 (Chothia) | 31 | GYTFTDY |
| HCDR2 (Chothia) | 32 | HPGSGG |
| HCDR3 (Chothia) | 33 | WLPMDY |
| VH | 34 | QVQLVQSGAEVKKPGASVKVSCKASGYTFTDYEVHWVRQAPGQGLEWMGAIHPG<br>SGGAAYVQKFQGRVTMTRDTSISTAYMELSRLRSDDTAVYYCARWLPMDYWGQG<br>TLVTVSS |
| DNA VH | 35 | caggtgcagctggtgcagtctggcgccgaagtgaagaaacctggcgcctccgtg<br>aaggtgtcctgcaaggcttccggctacacctttaccgactacgaggtgcactgg<br>gtgcgacaggctccaggccagggactggaatggatgggcgctatccatcctggc<br>tctggcggcgctgcttacgtgcagaaattccagggcagagtgaccatgacccgg<br>gacacctccatctccaccgcctacatggaactgtcccggctgagatccgacgac<br>accgccgtgtactactgcgccagatggctgcccatggactactggggccagggc<br>acactcgtgaccgtgtcctct |
| Heavy Chain | 36 | QVQLVQSGAEVKKPGASVKVSCKASGYTFTDYEVHWVRQAPGQGLEWMGAIHPG<br>SGGAAYVQKFQGRVTMTRDTSISTAYMELSRLRSDDTAVYYCARWLPMDYWGQG<br>TLVTVSSASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKVDKRVEPK<br>SCDKTHTCPPCPAPEAAGGPSVFLFPPKPKDTLMISRTPEVTCVVVDVSHEDPE |

TABLE 1 -continued

Examples of LOX-1 Antibodies, Fabs and LOX-1 Proteins

| Sequence Description | Sequence Identified (SEQ ID NO:) | Amino acid or polynucleotide sequence |
|---|---|---|
| | | VKFNWYVDFVEVHNAKTKPREEQYNSTYRVVSVLTVLHQDWLNGKEYKCKVSNK ALPAPIEKTISKAKGQPREPQVYTLPPSREEMTKNQVSLTCLVKGFYPSDIAVE WESNGQPENNYKTTPPVLDSDGSFFLYSKLTVDKSRWQQGNVFSCSVMHEALHN HYTQLSLSLSPGK |
| DNA Heavy Chain | 37 | caggtgcagctggtgcagtctggcgccgaagtgaagaaacctggcgcctccgtg aaggtgtcctgcaaggcttccggctacacctttaccgactacgaggtgcactgg gtgcgacaggctccaggccagggactggaatggatgggcgctatccatcctggc tctggcggcgctgcttacgtgcagaaattccagggcagagtgaccatgacccgg gacacctccatctccaccgcctacatggaactgtcccggctgagatccgacgac accgccgtgtactactgcgccagatggctgcccatggactactggggccagggc acactcgtgaccgtgtcctctgcttccaccaagggcccttccgtgttccctctg gccccttccagcaagtctacctctggcggcaccgcagctctgggctgcctggtg aaggactacttccctgagcctgtgacagtgtcctggaactctggcgccctgacc agcggagtgcacaccttccctgccgtgctgcagtcctccggcctgtactccctg tcctccgtggtgacagtgccttcctccagcctgggcacacagacctacatctgc aacgtgaaccacaagccttccaacaccaaggtggacaagcgggtggagcctaag tcctgcgacaagacccacacctgtcctccatgtcctgcccctgaagccgctggc ggcccttctgtgtttctgttccccccaaagcccaaggacaccctgatgatctcc cggacccctgaagtgacctgcgtggtggtggacgtgtcccacgaggatcctgaa gtgaagttcaattggtacgtggacggcgtggaggtgcacaacgccaagaccaag cctcgggaggaacagtacaactccacctaccgggtggtgtccgtgctgaccgtg ctgcaccaggactggctgaacggcaaagaatacaagtgcaaggtgtccaacaag gccctgcctgcccctatcgaaaagaccatctccaaggccaagggccagcctagg gaaccccaggtgtacaccctgccacccagccgggaagaaatgaccaagaaccag gtgtccctgacctgtctggtgaagggcttctacccttccgatatcgccgtggag tgggagtctaacggccagcctgagaacaactacaagaccacccctcctgtgctg gactccgacggctccttcttcctgtactccaaactgaccgtggacaagtcccgg tggcagcagggcaacgtgttctcctgctctgtgatgcacgaggccctgcacaac cactacacccagaagtccctgtccctgtctcccggcaag |
| LCDR1 (Kabat) | 38 | RASQGINNWLV |
| LCDR2 (Kabat) | 39 | AASSLQS |
| LCDR3 (Kabat) | 40 | QQYLITPYT |
| LCDR1 (Chothia) | 41 | SQGINNW |
| LCD32 (Chothia) | 42 | AAS |
| LCDR3 (Chothia) | 43 | YLITPY |
| VL | 44 | DIQMTQSPSSVSASVGDRVTITCRASQGINNWLVWYQQKPGKAPKLLIYAASSL QSGVPSRFSGSGSGADYTLTISSLQPEDFATYYCQQYLITPYTFGQGTKLEIK |
| DNA VL | 45 | gacatccagatgacccagtcccccctcctccgtgtctgcttccgtgggcgacaga gtgaccatcacctgtagagcctcccagggcatcaacaactggctcgtgtggtat cagcagaagcccggcaaggcccccaagctgctgatctacgctgcctccagtctg cagtccggcgtgccctctagattctccggctctggctctggcgccgactatacc ctgaccatctccagcctgcagcccgaggacttcgccacctactactgccagcag tacctgatcacccccctacaccttcggccagggcaccaagctggaaatcaag |
| Light Chain | 46 | DIQMTQSPSSVSASVGDRVTITCRASQGINNWLVWYQQKPGKAPKLLIYAASSL QSGVPSRFSGSGSGADYTLTISSLQPEDFATYYCQQYLITPYTFGQGTKLEIKR TVAAPSVFIFPPSDEQLKSGTASVVCLLNNFYPREAKVQWKVDNALQSGNSQES VTEQDSKDSTYSLSSTLTLSKADYEKHKVYACENTHQGLSSPVTKSFNRGEC |
| DNA Light Chain | 47 | gacatccagatgacccagtcccccctcctccgtgtctgcttccgtgggcgacaga gtgaccatcacctgtagagcctcccagggcatcaacaactggctcgtgtggtat cagcagaagcccggcaaggcccccaagctgctgatctacgctgcctccagtctg cagtccggcgtgccctctagattctccggctctggctctggcgccgactatacc ctgaccatctccagcctgcagcccgaggacttcgccacctactactgccagcag tacctgatcacccccctacaccttcggccagggcaccaagctggaaatcaagcgt acggtggccgctcccagcgtgttcatcttcccccccaagcgacgagcagctggag agcggcaccgccagcgtggtgtgtctgctgaacaacttctacccccagggaggcc aaggtgcagtggaaggtggacaacgccctgcagagcggcaacagccaggagagc gtcaccgagcaggacagcaaggactccacctacagcctgagcagcaccctgacc ctgagcaaggccgactacgagaagcacaaggtgtacgcctgtgaggtgacccac cagggcctgtccagccccgtgaccaagagcttcaacaggggcgagtgc |
| FF4 | | |
| HCDR1 (Kabat) | 43 | DYEVH |
| HCDR2 (Kabat) | 49 | AIHPGSGGAAYVQKFQG |
| HCDR2 (Kabat) | 50 | WLPMDY |
| H2DR1 (Chothia) | 51 | GYTFTDY |
| HCDR2 (Chothia) | 52 | HPGSGG |
| HCDR3 (Chothia) | 53 | WLPMDY |
| VH | 54 | QVQLVQSGAEVKKPGASVKVSCKASGYTFTDYEVHWVRQAPGQGLEWMGAIHPG SGGAAYVQKFQGRVTMTRDTSISTAYMELSRLRSDDTAVYYCARWLPMDYWGQG TLVTVSS |

TABLE 1 -continued

Examples of LOX-1 Antibodies, Fabs and LOX-1 Proteins

| Sequence Description | Sequence Identified (SEQ ID NO:) | Amino acid or polynucleotide sequence |
|---|---|---|
| DNA VH | 55 | caggtgcagctggtgcagtctggcgccgaagtgaagaaacctggcgcctccgtg<br>aaggtgtcctgcaaggcttccggctacacctttaccgactacgaggtgcactgg<br>gtgcgacaggctccaggccagggactggaatggatgggcgctatccatcctggc<br>tctggcggcgctgcttacgtgcagaaattccagggcagagtgaccatgacccgg<br>gacacctccatctccaccgcctacatggaactgtcccggctgagatccgacgac<br>accgccgtgtactactgcgccagatggctgcccatggactactggggccagggc<br>acactcgtgaccgtgtcctct |
| Heavy Chain | 56 | QVQLVQSGAEVKKPGASVKVSCKASGYTFTDYEVHWVRQAPGQGLEWMGAIHPG<br>SGGAAYVQKFQGRVTMTRDTSISTAYMELSRLRSDDTAVYYCARWLPMDYWGQG<br>TLVTVSSASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKVDKRVEPK<br>SCDKTHTCPPCPAPEAAGGPSVFLFPPKPKDTLMISRTPEVTCVVVDVSHEDPE<br>VKFNWYVDGVEVHNAKTKPREEQYNSTYRVVSVLTVLHQDWLNGKEYKCKVSNK<br>ALPAPIEKTISKAKGQPREPQVYTLPPSREEMTKNQVSLTCLVKGFYPSDIAVE<br>WESNGQPENNYKTTPPVLDSDGSFFLYSKLTVDKSRWQQGNVFSCSVMHEALHN<br>HYTQLSLSLSPGK |
| DNA Heavy Chain | 57 | Caggtgcagctggtgcagtctggcgccgaagtgaagaaacctggcgcctccgtg<br>aaggtgtcctgcaaggcttccggctacacctttaccgactacgaggtgcactgg<br>gtgcgacaggctccaggccagggactggaatggatgggcgctatccatcctggc<br>tctggcggcgctgcttacgtgcagaaattccagggcagagtgaccatgacccgg<br>gacacctccatctccaccgcctacatggaactgtcccggctgagatccgacgac<br>accgccgtgtactactgcgccagatggctgcccatggactactggggccagggc<br>acactcgtgaccgtgtcctctgcttccaccaagggcccttccgtgttccctctg<br>gccccttccagcaagtctacctctggcggcaccgcagctctgggctgcctggtg<br>aaggactacttccctgagcctgtgacagtgtcctggaactctggcgccctgacc<br>agcggagtgcacaccttccctgccgtgctgcagtcctccggcctgtactccctg<br>tcctccgtggtgacagtgccttcctccagcctgggcacacagacctacatctgc<br>aacgtgaaccacaagccttccaacaccaaggtggacaagcgggtggagcctaag<br>tcctgcgacaagacccacacctgtcctccatgtcctgcccctgaagccgctggc<br>ggcccttctgtgtttctgttccccccaaagcccaaggacaccctgatgatctcc<br>cggacccctgaagtgacctgcgtggtggtggacgtgtcccacgaggatcctgaa<br>gtgaagttcaattggtacgtggacggcgtggaggtgcacaacgccaagaccaag<br>cctcgggaggaacagtacaactccacctaccgggtggtgtccgtgctgaccgtg<br>ctgcaccaggactggctgaacggcaaagaatacaagtgcaaggtgtccaacaag<br>gccctgcctgcccctatcgaaaagaccatctccaaggccaagggccagcctagg<br>gaaccccaggtgtacaccctgccacccagccgggaagaaatgaccaagaaccag<br>gtgtccctgacctgtctggtgaagggcttctacccttccgatatcgccgtggag<br>tgggagtctaacggccagcctgagaacaactacaagaccacccctcctgtgctg<br>gactccgacggctccttcttcctgtactccaaactgaccgtggacaagtcccgg<br>tggcagcagggcaacgtgttctcctgctctgtgatgcacgaggccctgcacaac<br>cactacacccagaagtccctgtccctgtctcccggcaag |
| LCDR1 (Kabat) | 58 | RASQGITNWLA |
| LCDR2 (Kabat) | 59 | AASILES |
| LCDR3 (Kabat) | 60 | QQYLITPYT |
| LCDR1 (Chothia) | 61 | SQCITNW |
| LCDR2 (Chothia) | 62 | AAS |
| LCDR3 (Chothia) | 63 | YLITPY |
| VL | 64 | DIQMTQSPSSVSASVGDRVTITCRASQGITNWLAWYQQKPGKAPKLLIYAASIL<br>ESGVPSPFSGSGSGTDYTLTISSLQPEDIATYYCQQYLITPYTFGQGTKLEIK |
| DNA VL | 65 | gacatccagatgacccagtccccctcctccgtgtctgcttccgtgggcgacaga<br>gtgaccatcacctgtagagcctcccagggcatcaccaactggctggcctggtat<br>cagcagaagcccggcaaggcccccaagctgctgatctacgccgcctccatcctg<br>gaatccggcgtgccctctagattctccggctctggctctggcaccgactatacc<br>ctgaccatctccagcctgcagcccgaggatatcgccacctactactgccagcag<br>tacctgatcaccccctacaccttcggccagggcaccaagctggaaatcaag |
| Light Chain | 63 | DIQMTQSPSSVSASVGDRVTITCRASQGITNWLAWYQQKPGKAPKLLIYAASIL<br>ESGVPSRFSGSGSGTDYTLTISSLQPEDIATYYCQQYLITPYTFGQGTKLEIKR<br>TVAAPSVFIFPPSDEQLKSGTASVVCLLNNFYPREAKVQWKVDNALQSGNSQES<br>VTEQDSKDSTYSLSSTLTLSKADYEKHKVYACENTHQGLSSPVTKSFNRGEC |
| DNA Light Chain | 67 | gacatccagatgacccagtccccctcctccgtgtctgcttccgtgggcgacaga<br>gtgaccatcacctgtagagcctcccagggcatcaccaactggctggcctggtat<br>cagcagaagcccggcaaggcccccaagctgctgatctacgccgcctccatcctg<br>gaatccggcgtgccctctagattctccggctctggctctggcaccgactatacc<br>ctgaccatctccagcctgcagcccgaggatatcgccacctactactgccagcag<br>tacctgatcaccccctacaccttcggccagggcaccaagctggaaatcaagcgt<br>acggtggccgctcccagcgtgttcatcttcccccccaagcgacgagcagctgaag<br>agcggcaccgccagcgtggtgtgtctgctgaacaacttctaccccagggaggcc<br>aaggtgcagtggaaggtggacaacgccctgcagagcggcaacagccaggagagc<br>gtcaccgagcaggacagcaaggactccacctacagcctgagcagcaccctgacc |

TABLE 1 -continued

| Examples of LOX-1 Antibodies, Fabs and LOX-1 Proteins | | |
|---|---|---|
| Sequence Description | Sequence Identified (SEQ ID NO:) | Amino acid or polynucleotide sequence |
| | | ctgagcaaggccgactacgagaagcacaaggtgtacgcctgtgaggtgacccac cagggcctgtccagccccgtgaccaagagcttcaacaggggcgagtgc |
| FF5 | | |
| HCDR1 (Kabat) | 68 | DYEVE |
| HCDR2 (Kabat) | 69 | AIHPGSGGAAYVQKFQG |
| HCDR3 (Kabat) | 70 | WLPMDY |
| HCDR1 (Chothia) | 71 | GYTFTDY |
| HCDR2 (Chothia) | 72 | HPGSGG |
| HCDR3 (Chothia) | 73 | WLPMDY |
| VH | 74 | QVQLVQSGAEVKKPGASVKVSCKASGYTFTDYEVHWVRQAPGQGLEWMGAIHPG SGGAAYVQKFQGRVTMTRDTSISTAYMELSRLRSDDTAVYYCARWLPMDYWGQG TLVTVSS |
| DNA VH | 75 | caggtgcagctggtgcagtctggcgccgaagtgaagaaacctggcgcctccgtg aaggtgtcctgcaaggcttccggctacacctttaccgactacgaggtgcactgg gtgcgacaggctccaggccagggactggaatggatgggcgctatccatcctggc tctggcggcgctgcttacgtgcagaaattccagggcagagtgaccatgacccgg gacacctccatctccaccgcctacatggaactgtcccggctgagatccgacgac accgccgtgtactactgcgccagatggctgcccatggactactggggccagggc acactcgtgaccgtgtcctct |
| Heavy Chain | 76 | QVQLVQSGAEVKKPGASVKVSCKASGYTFTDYEVHWVRQAPGQGLEWMGAIHPG SGGAAYVQKFQGRVTMTRDTSISTAYMELSRLRSDDTAVYYCARWLPMDYWGQG TLVTVSSASTKGPSVFPLAPSSKSTSGGTAALGCLVKDYFPEPVTVSWNSGALT SGVHTFPAVLQSSGLYSLSSVVTVPSSSLGTQTYICNVNHKPSNTKVDKRVEPK SCDKTHTCPPCPAPEAAGGPSVFLFPPKPKDTLMISRTPEVTCVVVDVSHEDPE VKFNWYVDGVEVHNAKTKPREEQYNSTYRVVSVLTVLHQDWLNGKEYKCKVSNK ALPAPIEKTISKAKGQPREPQVYTLPPSREEMTKNQVSLTCLVKGFYPSDIAVE WESNGQPENNYKTTPPVLDSDGSFFLYSKLTVDKSRWQQGNVFSCSVMHEALHN HYTQLSLSLSPGK |
| DNA Heavy Chain | 77 | caggtgcagctggtgcagtctggcgccgaagtgaagaaacctggcgcctccgtg aaggtgtcctgcaaggcttccggctacacctttaccgactacgaggtgcactgg gtgcgacaggctccaggccagggactggaatggatgggcgctatccatcctggc tctggcggcgctgcttacgtgcagaaattccagggcagagtgaccatgacccgg gacacctccatctccaccgcctacatggaactgtcccggctgagatccgacgac accgccgtgtactactgcgccagatggctgcccatggactactggggccagggc acactcgtgaccgtgtcctctgcttccaccaagggcccttccgtgttccctctg gccccttccagcaagtctacctctggcggcaccgcagctctgggctgcctggtg aaggactacttccctgagcctgtgacagtgtcctggaactctggcgccctgacc agcggagtgcacaccttccctgccgtgctgcagtcctccggcctgtactccctg tcctccgtggtgacagtgccttcctccagcctgggcacacagacctacatctgc aacgtgaaccacaagccttccaacaccaaggtggacaagcgggtggagcctaag tcctgcgacaagacccacacctgtcctccatgtcctgcccctgaagccgctggc ggcccttctgtgtttctgttcccccaaagcccaaggacaccctgatgatctcc cggacccctgaagtgacctgcgtggtggtggacgtgtcccacgaggatcctgaa gtgaagttcaattggtacgtggacggcgtggaggtgcacaacgccaagaccaag cctcgggaggaacagtacaactccacctaccgggtggtgtccgtgctgaccgtg ctgcaccaggactggctgaacggcaaagaatacaagtgcaaggtgtccaacaag gccctgcctgcccctatcgaaaagaccatctccaaggccaagggccagcctagg gaaccccaggtgtacaccctgccacccagccgggaagaaatgaccaagaaccag gtgtccctgacctgtctggtgaagggcttctacccttccgatatcgccgtggag tgggagtctaacggccagcctgagaacaactacaagaccacccctcctgtgctg gactccgacggctccttcttcctgtactccaaactgaccgtggacaagtcccgg tggcagcagggcaacgtgttctcctgctctgtgatgcacgaggccctgcacaac cactacacccagaagtccctgtccctgtctcccggcaag |
| LCDR1 (Kabat) | 78 | RASQGINNWLV |
| LCDR2 (Kabat) | 79 | AASRLES |
| LCDR3 (Kabat) | 80 | QQYLITPYT |
| LCDR1 (Chothia) | 81 | SQGINNW |
| LCDR2 (Chothia) | 82 | AAS |
| LCDR3 (Chothia) | 83 | YLITPY |
| VL | 84 | DIQMTQSPSSVSASVGDRVTITCRASQGINNWLAWYQQKPGKAPKLLLYAASRL ESGVPSRFSGSGSGTDYTLTISSLQPEDIATYYCQQYLITPYTFGQGTKLEIK |
| DNA VL | 85 | gacatccagatgacccagtccccctcctccgtgtctgcttccgtgggcgacaga gtgaccatcacctgtagagcctcccagggcatcaacaactggctcgtgtggtat cagcagaagcccggcaaggcccccaaactgctgctgtacgccgcctccagactg gaatctggcgtgccctccagattctccggctctggctctggcaccgactatacc ctgaccatctccagcctgcagcccgaggatatcgccacctactactgccagcag tacctgatcaccccctacaccttcggccagggcaccaagctggaaatcaag |
| Light Chain | 86 | DIQMTQSPSSVSASVGDRVTITCRASQGINNWLVWYQQKPGKAPKLLLYAASRL ESGVPSRFSGSGSGTDYTLTISSLQPEDIATYYCQQYLITPYTFGQGTKLEIKR TVAAPSVFIFPPSDEQLKSGTASVVCLLNNFYPREAKVQWKVDNALQSGNSQES VTEQDSKDSTYSLSSTLTLSKADYEKHKVYACENTHQGLSSPVTKSFNRGEC |

TABLE 1 -continued

| Examples of LOX-1 Antibodies, Fabs and LOX-1 Proteins | | |
|---|---|---|
| Sequence Description | Sequence Identified (SEQ ID NO:) | Amino acid or polynucleotide sequence |
| DNA Light Chain | 87 | gacatccagatgacccagtcccccctcctccgtgtctgcttccgtgggcgacaga gtgaccatcacctgtagagcctcccagggcatcaacaactggctcgtgtggtat cagcagaagcccggcaaggcccccaaactgctgctgtacgccgcctccagactg gaatctggcgtgccctccagattctccggctctggctctggcaccgactatacc ctgaccatctccagcctgcagcccgaggatatcgccacctactactgccagcag tacctgatcacccccctacaccttcggccagggcaccaagctggaaatcaagcgt acggtggccgctcccagcgtgttcatcttcccccccaagcgacgagcagctgaag agcggcaccgccagcgtggtgtgtctgctgaacaacttctaccccagggaggcc aaggtgcagtggaaggtggacaacgccctgcagagcggcaacagccaggagagc gtcaccgagcaggacagcaaggactccacctacagcctgagcagcaccctgacc ctgagcaaggccgactacgagaagcacaaggtgtacgcctgtgaggtgacccac cagggcctgtccagccccgtgaccaagagcttcaacaggggcgagtgc |
| FF6 | | |
| HCDR1 (Kabat) | 88 | DYEVH |
| HCDR2 (Kabat) | 89 | AIHPGSGGAAYVQKFQG |
| HCDR3 (Kabat) | 90 | WLPIDY |
| HCDR1 (Chothia) | 91 | GYTFTDY |
| HCDR2 (Chothia) | 92 | HPGSGG |
| HCDR3 (Chothia) | 93 | WLPIDY |
| VH | 94 | QVQLVQSGAEVKKPGASVKVSCKASGYTFTDYEVHWVRQAPGQGLEWMGAIHPG SGGAAYVQKFQGRVTMTRDTSISTAYMELSRLRSDDTAVYYCARWLPMDYWGQG TLVTVSS |
| DNA VH | 95 | caggtgcagctggtgcagtctggcgccgaagtgaagaaacctggcgcctccgtg aaggtgtcctgcaaggcttccggctacacctttaccgactacgaggtgcactgg gtgcgacaggctccaggccagggactggaatggatgggcgctatccatcctggc tctggcggcgctgcttacgtgcagaaattccagggcagagtgaccatgacccgg gacacctccatctccaccgcctacatggaactgtcccggctgagatccgacgac accgccgtgtactactgcgccagatggctgcccatcgactactggggccagggc acactcgtgaccgtgtcctct |
| Heavy Chain | 96 | QVQLVQSGAEVKKPGASVKVSCKASGYTFTDYEVHWVRQAPGQGLEWMGAIHPG SGGAAYVQKFQGRVTMTRDTSISTAYMELSRLRSDDTAVYYCARWLPMDYWGQG TLVTVSSASTKGPSVFPLAPSSKSTSGGTAALGCLVKDYFPEPVTVSWNSGALT SGVHTFPAVLQSSGLYSLSSVVTVPSSSLGTQTYICNVNHKPSNTKVDKRVEPK SCDKTHTCPPCPAPEAAGGPSVFLFPPKPKDTLMISRTPEVTCVVVDVSHEDPE VKFNWYVDGVEVHNAKTKPREEQYNSTYRVVSVLTVLHQDWLNGKEYKCKVSNK ALPAPIEKTISKAKGQPREPQVYTLPPSREEMTKNQVSLTCLVKGFYPSDIAVE WESNGQPENNYKTTPPVLDSDGSFFLYSKLTVDKSRWQQGNVFSCSVMHEALHN HYTQLSLSLSPGK |
| DNA Heavy Chain | 97 | caggtgcagctggtgcagtctggcgccgaagtgaagaaacctggcgcctccgtg aaggtgtcctgcaaggcttccggctacacctttaccgactacgaggtgcactgg gtgcgacaggctccaggccagggactggaatggatgggcgctatccatcctggc tctggcggcgctgcttacgtgcagaaattccagggcagagtgaccatgacccgg gacacctccatctccaccgcctacatggaactgtcccggctgagatccgacgac accgccgtgtactactgcgccagatggctgcccatcgactactggggccagggc acactcgtgaccgtgtcctctgcttccaccaagggcccttccgtgttccctctg gccccttccagcaagtctacctctggcggcaccgcagctctgggctgcctggtg aaggactacttccctgagcctgtgacagtgtcctggaactctggcgccctgacc agcggagtgcacaccttccctgccgtgctgcagtcctccggcctgtactccctg tcctccgtggtgacagtgccttcctccagcctgggcacacagacctacatctgc aacgtgaaccacaagccttccaacaccaaggtggacaagcgggtggagcctaag tcctgcgacaagacccacacctgtcctccatgtcctgcccctgaagccgctggc ggcccttctgtgtttctgttcccccaaagcccaaggacaccctgatgatctcc cggacccctgaagtgacctgcgtggtggtggacgtgtcccacgaggatcctgaa gtgaagttcaattggtacgtggacggcgtggaggtgcacaacgccaagaccaag cctcgggaggaacagtacaactccacctaccgggtggtgtccgtgctgaccgtg ctgcaccaggactggctgaacggcaaagaatacaagtgcaaggtgtccaacaag gccctgcctgcccctatcgaaaagaccatctccaaggccaagggccagcctagg gaaccccaggtgtacaccctgccacccagccgggaagaaatgaccaagaaccag gtgtccctgacctgtctggtgaagggcttctacccttccgatatcgccgtggag tgggagtctaacggccagcctgagaacaactacaagaccacccctcctgtgctg gactccgacggctccttcttcctgtactccaaactgaccgtggacaagtcccgg tggcagcagggcaacgtgttctcctgctctgtgatgcacgaggccctgcacaac cactacacccagaagtccctgtccctgtctcccggcaag |
| LCDR1 (Kabat) | 98 | RASQGINNWLV |
| LCDR2 (Kabat) | 99 | AASRLES |
| LCDR3 (Kabat) | 100 | QQYLITPYT |
| LCDR1 (Chothia) | 101 | SQGINNW |
| LCDR2 (Chothia) | 102 | AAS |
| LCDR3 (Chothia) | 103 | YLITPY |
| VL | 104 | DIQMTQSPSSVSASVGDRVTITCRASQGINNWLVWYQQKPGKAPKLLLYAASRL ESGVPSRFSGSGSGTDYTLTISSLQPEDIATYYCQQYLITPYTFGQGTKLEIK |

TABLE 1 -continued

Examples of LOX-1 Antibodies, Fabs and LOX-1 Proteins

| Sequence Description | Sequence Identified (SEQ ID NO:) | Amino acid or polynucleotide sequence |
|---|---|---|
| DNA VL | 105 | gacatccagatgacccagtcccccctcctccgtgtctgcttccgtgggcgacaga gtgaccatcacctgtagagcctcccagggcatcaacaactggctcgtgtggtat cagcagaagcccggcaaggcccccaaactgctgctgtacgccgcctccagactg gaatctggcgtgccctccagattctccggctctggctctggcaccgactatacc ctgaccatctccagcctgcagcccgaggatatcgccacctactactgccagcag tacctgatcacccccctacaccttcggccagggcaccaagctggaaatcaag |
| Light Chain | 106 | DIQMTQSPSSVSASVGDRVTITCRASQGINNWLVWYQQKPGKAPKLLLYAASRL ESGVPSRFSGSGSGTDYTLTISSLQPEDIATYYCQQYLITPYTFGQGTKLEIKR TVAAPSVFIFPPSDEQLKSGTASVVCLLNNFYPREAKVQWKVDNALQSGNSQES VTEQDSKDSTYSLSSTLTLSKADYEKHKVYACENTHQGLSSPVTKSFNRGEC |
| DNA Light Chain | 107 | gacatccagatgacccagtcccccctcctccgtgtctgcttccgtgggcgacaga gtgaccatcacctgtagagcctcccagggcatcaacaactggctcgtgtggtat cagcagaagcccggcaaggcccccaaactgctgctgtacgccgcctccagactg gaatctggcgtgccctccagattctccggctctggctctggcaccgactatacc ctgaccatctccagcctgcagcccgaggatatcgccacctactactgccagcag tacctgatcacccccctacaccttcggccagggcaccaagctggaaatcaagcgt acggtggccgctcccagcgtgttcatcttcccccccaagcgacgagcagctgaag agcggcaccgccagcgtggtgtgtctgctgaacaacttctaccccagggaggcc aaggtgcagtggaaggtggacaacgccctgcagagcggcaacagccaggagagc gtcaccgagcaggacagcaaggactccacctacagcctgagcagcaccctgacc ctgagcaaggccgactacgagaagcacaaggtgtacgcctgtgaggtgacccac cagggcctgtccagccccgtgaccaagagcttcaacaggggcgagtgc |
| E2E10 (murine parental) | | |
| HCDR1 (Kabat) | 108 | DYEMH |
| HCDR2 (Kabat) | 109 | AIHPGSGGAAYIQKFKG |
| HCDR3 (Kabat) | 110 | WLPMDY |
| HCDR1 (Chothia) | 111 | GYTFTDY |
| HCDR2 (Chothia) | 112 | HPGSGG |
| HCDR3 (Chothia) | 113 | WLPMDY |
| VH | 114 | QVQLQQSGAELVRPGASVKIJSCKALGYTETDYEMHWYTPVHCLEWIGATHPG SEGAAYIQKFKGITAIDKSSSTEMELSSLTSEDSAVYYCTRWLIPMDYG TSVTVSS |
| DNA VH | 115 | caggtccagctgcagcagtcaggagccgaactggtgcggcccggagcttctgtc aaactgagctgcaaggcactgggctacaccttcacagactatgagatgcactgg gtgaaacagaccccccgtccatggactggaatggatcggagcaattcaccctgga agcggaggagcagcttacatccagaagtttaaagggaaggcaactctgaccgcc gacaagagctcctctacagcccatatggagctgagtccactgactagcgaagat agcgccgtgtactattgtacccgctggctgcctatggactattggggacagggg acttcagtgacagtgagttca |
| LCDR1 (Kabat) | 116 | KASDHINNWLA |
| LCDR2 (Kabat) | 117 | GATSLET |
| LCDR3 (Kabat) | 118 | QQYLITPYT |
| LCDR1 (Chothia) | 119 | SDHINNW |
| LCDR2 (Chothia) | 120 | GAT |
| LCDR3 (Chothia) | 121 | YLITPY |
| VH | 122 | DIQMTQSSSYLSVS,GGRVTITCKASDHINNWLAWYQQKPGNAPRLLISGATSL ETGVPSRFSGSGSGKDYTLSITCLQTEDVATYYCQQYLITPYTFGGGTKLEIK |
| DNA VL | 123 | gatattcagatgacccagagtagttcttacctgagcgtgtccctgggaggaagg gtcaccatcacatgcaaggcaagcgaccacattaacaattggctggcctggtac cagcagaaaccaggaaacgcacctcgactgctgatcagcggagctacttccctg gagaccggcgtgccctctagattctctggaagtggctcagggaaggactataca ctgagcattactggcctgcagaccgaagatgtcgctacatactattgtcagcag tacctgattacaccctacactttcggcggcggaactaaactggagattaag |

Other antibodies of the invention include those where the amino acids or nucleic acids encoding the amino acids have been mutated, yet have at least 60, 65, 70, 75, 80, 85, 90, or 95 percent identity to the sequences described in Table 1. Some embodiments include mutant amino acid sequences wherein no more than 1, 2, 3, 4 or 5 amino acids have been mutated in the variable regions when compared with the variable regions depicted in the sequence described in Table 1, while retaining substantially the same antigen binding activity.

Since each of these antibodies can bind to LOX-1, the VH, VL, full length light chain, and full length heavy chain sequences (amino acid sequences and the nucleotide sequences encoding the amino acid sequences) can be "mixed and matched" to create other LOX-1-binding antibodies of the invention. Such "mixed and matched" LOX-1-binding antibodies can be tested using the binding assays known in the art (e.g., ELISAs, and other assays described in the Example section). When these chains are mixed and matched, a VH sequence from a particular VH/VL pairing should be replaced with a structurally similar VH sequence. Likewise a full length heavy chain sequence from a particular full length heavy chain/full length light chain pairing should be replaced with a structurally similar full length heavy chain sequence. Likewise, a VL sequence from a particular VH/VL pairing should be replaced with a structurally similar VL sequence. Likewise a full length light chain sequence from a particular full length heavy chain/full length light chain pairing should be replaced with a structurally similar full length light chain sequence.

Accordingly, in one aspect, the invention provides an isolated antibody or antigen binding region thereof having: a heavy chain variable domain comprising an amino acid sequence selected from the group consisting of SEQ ID NOs: 14, 34, 54, 74, and 94, and a light chain variable domain comprising an amino acid sequence selected from the group consisting of SEQ ID NOs: 24, 44, 64, 84, and 104, wherein the antibody specifically binds to LOX-1 (e.g., human and cynomolgus monkey LOX-1).

More specifically, in certain aspects, the invention provides an isolated antibody or antigen binding region thereof having a heavy chain variable domain and a light chain variable domain comprising amino acid sequences selected from SEQ ID NOs: 14 and 24; 34 and 44; 54 and 64; 74 and 84; or 94 and 104, respectively.

In another aspect, the invention provides (i) an isolated antibody having: a full length heavy chain comprising an amino acid sequence that has been optimized for expression in a mammalian cell selected from the group consisting of SEQ ID NOs: 16, 36, 56, 76, or 96, and a full length light chain comprising an amino acid sequence that has been optimized for expression in a mammalian cell selected from the group consisting of SEQ ID NOs: 26, 46, 66, 86, or 106; or (ii) a functional protein comprising an antigen binding portion thereof. More specifically, in certain aspects, the invention provides an isolated antibody or antigen binding region thereof having a heavy chain and a light chain comprising amino acid sequences selected from SEQ ID NOs: 14 and 24; 34 and 44; 54 and 64; 74 and 84; or 94 and 104, respectively.

The terms "complementarity determining region," and "CDR," as used herein refer to the sequences of amino acids within antibody variable regions which confer antigen specificity and binding affinity. In general, there are three CDRs in each heavy chain variable region (HCDR1, HCDR2, HCDR3) and three CDRs in each light chain variable region (LCDR1, LCDR2, LCDR3).

The precise amino acid sequence boundaries of a given CDR can be readily determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) JMB 273,927-948 ("Chothia" numbering scheme).

For example, under Kabat, the CDR amino acid residues of antibody FF1 in the heavy chain variable domain (VH) are numbered 31-35 (HCDR1), 50-66 (HCDR2), and 99-104 (HCDR3); and the CDR amino acid residues in the light chain variable domain (VL) are numbered 24-34 (LCDR1), 50-55 (LCDR2), and 89-97 (LCDR3). Under Chothia the CDR amino acids in the VH are numbered 26-32 (HCDR1), 52-57 (HCDR2), and 99-104 (HCDR3); and the amino acid residues in VL are numbered 26-32 (LCDR1), 50-52 (LCDR2), and 91-96 (LCDR3). By combining the CDR definitions of both Kabat and Chothia, the CDRs consist of amino acid residues 26-35 (HCDR1), 50-66 (HCDR2), and 90-104 (HCDR3) in human VH and amino acid residues 24-34 (LCDR1), 50-55 (LCDR2), and 89-97 (LCDR3) in human VL.

In another aspect, the present invention provides LOX-1 binding antibodies that comprise the heavy chain and light chain CDR1s, CDR2s, and CDR3s as described in Table 1, or combinations thereof. The amino acid sequences of the VH CDR1s of the antibodies are shown in SEQ ID NOs: 8, 28, 48, 68, and 88. The amino acid sequences of the VH CDR2s of the antibodies and are shown in SEQ ID NOs: 9, 29, 49, 69, and 89. The amino acid sequences of the VH CDR3s of the antibodies are shown in SEQ ID NOs: 10, 30, 50, 70, and 90. The amino acid sequences of the VL CDR1 s of the antibodies are shown in SEQ ID NOs: 18, 38, 58, 78, and 98. The amino acid sequences of the VL CDR2s of the antibodies are shown in SEQ ID NOs: 19, 39, 59, 79, and 99. The amino acid sequences of the VL CDR3s of the antibodies are shown in SEQ ID NOs: 20, 40, 60, 80, and 100. These CDR regions are delineated using the Kabat system.

Alternatively, as defined using the Chothia system (Al-Lazikani et al., (1997) JMB 273, 927-948), the amino acid sequences of the VH CDR1s of the antibodies are shown in SEQ ID NOs: 11, 31, 51, 71, and 91. The amino acid sequences of the VH CDR2s of the antibodies and are shown in SEQ ID NOs: 12, 32, 52, 72, and 92. The amino acid sequences of the VH CDR3s of the antibodies are shown in SEQ ID NOs: 13, 33, 53, 73, and 93. The amino acid sequences of the VL CDR1s of the antibodies are shown in SEQ ID NOs: 21, 41, 61, 81, and 101. The amino acid sequences of the VL CDR2s of the antibodies are shown in SEQ ID NOs: 22, 42, 62, 82, and 102. The amino acid sequences of the VL CDR3s of the antibodies are shown in SEQ ID NOs: 23, 43, 63, 83, and 103.

Given that each of these antibodies can bind to LOX-1 and that antigen-binding specificity is provided primarily by the CDR1, 2 and 3 regions, the VH CDR1, 2 and 3 sequences and VL CDR1, 2 and 3 sequences can be "mixed and matched" (i.e., CDRs from different antibodies can be mixed and matched, although each antibody preferably contains a VH CDR1, 2 and 3 and a VL CDR1, 2 and 3 to create other LOX-1 binding molecules of the invention. Such "mixed and matched" LOX-1 binding antibodies can be tested using the binding assays known in the art and those described in the Examples (e.g., ELISAs, SET, BIACORE™). When VH CDR sequences are mixed and matched, the CDR1, CDR2 and/or CDR3 sequence from a particular VH sequence should be replaced with a structurally similar CDR sequence(s). Likewise, when VL CDR sequences are mixed and matched, the CDR1, CDR2 and/or CDR3 sequence from a particular VL sequence should be replaced with a structurally similar CDR sequence(s). It will be readily apparent to the ordinarily skilled artisan that novel VH and VL sequences can be created by substituting one or more VH and/or VL CDR region sequences with structurally similar sequences from the CDR sequences shown herein for monoclonal antibodies of the present invention. In addition to the foregoing, in one embodiment, the antigen binding fragments of the antibodies described herein can comprise a VH CDR1, 2, and 3, or a VL CDR 1, 2, and 3, wherein the fragment binds to LOX-1 as a single variable domain.

In certain embodiments of the invention, the antibodies or antigen binding fragments thereof may have the heavy and light chain sequences of the Fabs described in Table 1. More specifically, the antibody or antigen binding fragments thereof may have the heavy and light sequence of Fab FF1, FF3, FF4, FF5, and FF6.

In other embodiments of the invention the antibody or antigen binding fragment that specifically binds LOX-1 comprises a heavy chain variable region CDR1, a heavy chain variable region CDR2, a heavy chain variable region CDR3, a light chain variable region CDR1, a light chain variable region CDR2, and a light chain variable region CDR3 as defined by Kabat and described in Table 1. In still other embodiments of the invention the antibody or antigen binding fragment in that specifically binds LOX-1 comprises a heavy chain variable region CDR1, a heavy chain variable region CDR2, a heavy chain variable region CDR3, a light chain variable region CDR1, a light chain variable region CDR2, and a light chain variable region CDR3 as defined by Chothia and described in Table 1.

In a specific embodiment, the invention includes an antibody that specifically binds to LOX-1 comprising a heavy chain variable region CDR1 of SEQ ID NO: 8; a heavy chain variable region CDR2 of SEQ ID NO: 9; a heavy chain variable region CDR3 of SEQ ID NO: 10; a light chain variable region CDR1 of SEQ ID NO: 18; a light chain variable region CDR2 of SEQ ID NO: 19; and a light chain variable region CDR3 of SEQ ID NO: 20.

In another specific embodiment, the invention includes an antibody that specifically binds to LOX-1 comprising a heavy chain variable region CDR1 of SEQ ID NO: 28; a heavy chain variable region CDR2 of SEQ ID NO: 29; a heavy chain variable region CDR3 of SEQ ID NO: 30; a light chain variable region CDR1 of SEQ ID NO: 38; a light chain variable region CDR2 of SEQ ID NO: 39; and a light chain variable region CDR3 of SEQ ID NO: 40.

In another specific embodiment, the invention includes an antibody that specifically binds to LOX-1 comprising a heavy chain variable region CDR1 of SEQ ID NO: 48; a heavy chain variable region CDR2 of SEQ ID NO: 49; a heavy chain variable region CDR3 of SEQ ID NO: 50; a light chain variable region CDR1 of SEQ ID NO: 58; a light chain variable region CDR2 of SEQ ID NO: 59; and a light chain variable region CDR3 of SEQ ID NO: 60.

In another specific embodiment, the invention includes an antibody that specifically binds to LOX-1 comprising a heavy chain variable region CDR1 of SEQ ID NO: 68; a heavy chain variable region CDR2 of SEQ ID NO: 69; a heavy chain variable region CDR3 of SEQ ID NO: 70; a light chain variable region CDR1 of SEQ ID NO: 78; a light chain variable region CDR2 of SEQ ID NO: 79; and a light chain variable region CDR3 of SEQ ID NO: 80.

In another specific embodiment, the invention includes an antibody that specifically binds to LOX-1 comprising a heavy chain variable region CDR1 of SEQ ID NO: 88; a heavy chain variable region CDR2 of SEQ ID NO: 89; a heavy chain variable region CDR3 of SEQ ID NO: 90; a light chain variable region CDR1 of SEQ ID NO: 98; a light chain variable region CDR2 of SEQ ID NO: 99; and a light chain variable region CDR3 of SEQ ID NO: 100.

In another specific embodiment, the invention includes an antibody that specifically binds to LOX-1 comprising a heavy chain variable region CDR1 of SEQ ID NO: 11; a heavy chain variable region CDR2 of SEQ ID NO: 12; a heavy chain variable region CDR3 of SEQ ID NO: 13; a light chain variable region CDR1 of SEQ ID NO: 21; a light chain variable region CDR2 of SEQ ID NO: 22; and a light chain variable region CDR3 of SEQ ID NO: 23.

In another specific embodiment, the invention includes an antibody that specifically binds to LOX-1 comprising a heavy chain variable region CDR1 of SEQ ID NO: 31; a heavy chain variable region CDR2 of SEQ ID NO: 32; a heavy chain variable region CDR3 of SEQ ID NO: 33; a light chain variable region CDR1 of SEQ ID NO: 41; a light chain variable region CDR2 of SEQ ID NO: 42; and a light chain variable region CDR3 of SEQ ID NO: 43.

In another specific embodiment, the invention includes an antibody that specifically binds to LOX-1 comprising a heavy chain variable region CDR1 of SEQ ID NO: 51; a heavy chain variable region CDR2 of SEQ ID NO: 52; a heavy chain variable region CDR3 of SEQ ID NO: 53; a light chain variable region CDR1 of SEQ ID NO: 61; a light chain variable region CDR2 of SEQ ID NO: 62; and a light chain variable region CDR3 of SEQ ID NO: 63.

In another specific embodiment, the invention includes an antibody that specifically binds to LOX-1 comprising a heavy chain variable region CDR1 of SEQ ID NO: 71; a heavy chain variable region CDR2 of SEQ ID NO: 72; a heavy chain variable region CDR3 of SEQ ID NO: 73; a light chain variable region CDR1 of SEQ ID NO: 81; a light chain variable region CDR2 of SEQ ID NO: 82; and a light chain variable region CDR3 of SEQ ID NO: 83.

In another specific embodiment, the invention includes an antibody that specifically binds to LOX-1 comprising a heavy chain variable region CDR1 of SEQ ID NO: 91; a heavy chain variable region CDR2 of SEQ ID NO: 92; a heavy chain variable region CDR3 of SEQ ID NO: 93; a light chain variable region CDR1 of SEQ ID NO: 101; a light chain variable region CDR2 of SEQ ID NO: 102; and a light chain variable region CDR3 of SEQ ID NO: 103.

In certain embodiments, the invention includes antibodies or antigen binding fragments that specifically bind to LOX-1 as described in Table 1. In a preferred embodiment, the antibody, or antigen binding fragment, that binds LOX-1 is Fab FF1, FF3, FF4, FF5, and FF6.

As used herein, a human antibody comprises heavy or light chain variable regions or full length heavy or light chains that are "the product of" or "derived from" a particular germline sequence if the variable regions or full length chains of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "The product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody.

A human antibody that is "the product of" or "derived from" a particular human germline immunoglobulin sequence may contain amino acid differences as compared to the germline sequence, due to, for example, naturally occurring somatic mutations or intentional introduction of site-directed mutations. However, in the VH or VL framework regions, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 60%, 70%, 80%, 90%, or at least 95%, or even at least 96%, 97%, 98%, or 99% identical in amino acid sequence to the amino acid sequence encoded by the germline immunoglobulin gene.

Typically, a recombinant human antibody will display no more than 10 amino acid differences from the amino acid sequence encoded by the human germline immunoglobulin gene in the VH or VL framework regions. In certain cases, the human antibody may display no more than 5, or even no more than 4, 3, 2, or 1 amino acid difference from the amino acid sequence encoded by the germline immunoglobulin gene. Examples of human germline immunoglobulin genes include, but are not limited to the variable domain germline fragments described below, as well as DP47 and DPK9.

Homologous Antibodies

In yet another embodiment, the present invention provides an antibody, or an antigen binding fragment thereof, comprising amino acid sequences that are homologous to the sequences described in Table 1, and the antibody binds to a LOX-1 protein (e.g., human and cynomolgus monkey LOX-1), and retains the desired functional properties of those antibodies described in Table 1.

For example, the invention provides an isolated antibody, or a functional antigen binding fragment thereof, comprising a heavy chain variable domain and a light chain variable domain, wherein the heavy chain variable domain comprises an amino acid sequence that is at least 80%, at least 90%, or at least 95% identical to an amino acid sequence selected from the group consisting of SEQ ID NOs: 14, 34, 54, 74, or 94; the light chain variable domain comprises an amino acid sequence that is at least 80%, at least 90%, or at least 95% identical to an amino acid sequence selected from the group consisting of SEQ ID NOs: 24, 44, 64, 84, or 104; and the antibody specifically binds to LOX-1 (e.g., human and cynomolgus monkey LOX-1). In certain aspects of the invention the heavy and light chain sequences further comprise HCDR1, HCDR2, HCDR3, LCDR1, LCDR2, and LCDR3 sequences as defined by Kabat, for example SEQ ID NOs: 8, 9, 10, 18, 19, and 20, respectively. In certain other aspects of the invention the heavy and light chain sequences further comprise HCDR1, HCDR2, HCDR3, LCDR1, LCDR2, and LCDR3 sequences as defined by Chothia, for example SEQ ID NOs: 11, 12, 13, 21, 22, and 23, respectively.

In other embodiments, the VH and/or VL amino acid sequences may be 50%, 60%, 70%, 80%, 90%, 95%, 96%, 97%, 98% or 99% identical to the sequences set forth in Table 1. In other embodiments, the VH and/or VL amino acid sequences may be identical except for an amino acid substitution in no more than 1, 2, 3, 4 or 5 amino acid positions. An antibody having VH and VL regions having high (i.e., 80% or greater) identity to the VH and VL regions of those described in Table 1 can be obtained by mutagenesis (e.g., site-directed or PCR-mediated mutagenesis) of nucleic acid molecules encoding SEQ ID NOs: 15, 35, 55, 75, or 95 and SEQ ID NOs: 25, 45, 65, 85, or 105, respectively, followed by testing of the encoded altered antibody for retained function using the functional assays described herein.

In other embodiments, the full length heavy chain and/or full length light chain amino acid sequences may be 50% 60%, 70%, 80%, 90%, 95%, 96%, 97%, 98% or 99% identical to the sequences set forth in Table 1. An antibody having a full length heavy chain and full length light chain having high (i.e., 80% or greater) identity to the full length heavy chains of any of SEQ ID NOs: 16, 36, 56, 76, or 96, and full length light chains of any of SEQ ID NOs: 26, 46, 66, 86, or 106, can be obtained by mutagenesis (e.g., site-directed or PCR-mediated mutagenesis) of nucleic acid molecules encoding such polypeptides, followed by testing of the encoded altered antibody for retained function using the functional assays described herein.

In other embodiments, the full length heavy chain and/or full length light chain nucleotide sequences may be 60%, 70%, 80%, 90%, 95%, 96%, 97%, 98% or 99% identical to the sequences set forth in Table 1.

In other embodiments, the variable regions of heavy chain and/or the variable regions of light chain nucleotide sequences may be 60%, 70%, 80%, 90%, 95%, 96%, 97%, 98% or 99% identical to the sequences set forth in Table 1.

As used herein, the percent identity between the two sequences is a function of the number of identical positions shared by the sequences (i.e., % identity equals number of identical positions/total number of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

Additionally or alternatively, the protein sequences of the present invention can further be used as a "query sequence" to perform a search against public databases to, for example, identify related sequences. For example, such searches can be performed using the BLAST program (version 2.0) of Altschul, et al., 1990 J. Mol. Biol. 215:403-10.

Antibodies with Conservative Modifications

In certain embodiments, an antibody of the invention has a heavy chain variable region comprising CDR1, CDR2, and CDR3 sequences and a light chain variable region comprising CDR1, CDR2, and CDR3 sequences, wherein one or more of these CDR sequences have specified amino acid sequences based on the antibodies described herein or conservative modifications thereof, and wherein the antibodies retain the desired functional properties of the LOX-1-binding antibodies of the invention.

Accordingly, the invention provides an isolated antibody, or a antigen binding fragment thereof, consisting of a heavy chain variable region comprising CDR1, CDR2, and CDR3 sequences and a light chain variable region comprising CDR1, CDR2, and CDR3 sequences, wherein: the heavy chain variable region CDR1 amino acid sequences are selected from the group consisting of SEQ ID NOs: 8, 28, 48, 68, and 88, and conservative modifications thereof; the heavy chain variable region CDR2 amino acid sequences are selected from the group consisting of SEQ ID NOs: 9, 29, 49, 69, and 89, and conservative modifications thereof; the heavy chain variable region CDR3 amino acid sequences are selected from the group consisting of SEQ ID NOs: 10, 30, 50, 70, and 90, and conservative modifications thereof; the light chain variable regions CDR1 amino acid sequences are selected from the group consisting of SEQ ID NOs: 18, 38, 58, 78, and 98, and conservative modifications thereof; the light chain variable regions CDR2 amino acid sequences are selected from the group consisting of SEQ ID NOs: 19, 39, 59, 79, and 99, and conservative modifications thereof; the light chain variable regions of CDR3 amino acid sequences are selected from the group consisting of SEQ ID NOs: 20, 40, 60, 80, and 100, and conservative modifications thereof; and the antibody or antigen binding fragments thereof specifically binds to LOX-1.

In other embodiments, the antibody of the invention is optimized for expression in a mammalian cell has a full length heavy chain sequence and a full length light chain sequence, wherein one or more of these sequences have specified amino acid sequences based on the antibodies described herein or conservative modifications thereof, and wherein the antibodies retain the desired functional properties of the LOX-1 binding antibodies of the invention. Accordingly, the invention provides an isolated antibody optimized for expression in a mammalian cell consisting of a full length heavy chain and a full length light chain wherein the full length heavy chain has amino acid sequences selected from the group of SEQ ID NOs: 16, 36, 56, 76, or 96, and conservative modifications thereof; and the full length light chain has amino acid sequences selected from the group of SEQ ID NOs: 26, 46, 66, 86, or 106, and conservative modifications thereof; and the antibody specifically binds to LOX-1 (e.g., human and cynomolgus monkey LOX-1).

Antibodies that Bind to the Same Epitope

The present invention provides antibodies that bind to the same epitope as the LOX-1 binding antibodies described in Table 1. Additional antibodies can therefore be identified based on their ability to compete (e.g., to competitively inhibit the binding of, in a statistically significant manner) with other antibodies of the invention in LOX-1 binding assays (such as those described in the Examples). The ability of a test antibody to inhibit the binding of antibodies of the present invention to a LOX-1 protein demonstrates that the test antibody can compete with that antibody for binding to LOX-1; such an antibody may, according to non-limiting theory, bind to the same or a related (e.g., a structurally similar or spatially proximal) epitope on the LOX-1 protein as the antibody with which it competes. In a certain embodiment, the antibody that binds to the same epitope on LOX-1 as the antibodies of the present invention is a human monoclonal antibody. Such human monoclonal antibodies can be prepared and isolated as described herein. As used herein, an antibody "competes" for binding when the competing antibody inhibits LOX-1 binding of an antibody or antigen binding fragment of the invention by more than 50% (for example, 80%, 85%, 90%, 95%, 98% or 99%) in the presence of an equimolar concentration of competing antibody.

In other embodiments the antibodies or antigen binding fragments of the invention bind the LOX-1 C terminus lectin-like domain (oxLDL binding domain), more specifically to an epitope comprising amino acid residues 228-246 from human LOX-1 (FRVRGAVSQTYPSGTCAYI; SEQ ID NO:3). In certain embodiments, the antibodies or antigen binding fragments of the invention bind an epitope on human LOX-1 comprising amino acid residues Arg229 and Arg231 of human LOX-1 (SEQ ID NO:1).

Engineered and Modified Antibodies

An antibody of the invention further can be prepared using an antibody having one or more of the VH and/or VL sequences shown herein as starting material to engineer a modified antibody, which modified antibody may have altered properties from the starting antibody. An antibody can be engineered by modifying one or more residues within one or both variable regions (i.e., VH and/or VL), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al., 1998 Nature 332:323-327; Jones, P. et al., 1986 Nature 321:522-525; Queen, C. et al., 1989 Proc. Natl. Acad., U.S.A. 86:10029-10033; U.S. Pat. No. 5,225,539 to Winter, and U.S. Pat. Nos. 5,530,101; 5,585,089; 5,693,762 and 6,180,370 to Queen et al.)

Accordingly, another embodiment of the invention pertains to an isolated antibody, or an antigen binding fragment thereof, comprising a heavy chain variable region comprising CDR1 sequences having an amino acid sequence selected from the group consisting of SEQ ID NOs: 8, 28, 48, 68, and 88; CDR2 sequences having an amino acid sequence selected from the group consisting of SEQ ID NOs: 9, 29, 49, 69, and 89; CDR3 sequences having an amino acid sequence selected from the group consisting of SEQ ID NOs: 10, 30, 50, 70, and 90, respectively; and a light chain variable region having CDR1 sequences having an amino acid sequence selected from the group consisting of SEQ ID NOs: 18, 38, 58, 78, and 98; CDR2 sequences having an amino acid sequence selected from the group consisting of SEQ ID NOs: 19, 39, 59, 79, and 99; and CDR3 sequences consisting of an amino acid sequence selected from the group consisting of SEQ ID NOs: 20, 40, 60, 80, and 100, respectively. Thus, such antibodies contain the VH and VL CDR sequences of monoclonal antibodies, yet may contain different framework sequences from these antibodies.

Such framework sequences can be obtained from public DNA databases or published references that include germline antibody gene sequences. For example, germline DNA sequences for human heavy and light chain variable region genes can be found in the "VBase" human germline sequence database (available on the world wide web at mrc-cpe.cam.ac.uk/vbase), as well as in Kabat, E. A., et al., 1991 Sequences of Proteins of Immunological Interest, Fifth Edition, U.S. Department of Health and Human Services, NIH Publication No. 91-3242; Tomlinson, I. M., et al., 1992 J. Mol. Biol. 227:776-798; and Cox, J. P. L. et al., 1994 Eur. J Immunol. 24:827-836; the contents of each of which are expressly incorporated herein by reference.

An example of framework sequences for use in the antibodies of the invention are those that are structurally similar to the framework sequences used by selected antibodies of the invention, e.g., consensus sequences and/or framework sequences used by monoclonal antibodies of the invention. The VH CDR1, 2 and 3 sequences, and the VL CDR1, 2 and 3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al). Frameworks that can be utilized as scaffolds on which to build the antibodies and antigen binding fragments described herein include, but are not limited to VH1A, VH1B, VH3, Vk1, Vl2, and Vk2. Additional frameworks are known in the art and may be found, for example, in the vBase data base on the world wide web at vbase.mrc-cpe.cam.ac.uk/index.php?&MMN_position=1:1.

Accordingly, an embodiment of the invention relates to isolated LOX-1 binding antibodies, or antigen binding fragments thereof, comprising a heavy chain variable region comprising an amino acid sequence selected from the group consisting of SEQ ID NOs: 14, 34, 54, 74, or 94, or an amino acid sequence having one, two, three, four or five amino acid substitutions, deletions or additions in the framework region of such sequences, and further comprising a light chain variable region having an amino acid sequence selected from the group consisting of SEQ ID NOs: 24, 44, 64, 84, or 104, or an amino acid sequence having one, two, three, four or five amino acid substitutions, deletions or additions in the framework region of such sequences.

Another type of variable region modification is to mutate amino acid residues within the VH and/or VL CDR1, CDR2 and/or CDR3 regions to thereby improve one or more binding properties (age affinity) of the antibody of interest, known as "affinity maturation." Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Conservative modifications as discussed above) can be introduced. The mutations may be amino acid substitutions, additions or deletions. Moreover, typically no more than one, two, three, four or five residues within a CDR region are altered.

Accordingly, in another embodiment, the invention provides isolated LOX-1-binding antibodies, or antigen binding fragments thereof, consisting of a heavy chain variable region having a VH CDR1 region consisting of an amino acid sequence selected from the group having SEQ ID NOs: 8, 28, 48, 68, and 88 or an amino acid sequence having one, two, three, four or five amino acid substitutions, deletions or additions as compared to SEQ ID NOs: 8, 28, 48, 68, and 88; a VH CDR2 region having an amino acid sequence selected from the group consisting of SEQ ID NOs: 9, 29, 49, 69, and 89 or an amino acid sequence having one, two, three, four or five amino acid substitutions, deletions or additions as compared to SEQ ID NOs: 9, 29, 49, 69, and 89; a VH CDR3 region having an amino acid sequence selected from the group consisting of SEQ ID NOs: 10, 30, 50, 70, and 90, or an amino acid sequence having one, two, three, four or five amino acid substitutions, deletions or additions as compared to SEQ ID NOs: 10, 30, 50, 70, and 90; a VL CDR1 region having an amino acid sequence selected from the group consisting of SEQ ID NOs: 18, 38, 58, 78, and 98, or an amino acid sequence having one, two, three, four or five amino acid substitutions, deletions or additions as compared to SEQ ID NOs: 18, 38, 58, 78, and 98; a VL CDR2 region having an amino acid sequence selected from the group consisting of SEQ ID NOs: 19, 39, 59, 79, and 99, or an amino acid sequence having one, two, three, four or five amino acid substitutions, deletions or additions as compared to SEQ ID NOs: 19, 39, 59, 79, and 99; and a VL CDR3 region having an amino acid sequence selected from the group consisting of SEQ ID NOs: 20, 40, 60, 80, and 100, or an amino acid sequence having one, two, three, four or five amino acid substitutions, deletions or additions as compared to SEQ ID NOs: 20, 40, 60, 80, and 100.

Accordingly, in another embodiment, the invention provides isolated LOX-1-binding antibodies, or antigen binding fragments thereof, consisting of a heavy chain variable region having a VH CDR1 region consisting of an amino acid sequence selected from the group having SEQ ID NOs: 11, 31, 51, 71, and 91 or an amino acid sequence having one, two, three, four or five amino acid substitutions, deletions or additions as compared to SEQ ID NOs: 11, 31, 51, 71, and 91; a VH CDR2 region having an amino acid sequence selected from the group consisting of SEQ ID NOs: 12, 32, 52, 72, and 92 or an amino acid sequence having one, two, three, four or five amino acid substitutions, deletions or additions as compared to SEQ ID NOs: 12, 32, 52, 72, and 92; a VH CDR3 region having an amino acid sequence selected from the group consisting of SEQ ID NOs: 13, 33, 53, 73, and 93, or an amino acid sequence having one, two, three, four or five amino acid substitutions, deletions or additions as compared to SEQ ID NOs: 13, 33, 53, 73, and 93; a VL CDR1 region having an amino acid sequence selected from the group consisting of SEQ ID NOs: 21, 41, 61, 81, and 101, or an amino acid sequence having one, two, three, four or five amino acid substitutions, deletions or additions as compared to SEQ ID NOs: 21, 41, 61, 81, and 101; a VL CDR2 region having an amino acid sequence selected from the group consisting of SEQ ID NOs: 22, 42, 62, 82, and 102, or an amino acid sequence having one, two, three, four or five amino acid substitutions, deletions or additions as compared to SEQ ID NOs: 22, 42, 62, 82, and 102; and a VL CDR3 region having an amino acid sequence selected from the group consisting of SEQ ID NOs: 23, 43, 63, 83, and 103, or an amino acid sequence having one, two, three, four or five amino acid substitutions, deletions or additions as compared to SEQ ID NOs: 23, 43, 63, 83, and 103.

Grafting Antigen-Binding Domains into Alternative Frameworks or Scaffolds

A wide variety of antibody/immunoglobulin frameworks or scaffolds can be employed so long as the resulting polypeptide includes at least one binding region which specifically binds to LOX-1. Such frameworks or scaffolds include the 5 main idiotypes of human immunoglobulins, or fragments thereof, and include immunoglobulins of other animal species, preferably having humanized aspects. Single heavy-chain antibodies such as those identified in camelids are of particular interest in this regard. Novel frameworks, scaffolds and fragments continue to be discovered and developed by those skilled in the art.

In one aspect, the invention pertains to generating non-immunoglobulin based antibodies using non-immunoglobulin scaffolds onto which CDRs of the invention can be grafted. Known or future non-immunoglobulin frameworks and scaffolds may be employed, as long as they comprise a binding region specific for the target LOX-1 protein. Known non-immunoglobulin frameworks or scaffolds include, but are not limited to, fibronectin (Compound Therapeutics, Inc., Waltham, Mass.), ankyrin (Molecular Partners AG, Zurich, Switzerland), domain antibodies (Domantis, Ltd., Cambridge, Mass., and Ablynx nv, Zwijnaarde, Belgium), lipocalin (Pieris Proteolab AG, Freising, Germany), small modular immuno-pharmaceuticals (Trubion Pharmaceuticals Inc., Seattle, Wash.), maxybodies (Avidin, Inc., Mountain View, Calif.). Protein A (Affibody AG, Sweden), and affilin (gamma-crystallin or ubiquitin) (SciI Proteins GmbH, Halle, Germany).

The fibronectin scaffolds are based on fibronectin type III domain (e.g., the tenth module of the fibronectin type III (10 Fn3 domain)). The fibronectin type III domain has 7 or 8 beta strands which are distributed between two beta sheets, which themselves pack against each other to form the core of the protein, and further containing loops (analogous to CDRs) which connect the beta strands to each other and are solvent exposed. There are at least three such loops at each edge of the beta sheet sandwich, where the edge is the boundary of the protein perpendicular to the direction of the beta strands (see U.S. Pat. No. 6,818,418). These fibronectin-based scaffolds are not an immunoglobulin, although the overall fold is closely related to that of the smallest functional antibody fragment, the variable region of the heavy chain, which comprises the entire antigen recognition unit in camel and llama IgG. Because of this structure, the non-immunoglobulin antibody mimics antigen binding properties that are similar in nature and affinity to those of antibodies. These scaffolds can be used in a loop randomization and shuffling strategy in vitro that is similar to the process of affinity maturation of antibodies in vivo. These fibronectin-based molecules can be used as scaffolds where the loop regions of the molecule can be replaced with CDRs of the invention using standard cloning techniques.

The ankyrin technology is based on using proteins with ankyrin derived repeat modules as scaffolds for bearing variable regions which can be used for binding to different targets. The ankyrin repeat module is a 33 amino acid polypeptide consisting of two anti-parallel α-helices and a β-turn. Binding of the variable regions is mostly optimized by using ribosome display.

Avimers are derived from natural A-domain containing protein such as LRP-1. These domains are used by nature for protein-protein interactions and in human over 250 proteins are structurally based on A-domains. Avimers consist of a number of different "A-domain" monomers (2-10) linked via amino acid linkers. Avimers can be created that can bind to the target antigen using the methodology described in, for example, U.S. Patent Application Publication Nos. 20040175756; 20050053973; 20050048512; and 20060008844.

Affibody affinity ligands are small, simple proteins composed of a three-helix bundle based on the scaffold of one of the IgG-binding domains of Protein A. Protein A is a surface protein from the bacterium *Staphylococcus aureus*. This scaffold domain consists of 58 amino acids, 13 of which are randomized to generate affibody libraries with a large number of ligand variants (See e.g., U.S. Pat. No. 5,831,012). Affibody molecules mimic antibodies, they have a molecular weight of 6 kDa, compared to the molecular weight of antibodies, which is 150 kDa. In spite of its small size, the binding site of affibody molecules is similar to that of an antibody.

Anticalins are products developed by the company Pieris ProteoLab AG. They are derived from lipocalins, a widespread group of small and robust proteins that are usually involved in the physiological transport or storage of chemically sensitive or insoluble compounds. Several natural lipocalins occur in human tissues or body liquids. The protein architecture is reminiscent of immunoglobulins, with hypervariable loops on top of a rigid framework. However, in contrast with antibodies or their recombinant fragments, lipocalins are composed of a single polypeptide chain with 160 to 180 amino acid residues, being just marginally bigger than a single immunoglobulin domain. The set of four loops, which makes up the binding pocket, shows pronounced structural plasticity and tolerates a variety of side chains. The binding site can thus be reshaped in a proprietary process in order to recognize prescribed target molecules of different shape with high affinity and specificity. One protein of lipocalin family, the bilin-binding protein (BBP) of *Pieris Brassicae* has been used to develop anticalins by mutagenizing the set of four loops. One example of a patent application describing anticalins is in PCT Publication No. WO 199916873.

Affilin molecules are small non-immunoglobulin proteins which are designed for specific affinities towards proteins and small molecules. New affilin molecules can be very quickly selected from two libraries, each of which is based on a different human derived scaffold protein. Affilin molecules do not show any structural homology to immunoglobulin proteins. Currently, two affilin scaffolds are employed, one of which is gamma crystalline, a human structural eye lens protein and the other is "ubiquitin" superfamily proteins. Both human scaffolds are very small, show high temperature stability and are almost resistant to pH changes and denaturing agents. This high stability is mainly due to the expanded beta sheet structure of the proteins. Examples of gamma crystalline derived proteins are described in WO200104144 and examples of "ubiquitin-like" proteins are described in WO2004106368.

Protein epitope mimetics (PEM) are medium-sized, cyclic, peptide-like molecules (MW 1-2 kDa) mimicking beta-hairpin secondary structures of proteins, the major secondary structure involved in protein-protein interactions.

The present invention provides fully human antibodies that specifically bind to a LOX-1 protein. Compared to the chimeric or humanized antibodies, the human LOX-1-binding antibodies of the invention have further reduced antigenicity when administered to human subjects.

Camelid Antibodies

Antibody proteins obtained from members of the camel and dromedary (*Camelus bactrianus* and *Calelus dromaderius*) family including new world members such as *llama* species (*Lama paccos, Lama glama* and *Lama vicugna*) have been characterized with respect to size, structural complexity and antigenicity for human subjects. Certain IgG antibodies from this family of mammals as found in nature lack light chains, and are thus structurally distinct from the typical four chain quaternary structure having two heavy and two light chains, for antibodies from other animals. See PCT/EP93/02214 (WO 94/04678 published 3 Mar. 1994).

A region of the camelid antibody which is the small single variable domain identified as VHH can be obtained by genetic engineering to yield a small protein having high affinity for a target, resulting in a low molecular weight antibody-derived protein known as a "camelid nanobody". See U.S. Pat. No. 5,759,808 issued Jun. 2, 1998; see also Stijlemans, B. et al., 2004 J Biol Chem 279: 1256-1261; Dumoulin, M. et al., 2003 Nature 424: 783-788; Pleschberger, M. et al. 2003 Bioconjugate Chem 14: 440-448; Cortez-Retamozo, V. et al. 2002 Int J Cancer 89: 456-62; and Lauwereys, M. et al. 1998 EMBO J 17: 3512-3520. Engineered libraries of camelid antibodies and antibody fragments are commercially available, for example, from Ablynx, Ghent, Belgium. As with other antibodies of non-human origin, an amino acid sequence of a camelid antibody can be altered recombinantly to obtain a sequence that more closely resembles a human sequence, the nanobody can be "humanized". Thus the natural low antigenicity of camelid antibodies to humans can be further reduced.

The camelid nanobody has a molecular weight approximately one-tenth that of a human IgG molecule, and the protein has a physical diameter of only a few nanometers. One consequence of the small size is the ability of camelid nanobodies to bind to antigenic sites that are functionally invisible to larger antibody proteins, i.e., camelid nanobodies are useful as reagents detect antigens that are otherwise cryptic using classical immunological techniques, and as possible therapeutic agents. Thus yet another consequence of small size is that a camelid nanobody can inhibit as a result of binding to a specific site in a groove or narrow cleft of a target protein, and hence can serve in a capacity that more closely resembles the function of a classical low molecular weight drug than that of a classical antibody.

The low molecular weight and compact size further result in camelid nanobodies being extremely thermostable, stable to extreme pH and to proteolytic digestion, and poorly antigenic. Another consequence is that camelid nanobodies readily move from the circulatory system into tissues, and even cross the blood-brain barrier and can treat disorders that affect nervous tissue. Nanobodies can further facilitated drug transport across the blood brain barrier. See U.S. patent application 20040161738 published Aug. 19, 2004. These features combined with the low antigenicity to humans indicate great therapeutic potential. Further, these molecules can be fully expressed in prokaryotic cells such as *E. coli* and are expressed as fusion proteins with bacteriophage and are functional.

Accordingly, a feature of the present invention is a camelid antibody or nanobody having high affinity for LOX-1. In certain embodiments herein, the camelid antibody or nanobody is naturally produced in the camelid animal, i.e., is produced by the camelid following immunization with LOX-1 or a peptide fragment thereof, using techniques described herein for other antibodies. Alternatively, the LOX-1-binding camelid nanobody is engineered, i.e., produced by selection for example from a library of phage displaying appropriately mutagenized camelid nanobody proteins using panning procedures with LOX-1 as a target as described in the examples herein. Engineered nanobodies can further be customized by genetic engineering to have a half life in a recipient subject of from 45 minutes to two weeks. In a specific embodiment, the camelid antibody or nanobody is obtained by grafting the CDRs sequences of the heavy or light chain of the human antibodies of the invention into nanobody or single domain antibody framework sequences, as described for example in PCT/EP93/02214.

Bispecific Molecules and Multivalent Antibodies

In another aspect, the present invention features bispecific or multispecific molecules comprising a LOX-1-binding antibody, or a fragment thereof, of the invention. An antibody of the invention, or antigen-binding regions thereof, can be derivatized or linked to another functional molecule, e.g., another peptide or protein (e.g., another antibody or ligand for a receptor) to generate a bispecific molecule that binds to at least two different binding sites or target molecules. The antibody of the invention may in fact be derivatized or linked to more than one other functional molecule to generate multi-specific molecules that bind to more than two different binding sites and/or target molecules; such multi-specific molecules are also intended to be encompassed by the term "bispecific molecule" as used herein. To create a bispecific molecule of the invention, an antibody of the invention can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, the present invention includes bispecific molecules comprising at least one first binding specificity for LOX-1 and a second binding specificity for a second target epitope. For example, the second target epitope is another epitope of LOX-1 different from the first target epitope.

Additionally, for the invention in which the bispecific molecule is multi-specific, the molecule can further include a third binding specificity, in addition to the first and second target epitope.

In one embodiment, the bispecific molecules of the invention comprise as a binding specificity at least one antibody, or an antibody fragment thereof, including, e.g., a Fab, Fab', F(ab')2, Fv, or a single chain Fv. The antibody may also be a light chain or heavy chain dimer, or any minimal fragment thereof such as a Fv or a single chain construct as described in Ladner et al. U.S. Pat. No. 4,946,778.

Diabodies are bivalent, bispecific molecules in which VH and VL domains are expressed on a single polypeptide chain, connected by a linker that is too short to allow for pairing between the two domains an the same chain. The VH and VL domains pair with complementary domains of another chain, thereby creating two antigen binding sites (see e.g., Holliger et al., 1993 Proc. Natl. Acad. Sci. USA 90:6444-6448; Poljak et al., 1994 Structure 2:1121-1123). Diabodies can be produced by expressing two polypeptide chains with either the structure VHA-VLB and VHB-VLA (VH-VL configuration), or VLA-VHB and VLB-VHA (VL-VH configuration) within the same cell. Most of them can be expressed in soluble form in bacteria. Single chain diabodies (scDb) are produced by connecting the two diabody-forming polypeptide chains with linker of approximately 15 amino acid residues (see Holliger and Winter, 1997 Cancer Immunol. Immunother., 45(3-4):128-30; Wu et al., 1996 Immunotechnology, 2(1):21-36). scDb can be expressed in bacteria in soluble, active monomeric form (see Holliger and Winter, 1997 Cancer Immunol, Immunother., 45(34): 128-30; Wu et al., 1996 Immunotechnology, 2(1):21-36; Pluckthun and Pack, 1997 Immunotechnology, 3(2): 83-105; Ridgway et al., 1996 Protein Eng., 9(7):617-21). A diabody can be fused to Fc to generate a "di-diabody" (see Lu et al., 2004 J. Biol. Chem., 279(4):2856-65).

Other antibodies which can be employed in the bispecific molecules of the invention are murine, chimeric and humanized monoclonal antibodies.

Bispecific molecules can be prepared by conjugating the constituent binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohaxane-1-carboxylate (sulfo-SMCC) (see e.g., Karpovsky at al., 1984 J. Exp. Med. 160:1686; Liu, M A et al., 1985 Proc. Natl. Acad. Sci. USA 82:8648). Other methods include those described in Paulus, 1985 Behring Ins. Mitt. No. 78,118-132; Brennan et al., 1985 Science 229:81-83), and Glennie et al., 1987 J. Immunol. 139: 2367-2375). Conjugating agents are SATA and sulfo-SMCC, both available from Pierce Chemical Co. (Rockford, Ill.).

When the binding specificities are antibodies, they can be conjugated by sulfhydryl bonding of the C-terminus hinge regions of the two heavy chains. In a particularly embodiment, the hinge region is modified to contain an odd number of sulfhydryl residues, for example one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')2 or ligand×Fab fusion protein. A bispecific molecule of the invention can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. No. 5,260,203; U.S. Pat. No. 5,455,030; U.S. Pat. No. 4,881,175; U.S. Pat.

No. 5,132,405; U.S. Pat. No. 5,091,513; U.S. Pat. No. 5,476,786; U.S. Pat. No. 5,013,653; U.S. Pat. No. 5,258,498; and U.S. Pat. No. 5,482,858.

Binding of the bispecific molecules to their specific targets can be confirmed by, for example, enzyme-linked immunosorbent assay (ELISA), radioimmunoassay (REA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest.

In another aspect, the present invention provides multivalent compounds comprising at least two identical or different antigen-binding portions of the antibodies of the invention binding to LOX-1. The antigen-binding portions can be linked together via protein fusion or covalent or non covalent linkage. Alternatively, methods of linkage have been described for the bispecific molecules. Tetravalent compounds can be obtained for example by cross-linking antibodies of the antibodies of the invention with an antibody that binds to the constant regions of the antibodies of the invention, for example the Fe or hinge region.

Trimerizing domain are described for example in Borean patent EP 1 012 28061. Pentamerizing modules are described for example in PCT/EP97/05897.

Antibodies with Extended Half Life

The present invention provides for antibodies that specifically bind to LOX-1 protein which have an extended half-life in vivo.

Many factors may affect a protein's half life in vivo. For examples, kidney filtration, metabolism in the liver, degradation by proteolytic enzymes (proteases), and immunogenic responses (e.g., protein neutralization by antibodies and uptake by macrophages and dendritic cells). A variety of strategies can be used to extend the half life of the antibodies of the present invention. For example, by chemical linkage to polyethyleneglycol (PEG), reCODE PEG, antibody scaffold, polysialic acid (PSA), hydroxyethyl starch (HES), albumin-binding ligands, and carbohydrate shields; by genetic fusion to proteins binding to serum proteins, such as albumin, IgG, FcRn, and transferring; by coupling (genetically or chemically) to other binding moieties that bind to serum proteins, such as nanobodies, Fabs, DARPins, avimers, affibodies, and anticalins; by genetic fusion to rPEG, albumin, domain of albumin, albumin-binding proteins, and Fc; or by incorporation into nanocarriers, slow release formulations, or medical devices.

To prolong the serum circulation of antibodies in vivo, inert polymer molecules such as high molecular weight PEG can be attached to the antibodies or a fragment thereof with or without a multifunctional linker either through site-specific conjugation of the PEG to the N- or C-terminus of the antibodies or via epsilon-amino groups present on lysine residues. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Linear or branched polymer derivatization that results in minimal loss of biological activity will be used. The degree of conjugation can be closely monitored by SDS-PAGE and mass spectrometry to ensure proper conjugation of PEG molecules to the antibodies. Unreacted PEG can be separated from antibody-PEG conjugates by size-exclusion or by ion-exchange chromatography, PEG-derivatized antibodies can be tested for binding activity as well as for in vivo efficacy using methods well-known to those of skill in the art, for example, by immunoassays described herein. Methods for pegylating proteins are known in the art and can be applied to the antibodies of the invention. See for example, EP 0 154 316 by Nishimura et al. and EP 0 401 384 by Ishikawa et al.

Other modified pegylation technologies include reconstituting chemically orthogonal directed engineering technology (ReCODE PEG), which incorporates chemically specified side chains into biosynthetic proteins via a reconstituted system that includes tRNA synthetase and tRNA. This technology enables incorporation of more than 30 new amino acids into biosynthetic proteins in *E. coli*, yeast, and mammalian cells. The tRNA incorporates a nonnative amino acid any place an amber codon is positioned, converting the amber from a stop codon to one that signals incorporation of the chemically specified amino acid.

Recombinant pegylation technology (rPEG) can also be used for serum halflife extension. This technology involves genetically fusing a 300-600 amino acid unstructured protein tail to an existing pharmaceutical protein. Because the apparent molecular weight of such an unstructured protein chain is about 15-fold larger than its actual molecular weight, the serum halflife of the protein is greatly increased. In contrast to traditional PEGylation, which requires chemical conjugation and repurification, the manufacturing process is greatly simplified and the product is homogeneous.

Polysialytion is another technology, which uses the natural polymer polysialic acid (PSA) to prolong the active life and improve the stability of therapeutic peptides and proteins. PSA is a polymer of sialic acid (a sugar). When used for protein and therapeutic peptide drug delivery, polysialic acid provides a protective microenvironment on conjugation. This increases the active life of the therapeutic protein in the circulation and prevents it from being recognized by the immune system. The PSA polymer is naturally found in the human body. It was adopted by certain bacteria which evolved over millions of years to coat their walls with it. These naturally polysialylated bacteria were then able, by virtue of molecular mimicry, to foil the body's defense system. PSA, nature's ultimate stealth technology, can be easily produced from such bacteria in large quantities and with predetermined physical characteristics. Bacterial PSA is completely non-immunogenic, even when coupled to proteins, as it is chemically identical to PSA in the human body.

Another technology includes the use of hydroxyethyl starch ("HES") derivatives linked to antibodies. HES is a modified natural polymer derived from waxy maize starch and can be metabolized by the body's enzymes. HES solutions are usually administered to substitute deficient blood volume and to improve the rheological properties of the blood. Hesylation of an antibody enables the prolongation of the circulation half-life by increasing the stability of the molecule, as well as by reducing renal clearance, resulting in an increased biological activity. By varying different parameters, such as the molecular weight of HES, a wide range of HES antibody conjugates can be customized.

Antibodies having an increased half-life in viva can also be generated introducing one or more amino acid modifications (i.e., substitutions, insertions or deletions) into an IgG constant domain, or FcRn binding fragment thereof (preferably a Fe or hinge Fe domain fragment). See, e.g., International Publication No. WO 98/23289; International Publication No. WO 97/34631; and U.S. Pat. No. 6,277,375.

Further, antibodies can be conjugated to albumin (e.g., human serum albumin; HSA) in order to make the antibody or antibody fragment more stable in vivo or have a longer half life in vivo. The techniques are well-known in the art, see, e.g., International Publication Nos. WO 93/15199, WO 93/15200, and WO 01/77137; and European Patent No. EP 413,622. In addition, in the context of a bispecific antibody as described above, the specificities of the antibody can be designed such that one binding domain of the antibody binds to LOX-1 while a second binding domain of the antibody binds to serum albumin, preferably HSA.

The strategies for increasing half life is especially useful in nanobodies, fibronectin-based binders, and other antibodies or proteins for which increased in vivo half life is desired.

Antibody Conjugates

The present invention provides antibodies or fragments thereof that specifically bind to a LOX-1 protein recombinantly fused or chemically conjugated (including both covalent and non-covalent conjugations) to a heterologous protein or polypeptide (or fragment thereof, preferably to a polypeptide of at least 10, at least 20, at least 30, at least 40, at least 50, at least 60, at least 70, at least 80, at least 90 or at least 100 amino acids) to generate fusion proteins. In particular, the invention provides fusion proteins comprising an antigen-binding fragment of an antibody described herein (e.g., a Fab fragment, Fd fragment, Fv fragment, F(ab)2 fragment, a VH domain, a VH CDR, a VL domain or a VL CDR) and a heterologous protein, polypeptide, or peptide. Methods for fusing or conjugating proteins, polypeptides, or peptides to an antibody or an antibody fragment are known in the art. See, e.g., U.S. Pat. Nos. 5,336,603, 5,622,929, 5,359,046, 5,349,053, 5,447,851, and 5,112,946; European Patent Nos. EP 307,434 and EP 367,166; International Publication Nos. WO 96/04388 and WO 91/06570; Ashkenazi et al., 1991, Proc. Natl. Acad. Sci. USA 88: 10535-10539; Zheng et al., 1995, J. Immunol. 154:5590-5600; and Vil et al., 1992, Proc. Natl. Acad. Sci. USA 89:11337-11341.

Additional fusion proteins may be generated through the techniques of gene-shuffling, motif-shuffling, exon-shuffling, and/or codon-shuffling (collectively referred to as "DNA shuffling"), DNA shuffling may be employed to alter the activities of antibodies of the invention or fragments thereof (e.g., antibodies or fragments thereof with higher affinities and lower dissociation rates). See, generally, U.S. Pat. Nos. 5,605,793, 5,811,238, 5,830,721, 5,834,252, and 5,837,458; Patten et al., 1997, Curr. Opinion Biotechnol. 8:724-33; Harayama, 1998, Trends Biotechnol. 16(2):76-82; Hansson, et al., 1999, J. Mol. Biol. 287:265-76; and Lorenzo and Blasco, 1998, Biotechniques 24(2):308-313 (each of these patents and publications are hereby incorporated by reference in its entirety). Antibodies or fragments thereof, or the encoded antibodies or fragments thereof, may be altered by being subjected to random mutagenesis by error-prone PCR, random nucleotide insertion or other methods prior to recombination. A polynucleotide encoding an antibody or fragment thereof that specifically binds to a LOX-1 protein may be recombined with one or more components, motifs, sections, parts, domains, fragments, etc. of one or more heterologous molecules.

Moreover, the antibodies or fragments thereof can be fused to marker sequences, such as a peptide to facilitate purification. In preferred embodiments, the marker amino acid sequence is a hexa-histidine peptide, such as the tag provided in a ROE vector (QIAGEN, Inc., 9259 Eton Avenue, Chatsworth, Calif., 91311), among others, many of which are commercially available. As described in Gentz et al., 1989, Proc. Natl. Acad. Sci. USA 86:821-824, for instance, hexa-histidine provides for convenient purification of the fusion protein. Other peptide tags useful for purification include, but are not limited to, the hemagglutinin ("HA") tag, which corresponds to an epitope derived from the influenza hemagglutinin protein (Wilson et al., 1984, Cell 37:767), and the "flag" tag.

In other embodiments, antibodies of the present invention or fragments thereof conjugated to a diagnostic or detectable agent. Such antibodies can be useful for monitoring or prognosing the onset, development, progression and/or severity of a disease or disorder as part of a clinical testing procedure, such as determining the efficacy of a particular therapy. Such diagnosis and detection can accomplished by coupling the antibody to detectable substances including, but not limited to, various enzymes, such as, but not limited to, horseradish peroxidase, alkaline phosphatase, beta-galactosidase, or acetylcholinesterase; prosthetic groups, such as, but not limited to, streptavidinlbiotin and avidin/biotin; fluorescent materials, such as, but not limited to, umbelliferone, fluorescein, fluorescein isothiocynate, rhodamine, dichlorotriazinylamine fluorescein, dansyl chloride or phycoerythrin; luminescent materials, such as, but not limited to, luminal; bioluminescent materials, such as but not limited to, luciferase, luciferin, and aequorin; radioactive materials, such as, but not limited to, iodine (131I, 125I, 123I, and 121I,), carbon (14C), sulfur (35S), tritium (3H), indium (115In, 113In, 112In, and 111In,), technetium (99Tc), thallium (201Ti), gallium (68Ga, 67Ga), palladium (103Pd), molybdenum (99Mo), xenon (133Xe), fluorine (18F), 153Sm, 177Lu, 159Gd, 149Pm, 140La, 175Yb, 166Ho, 90Y, 47Sc, 186Re, 188Re, 142 Pr, 105Rh, 97Ru, 68Ge, 57Co, 65Zn, 85Sr, 32P, 153Gd, 169Yb, 51Cr, 54Mn, 75Se, 113Sn, and 117Tin; and positron emitting metals using various positron emission tomographies, and nonradioactive paramagnetic metal ions.

The present invention further encompasses uses of antibodies or fragments thereof conjugated to a therapeutic moiety. An antibody or fragment thereof may be conjugated to a therapeutic moiety such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells.

Further, an antibody or fragment thereof may be conjugated to a therapeutic moiety or drug moiety that modifies a given biological response. Therapeutic moieties or drug moieties are not to be construed as limited to classical chemical therapeutic agents. For example, the drug moiety may be a protein, peptide, or polypeptide possessing a desired biological activity. Such proteins may include, for example, a toxin such as abrin, ricin A, *pseudomonas* exotoxin, cholera toxin, or diphtheria toxin; a protein such as tumor necrosis factor, α-interferon, β-interferon, nerve growth factor, platelet derived growth factor, tissue plasminogen activator, an apoptotic agent, an anti-angiogenic agent; or, a biological response modifier such as, for example, a lymphokine.

Moreover, an antibody can be conjugated to therapeutic moieties such as a radioactive metal ion, such as alpha-emitters such as 213Bi or macrocyclic chelators useful for conjugating radiometal ions, including but not limited to, 131In, 131LU, 131Y, 131Ho, 131Sm, to polypeptides. In certain embodiments, the macrocyclic chelator is 1,4,7,10- tetraazacyclododecane-N,N',N",N'"-tetraacetic acid (DOTA) which can be attached to the antibody via a linker molecule. Such linker molecules are commonly known in the art and described in Denardo et al., 1998, Clin Cancer Res, 4(10):2483-90; Peterson et al., 1999, Bioconjug. Chem. 10(4):553-7; and Zimmerman et al., 1999, Nucl. Med. Biol. 26(8):943-50, each incorporated by reference in their entireties.

Techniques for conjugating therapeutic moieties to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al, (eds.), pp. 623-53 (Marcel Dekker, Inc. 1987); Thorpe, "Antibody Carriers Of Cytotoxic Agents In Cancer Therapy: A Review", in Monoclonal Antibodies 84: Biological And Clinical Applications, Pinchera et al. (eds.), pp, 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., 1982, Immunol. Rev. 62:119-58.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Methods of Producing Antibodies of the Invention

Nucleic Acids Encoding the Antibodies

The invention provides substantially purified nucleic acid molecules which encode polypeptides comprising segments or domains of the LOX-1-binding antibody chains described above. Some of the nucleic acids of the invention comprise the nucleotide sequence encoding the heavy chain variable region shown in SEQ ID NO: 15, 35, 55, 75, or 95, and/or the nucleotide sequence encoding the light chain variable region shown in SEQ ID NO: 25, 45, 65, 85, or 105. In a specific embodiment, the nucleic acid molecules are those identified in Table 1. Some other nucleic acid molecules of the invention comprise nucleotide sequences that are substantially identical (e.g., at least 65, 80%, 95%, or 99%) to the nucleotide sequences of those identified in Table 1. When expressed from appropriate expression vectors, polypeptides encoded by these polynucleotides are capable of exhibiting LOX-1 antigen binding capacity.

Also provided in the invention are polynucleotides which encode at least one CDR region and usually all three CDR regions from the heavy or light chain of the LOX-1-binding antibody set forth above. Some other polynucleotides encode all or substantially all of the variable region sequence of the heavy chain and/or the light chain of the LOX-1-binding antibody set forth above. Because of the degeneracy of the code, a variety of nucleic acid sequences will encode each of the immunoglobulin amino acid sequences.

The nucleic acid molecules of the invention can encode both a variable region and a constant region of the antibody. Some of nucleic acid sequences of the invention comprise nucleotides encoding a heavy chain sequence that is substantially identical (e.g., at least 80%, 90%, or 99%) to the heavy chain sequence set forth in SEQ ID NO: 16, 36, 56, 76, or 96. Some other nucleic acid sequences comprising nucleotide encoding a light chain sequence that is substantially identical (e.g., at least 80%, 90%, or 99%) to the light chain sequence set forth in SEQ ID NO: 26, 46, 66, 86, or 106.

The polynucleotide sequences can be produced by de novo solid-phase DNA synthesis or by PCR mutagenesis of an existing sequence (e.g., sequences as described in the Examples below) encoding a LOX-1-binding antibody or its binding fragment. Direct chemical synthesis of nucleic acids can be accomplished by methods known in the art, such as the phosphotriester method of Narang et al., 1979, Meth. Enzymol. 68:90; the phosphodiester method of Brown et al., Meth. Enzymol. 68:109, 1979; the diethylphosphoramidite method of Beaucage et al., Tetra. Lett., 22:1859, 1981; and the solid support method of U.S. Pat. No. 4,458,066. Introducing mutations to a polynucleotide sequence by PCR can be performed as described in, e.g., PCR Technology: Principles and Applications for DNA Amplification, H. A. Erlich (Ed.), Freeman Press, NY, N.Y., 1992; PCR Protocols: A Guide to Methods and Applications, Innis et al. (Ed.), Academic Press, San Diego, Calif., 1990; Mattila et al., Nucleic Acids Res. 19:967, 1991; and Eckert et al., PCR Methods and Applications 1:17, 1991.

Also provided in the invention are expression vectors and host cells for producing the LOX-1-binding antibodies described above. Various expression vectors can be employed to express the polynucleotides encoding the LOX-1-binding antibody chains or binding fragments. Both viral-based and nonviral expression vectors can be used to produce the antibodies in a mammalian host cell. Nonviral vectors and systems include plasmids, episomal vectors, typically with an expression cassette for expressing a protein or RNA, and human artificial chromosomes (see, e.g., Harrington et al., Nat Genet 15:345, 1997). For example, nonviral vectors useful for expression of the LOX-1-binding polynucleotides and polypeptides in mammalian (e.g., human) cells include pThioHis A, B & C, pcDNA3.1/His, pEBVHis A, B & C, (Invitrogen, San Diego, Calif.), MPSV vectors, and numerous other vectors known in the art for expressing other proteins. Useful viral vectors include vectors based on retroviruses, adenoviruses, adenoassociated viruses, herpes viruses, vectors based on SV40, papilloma virus, HBP Epstein Barr virus, vaccinia virus vectors and Semliki Forest virus (SFV). See, Brent et al., supra; Smith, Annu. Rev. Microbiol. 49:807, 1995; and Rosenfeld et al., Cell 68:143, 1992.

The choice of expression vector depends on the intended host cells in which the vector is to be expressed. Typically, the expression vectors contain a promoter and other regulatory sequences (e.g., enhancers) that are operably linked to the polynucleotides encoding a LOX-1-binding antibody chain or fragment. In some embodiments, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under noninducing conditions without biasing the population for coding sequences whose expression products are better tolerated by the host cells. In addition to promoters, other regulatory elements may also be required or desired for efficient expression of a LOX-1-binding antibody chain or fragment. These elements typically include an ATG initiation codon and adjacent ribosome binding site or other sequences. In addition, the efficiency of expression may be enhanced by the inclusion of enhancers appropriate to the cell system in use (see, e.g., Scharf et al., Results Probl. Cell Differ. 20:125, 1994; and Bittner et al., Meth. Enzymol., 153:516, 1987). For example, the SV40 enhancer or CMV enhancer may be used to increase expression in mammalian host cells.

The expression vectors may also provide a secretion signal sequence position to form a fusion protein with polypeptides encoded by inserted LOX-1-binding antibody sequences. More often, the inserted LOX-1-binding antibody sequences are linked to a signal sequences before inclusion in the vector. Vectors to be used to receive sequences encoding LOX-1-binding antibody light and heavy chain variable domains sometimes also encode constant regions or parts thereof. Such vectors allow expression of the variable regions as fusion proteins with the constant regions thereby leading to production of intact antibodies or fragments thereof. Typically, such constant regions are human.

The host cells for harboring and expressing the LOX-1-binding antibody chains can be either prokaryotic or eukaryotic. *E. coli* is one prokaryotic host useful for cloning and expressing the polynucleotides of the present invention. Other microbial hosts suitable for use include bacilli, such as *Bacillus subtilis*, and other enterobacteriaceae, such as *Salmonella, Serratia*, and various *Pseudomonas* species. In these prokaryotic hosts, one can also make expression vectors, which typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation. Other microbes, such as yeast, can also be employed to express LOX-1-binding polypeptides of the invention. Insect cells in combination with baculovirus vectors can also be used.

In some preferred embodiments, mammalian host cells are used to express and produce the LOX-1-binding polypeptides of the present invention. For example, they can be either a hybridoma cell line expressing endogenous immunoglobulin genes (e.g., the 106.09 myeloma hybridoma clone as described in the Examples) or a mammalian cell line harboring an exogenous expression vector (e.g., the SP2/0 myeloma cells exemplified below). These include any normal mortal or normal or abnormal immortal animal or human cell. For example, a number of suitable host cell lines capable of secreting intact immunoglobulins have been developed including the CHO cell lines, various Cos cell lines, HeLa cells, myeloma cell lines, transformed B-cells and hybridomas. The use of mammalian tissue cell culture to express polypeptides is discussed generally in, e.g., Winnacker, FROM GENES TO CLONES, VCH Publishers, N.Y., N.Y., 1987. Expression vectors for mammalian host cells can include expression control sequences, such as an origin of replication, a promoter, and an enhancer (see, e.g., Queen, et al., Immunol. Rev. 89:49-68, 1986), and necessary processing information sites, such as ribosome binding sites, RNA splice sites, polyadenylation sites, and transcriptional terminator sequences. These expression vectors usually contain promoters derived from mammalian genes or from mammalian viruses. Suitable promoters may be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MRP polIII promoter, the constitutive MPSV promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts. (See generally Sambrook, et al., supra). Other methods include, e.g., electroporation, calcium phosphate treatment, liposome-mediated transformation, injection and microinjection, ballistic methods, virosomes, imrnunoliposomes, polycation:nucleic acid conjugates, naked DNA, artificial virions, fusion to the herpes virus structural protein VP22 (Elliot and O'Hare, Cell 88:223, 1997), agent-enhanced uptake of DNA, and ex vivo transduction. For long-term, high-yield production of recombinant proteins, stable expression will often be desired. For example, cell lines which stably express LOX-1-binding antibody chains or binding fragments can be prepared using expression vectors of the invention which contain viral origins of replication or endogenous expression elements and a selectable marker gene. Following the introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type.

Generation of Monoclonal Antibodies of the Invention

Monoclonal antibodies (mAbs) can be produced by a variety of techniques, including conventional monoclonal antibody methodology e.g., the standard somatic cell hybridization technique of Kohler and Milstein, 1975 Nature 256: 495. Many techniques for producing monoclonal antibody can be employed e.g., viral or oncogenic transformation of B lymphocytes.

Animal systems for preparing hybridomas include the murine, rat and rabbit systems. Hybridoma production in the mouse is a well established procedure. Immunization protocols and techniques for isolation of immunized splenocytes for fusion are known in the art. Fusion partners (e.g., murine myeloma cells) and fusion procedures are also known.

Chimeric or humanized antibodies of the present invention can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art. See e.g., U.S. Pat. No. 5,225,539 to Winter, and U.S. Pat. Nos. 5,530,101; 5,585,089; 5,693,762 and 6,180,370 to Queen et al.

In a certain embodiment, the antibodies of the invention are human monoclonal antibodies. Such human monoclonal antibodies directed against LOX-1 can be generated using transgenic or transchromosomic mice carrying parts of the human immune system rather than the mouse system. These transgenic and transchromosomic mice include mice referred to herein as HuMAb mice and KM mice, respectively, and are collectively referred to herein as "human Ig mice."

The HuMAb Mouse® (Medarex, Inc.) contains human immunoglobulin gene miniloci that encode un-rearranged human heavy (μ and γ) and κ light chain immunoglobulin sequences, together with targeted mutations that inactivate the endogenous μ and κ chain loci (see e.g., Lonberg, et al., 1994 Nature 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal (Lonberg, N. et al., 1994 supra; reviewed in Lonberg, N., 1994 Handbook of Experimental Pharmacology 113:49-101; Lonberg, N. and Huszar, D., 1995 Intern. Rev. Immunol. 13: 65-93, and Harding, F. and Lonberg, N., 1995 Ann. N. Y. Acad. Sci. 764:536-546). The preparation and use of HuMAb mice, and the genomic modifications carried by such mice, is further described in Taylor, L. et al., 1992 Nucleic Acids Research 20:6287-6295; Chen, J. et al., 1993 International Immunology 5: 647-656; Tuaillon et al., 1993 Proc. Natl. Acad. Sci. USA 94:3720-3724; Choi et al., 1993 Nature Genetics 4:117-123; Chen, J. et al., 1993 EMBO J. 12: 821-830; Tuaillon et al., 1994 J. Immunol. 152:2912-2920; Taylor, L. et al., 1994 International Immunology 579-591; and Fishwild, D. et al., 1996 Nature Biotechnology 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92103918, WO 93/12227, WO 94/25585, WO 97113852, WO 98/24884 and WO 99/45962, all to Lonberg and Kay; and PCT Publication No. WO 01/14424 to Korman et al.

In another embodiment, human antibodies of the invention can be raised using a mouse that carries human immunoglobulin sequences on transgenes and transchomosomes such as a mouse that carries a human heavy chain transgene and a human light chain transchromosome. Such mice, referred to herein as "KM mice", are described in detail in PCT Publication WO 02/43478 to Ishida et al.

Still further, alternative transgenic animal systems expressing human immunoglobulin genes are available in the art and can be used to raise LOX-1-binding antibodies of the invention. For example, an alternative transgenic system referred to as the Xenomouse (Abgenix, Inc.) can be used. Such mice are described in, e.g., U.S. Pat. Nos. 5,939,598; 6,075,181; 6,114,598; 6,150,584 and 6,162,963 to Kucherlapati et al.

Moreover, alternative transchromosomic animal systems expressing human immunoglobulin genes are available in the art and can be used to raise LOX-1-binding antibodies of the invention. For example, mice carrying both a human heavy chain transchromosome and a human light chain tranchromosome, referred to as "TC mice" can be used; such mice are described in Tomizuka et al., 2000 Proc. Natl. Acad. Sci. USA 97:722-727. Furthermore, cows carrying human heavy and light chain transchromosomes have been described in the art (Kuroiwa et al., 2002 Nature Biotechnology 20:889-894) and can be used to raise LOX-1-binding antibodies of the invention.

Human monoclonal antibodies of the invention can also be prepared using phage display methods for screening libraries of human immunoglobulin genes. Such phage display methods for isolating human antibodies are established in the art or described in the examples below. See for example: U.S. Pat. Nos. 5,223,409; 5,403,484; and U.S. Pat. No. 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Framework or Fc Engineering

Engineered antibodies of the invention include those in which modifications have been made to framework residues within VH and/or VL, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis. Such "backmutated" antibodies are also intended to be encompassed by the invention.

Another type of framework modification involves mutating one or more residues within the framework region, or even within one or more CDR regions, to remove T cell-epitopes to thereby reduce the potential immunogenicity of the antibody. This approach is also referred to as "deimmunization" and is described in further detail in U.S. Patent Publication No. 20030153043 by Carr et al.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the CH2-CH3 domain interface region of the Fe-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half-life. Various approaches are possible. For example, one or more of the following mutations can be introduced: T252L, T2545, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fe receptor or the C1 component of complement. This approach is described in further detail in U.S. Pat. Nos. 5,624,821 and 5,648,260, both by Winter et al.

In another embodiment, one or more amino acids selected from amino acid residues can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another embodiment, one or more amino acid residues are altered to thereby alter the ability of the antibody to fix complement. This approach is described further in PCT Publication WO 94/29351 by Bodmer et al.

In yet another embodiment, the Fc region is modified to increase the ability of the antibody to mediate antibody dependent cellular cytotoxicity (ADCC) and/or to increase the affinity of the antibody for an Fcγ receptor by modifying one or more amino acids. This approach is described further in PCT Publication WO 00/42072 by Presta. Moreover, the binding sites on human IgG1 for FcγRI, FcγRII, FcγRIII and FcRn have been mapped and variants with improved binding have been described (see Shields, R. L. et al., 2001 J. Biol. Chen. 276:6591-6604).

In still another embodiment, the glycosylation of an antibody is modified. For example, an aglycoslated antibody can be made (i.e., the antibody lacks glycosylation). Glycosylation can be altered to, for example, increase the affinity of the antibody for "antigen'. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, LecI3 cells, with reduced ability to attach fucose to Asn(297)-linked carbohydrates, also resulting in hypofucosylation of antibodies expressed in that host cell (see also Shields, R. L. et al., 2002 J. Biol. Chem. 277:26733-26740). PCT Publication WO 99/54342 by Umana et al., describes cell lines engineered to express glycoprotein-modifying glycosyl transferases (e.g., beta(1, 4)-N acetylglucosaminyltransferase III (GnTIII)) such that antibodies expressed in the engineered cell lines exhibit increased bisecting GlcNac structures which results in increased ADCC activity of the antibodies (see also Umana et al., 1999 Nat. Biotech. 17:176-180).

Methods of Engineering Altered Antibodies

As discussed above, the LOX-1-binding antibodies having VH and VL sequences or full length heavy and light chain sequences shown herein can be used to create new LOX-1-binding antibodies by modifying full length heavy chain and/or light chain sequences, VH and/or VL sequences, or the constant region(s) attached thereto. Thus, in another aspect of the invention, the structural features of a LOX-1-binding antibody of the invention are used to create structurally related LOX-1-binding antibodies that retain at least one functional property of the antibodies of the invention, such as binding to human LOX-1 and also inhibiting one or more functional properties of LOX-1 (e.g., inhibit LOX-1 binding to the LOX-1 receptor, inhibit LOX-1-dependent cell proliferation).

For example, one or more CDR regions of the antibodies of the present invention, or mutations thereof, can be combined recombinantly with known framework regions and/or other CDRs to create additional, recombinantly-engineered, LOX-1-binding antibodies of the invention, as discussed above. Other types of modifications include those described in the previous section. The starting material for the engineering method is one or more of the VH and/or VL sequences provided herein, or one or more CDR regions thereof. To create the engineered antibody, it is not necessary to actually prepare (i.e., express as a protein) an antibody having one or more of the VH and/or VL sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein.

Accordingly, in another embodiment, the invention provides a method for preparing a LOX-1-binding antibody consisting of a heavy chain variable region antibody sequence having a CDR1 sequence selected from the group consisting of SEQ ID NOs: 8, 28, 48, 68, and 88, a CDR2 sequence selected from the group consisting of SEQ ID NOs: 9, 29, 49, 69, and 89, and/or a CDR3 sequence selected from the group consisting of SEQ ID NOs: 10, 30, 50, 70, and 90; and a light chain variable region antibody sequence having a CDR1 sequence selected from the group consisting of SEQ ID NOs: 18, 38, 58, 78, and 98, a CDR2 sequence selected from the group consisting of SEQ ID NOs: 19, 39, 59, 79, and 99, and/or a CDR3 sequence selected from the group consisting of SEQ ID NOs: 20, 40, 60, 80, and 100;

altering at least one amino acid residue within the heavy chain variable region antibody sequence and/or the light chain variable region antibody sequence to create at least one altered antibody sequence; and expressing the altered antibody sequence as a protein.

Accordingly, in another embodiment, the invention provides a method for preparing a LOX-1-binding antibody consisting of a heavy chain variable region antibody sequence having a CDR1 sequence selected from the group consisting of SEQ ID NOs: 11, 31, 51, 71, and 91, a CDR2 sequence selected from the group consisting of SEQ ID NOs: 12, 32, 52, 72, and 92, and/or a CDR3 sequence selected from the group consisting of SEQ ID NOs: 13, 33, 53, 73, and 93; and a light chain variable region antibody sequence having a CDR1 sequence selected from the group consisting of SEQ ID NOs: 21, 41, 61, 81, and 101, a CDR2 sequence selected from the group consisting of SEQ ID NOs: 22, 42, 62, 82, and 102, and/or a CDR3 sequence selected from the group consisting of SEQ ID NOs: 23, 43, 63, 83, and 103; altering at least one amino acid residue within the heavy chain variable region antibody sequence and/or the light chain variable region antibody sequence to create at least one altered antibody sequence; and expressing the altered antibody sequence as a protein.

Accordingly, in another embodiment, the invention provides a method for preparing a LOX-1-binding antibody optimized for expression in a mammalian cell consisting of: a full length heavy chain antibody sequence having a sequence selected from the group of SEQ ID NOs: 16, 36, 56, 76, or 96; and a full length light chain antibody sequence having a sequence selected from the group of 26, 46, 66, 86, or 106; altering at least one amino acid residue within the full length heavy chain antibody sequence and/or the full length light chain antibody sequence to create at least one altered antibody sequence; and expressing the altered antibody sequence as a protein. In one embodiment, the alteration of the heavy or light chain is in the framework region of the heavy or light chain.

The altered antibody sequence can also be prepared by screening antibody libraries having fixed CDR3 sequences or minimal essential binding determinants as described in US2005/0255552 and diversity on CDR1 and CDR2 sequences. The screening can be performed according to any screening technology appropriate for screening antibodies from antibody libraries, such as phage display technology.

Standard molecular biology techniques can be used to prepare and express the altered antibody sequence. The antibody encoded by the altered antibody sequence(s) is one that retains one, same or all of the functional properties of the LOX-1-binding antibodies described herein, which functional properties include, but are not limited to, specifically binding to human, cynomolgus, rat, and/or mouse LOX-1; and the antibody inhibit LOX-1-dependent cell proliferation in a F36E and/or Ba/F3-LOX-1R cell proliferation assay.

In certain embodiments of the methods of engineering antibodies of the invention, mutations can be introduced randomly or selectively along all or part of an LOX-1-binding antibody coding sequence and the resulting modified LOX-1-binding antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

In certain embodiments of the invention antibodies have been engineered to remove sites of deamidation. Deamidation is known to cause structural and functional changes in a peptide or protein. Deamindation can result in decreased bioactivity, as well as alterations in pharmacokinetics and antigenicity of the protein pharmaceutical. (*Anal Chem.* 2005 Mar. 1; 77(5):1432-9).

In certain embodiments of the invention the antibodies have been engineered to increase pI and inprove their drug-like properties. The pI of a protein is a key determinant of the overall biophysical properties of a molecule. Antibodies that have low pIs have been known to be less soluble, less stable, and prone to aggregation. Further, the purification of antibodies with low pI is challenging and can be problematic especially during scale-up for clinical use. Increasing the pI of the anti-LOX-1 antibodies, or Fabs, of the invention improved their solubility, enabling the antibodies to be formulated at higher concentrations (>100 mg/ml). Formulation of the antibodies at high concentrations (e.g. >100 mg/ml) offers the advantage of being able to administer higher doses of the antibodies into eyes of patients via intravitreal injections, which in turn may enable reduced dosing frequency, a significant advantage for treatment of chronic diseases including cardiovascular disorders. Higher pIs may also increase the FcRn-mediated recycling of the IgG version of the antibody thus enabling the drug to persist in the body for a longer duration, requiring fewer injections. Finally, the overall stability of the antibodies is significantly improved due to the higher pI resulting in longer shelf-life and bioactivity in vivo. Preferably, the pI is greater than or equal to 8.2.

The functional properties of the altered antibodies can be assessed using standard assays available in the art and/or described herein, such as those set forth in the Examples (e.g., ELISAs).

Prophylactic and Therapeutic Uses

Antibodies that binds LOX-1 as described herein, can be used at a therapeutically useful concentration for the treatment of a disease or disorder associated with increased LOX-1 levels and/or activity by administering to a subject in need thereof an effective amount of the antibodies or antigen binding fragments of the invention. The present invention provides a method of treating LOX-1-associated cardiovascular disorders by administering to a subject in need thereof an effective amount of the antibodies of the invention. The present invention provides a method of treating LOX-1-associated cardiovascular disorders by administering to a subject in need thereof an effective amount of the antibodies of the invention.

The antibodies of the invention can be used, inter alia, to prevent treat, prevent, and improve LOX-1 associated conditions or disorders, including but not limited to cardiovascular disorders, endothelial cell dysfunction, endothelial cell disorders, atherosclerosis, arteriosclerosis, hypertension, hyperlipidemia, hypercholesterolemia, diabetes mellitus, nitric oxide deficiency, myocardial infarction, vascular oxidative stress, myocardial ischemia, ischemia-reperfusion, sepsis, diabetic nephropathy, renal disease, cardiomyopathy, heart failure, peripheral artery disease, coronary heart disease, claudication (e.g., intermittent claudication, Rutherford Class II/III Claudication), peripheral artery disease (PAD), angina (e.g., refractory angina), coronary artery disease (CAD)(e.g., due to atherosclerosis of the arteries feeding the heart), stroke, and abnormal endothelium-dependent vasodilation.

Treatment and/or prevention of cardiovascular disorders, e.g., LOX-1-associated cardiovascular disorders, can be determined by a health care professional using clinically relevant measurements of vascular function. Treatment of LOX-1-associated cardiovascular disorders means any action (e.g., administration of an anti-LOX-1 antibody described herein) that results in, or is contemplated to result in, the improvement or preservation of vascular function, vascular anatomy and/or hemodynamic parameters. In addition, prevention as it relates to conditions or disorders associated with cardiovascular disorders means any action (e.g., administration of an anti-LOX-1 antibody described herein) that prevents or slows a worsening in vascular function, and/or a cardiovascular disorders parameter, as defined herein, in a patient at risk for said worsening.

As oxLDLs and soluble LOX-1 levels are both increased in stable angina and acute ischemic syndromes, the anti-LOX-1 antibodies of the invention are expected to inhibit vascular oxidative stress, reduce myocardial ischemia and improve angina and exercise tolerance; said antibodies have the potential to become the first disease-modifying anti-anginal treatment available.

The efficacy of said therapeutic administration may be measured by a serial assessment of frequency and duration of transient ischemic events (ambulatory ECG monitoring) and angina (Seattle angina questionnaire), and serial exercise tolerance testing with perfusion imaging option. Efficacy may also be measured by use of biomarkers such as plasma oxLDL, soluble LOX-1, and oxidative stress biomarkers (F2-isoprostanes, malondialdehyde, myeloperoxidase).

“Claudication,” as used herein, includes severe claudication and other like terms, and describes a mobility impairment and high unmet medical need. Claudication is a condition characterized by lower extremity ischemia, causing muscle fatigue, pain on exertion relieved by rest, limited mobility, and reduced quality of life, and is caused by atherosclerosis and abnormal (e.g., impaired) endothelium-dependent vasodilation. Its prevalence in the US is 8-12 million patients. Among patients with intermittent claudication, 7% will undergo lower extremity bypass surgery, 4% will require major amputations, and 16% will develop worsening claudication. Cardiovascular events, such as myocardial infarction and stroke, occur in 20% of severe claudication sufferers over 5 years. The current therapy is surgical, and treatment through less invasive means, such as the administration of the anti-LOX-1 antibodies of the invention, would represent an enormous therapeutic breakthrough.

The efficacy of said therapeutic administration may be measured by a serial assessment of exercise-induced claudication (plantar flexion and treadmill), with endpoints to include time to onset of pain, exercise duration, and walking distance. Efficacy may also be measured by use of mechanistic biomarkers such as plasma oxLDL and soluble LOX-1; oxidative stress biomarkers (F2-isoprostanes, malondialdehyde, myeloperoxidase); exercise-induced changes in lower extremity flow and muscle O2 saturation.

Another high unmet medical need for which the anti-LOX-1 antibodies of the invention would be therapeutically useful is refractory angina. Angina recurs in affiliated subjects despite optimum medical therapy (e.g., administration of long acting beta-blocker, nitrate, and calcium channel blocker), with no option for revascularization. Refractory angina is a condition marked by chest pain due to ischemia of the heart muscle, generally due to obstruction or spasm of the coronary arteries (e.g., from coronary artery disease), with debilitating symptoms, very limited physical activity and poor quality of life. The 1-1.8 million patients refractory angina sufferers in the US experience increased cardiovascular mortality at a rate of 10% per year; at least 100,000 new refractory angina cases arise per year.

The antibodies of the invention can also be used in combination with other agents for the prevention, treatment; or improvement of LOX-1 associated disorders. For example, statin therapies may be used in combination with the LOX-1 antibodies and antigen binding fragments of the invention for the treatment of patients with cardiovascular disorders.

Pharmaceutical Compositions

The invention provides pharmaceutical compositions comprising the LOX-1-binding antibodies (intact or binding fragments) formulated together with a pharmaceutically acceptable carrier. The compositions can additionally contain one or more other therapeutic agents that are suitable for treating or preventing, for example, cardiovascular disorders. Pharmaceutically acceptable carriers enhance or stabilize the composition, or can be used to facilitate preparation of the composition. Pharmaceutically acceptable carriers include solvents, dispersion media, coatings, antibacterial and antifungal agents, isotonic and absorption delaying agents, and the like that are physiologically compatible.

A pharmaceutical composition of the present invention can be administered by a variety of methods known in the art. The route and/or mode of administration vary depending upon the desired results. It is preferred that administration be intravitreal, intravenous, intramuscular, intraperitoneal, or subcutaneous, or administered proximal to the site of the target. The pharmaceutically acceptable carrier should be suitable for intravitreal, intravenous, intramuscular, subcutaneous, parenteral, spinal or epidermal administration (e.g., by injection or infusion). Depending on the route of administration, the active compound, i.e., antibody, bispecific and multispecific molecule, may be coated in a material to protect the compound from the action of acids and other natural conditions that may inactivate the compound.

The composition should be sterile and fluid. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

Pharmaceutical compositions of the invention can be prepared in accordance with methods well known and routinely practiced in the art. See, e.g., Remington: The Science and Practice of Pharmacy, Mack Publishing Co., 20th ed., 2000; and Sustained and Controlled Release Drug Delivery Systems, J. R. Robinson, ed., Marcel Dekker, Inc., New York, 1978. Pharmaceutical compositions are preferably manufactured under GMP conditions. Typically, a therapeutically effective dose or efficacious dose of the LOX-1-binding antibody is employed in the pharmaceutical compositions of the invention. The LOX-1-binding antibodies are formulated into pharmaceutically acceptable dosage forms by conventional methods known to those of skill in the art. Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Actual dosage levels of the active ingredients in the pharmaceutical compositions of the present invention can be varied so as to obtain an amount of the active ingredient which is effective to achieve the desired therapeutic response for a particular patient, composition, and mode of administration, without being toxic to the patient. The selected dosage level depends upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors.

A physician or veterinarian can start doses of the antibodies of the invention employed in the pharmaceutical composition at levels lower than that required to achieve the desired therapeutic effect and gradually increase the dosage until the desired effect is achieved. In general, effective doses of the compositions of the present invention, for the treatment of a cardiovascular disorders described herein vary depending upon many different factors, including means of administration, target site, physiological state of the patient, whether the patient is human or an animal, other medications administered, and whether treatment is prophylactic or therapeutic. Treatment dosages need to be titrated to optimize safety and efficacy. For systemic administration with an antibody, the dosage ranges from about 0.0001 to 100 mg/kg, and more usually 0.01 to 15 mg/kg, of the host body weight. For intravitreal administration with an antibody, the dosage may range from 0.1 mg/eye to 5 mg/eye. For example, 0.1 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, 1.0 mg/ml, 1.1 mg/ml, 1.2 mg/ml, 1.3 mg/ml, 1.4 mg/ml, 1.5 mg/ml, 1.6 mg/nil, 1.7 mg/ml, 1.8 mg/ml, 1.9 mg/ml, 2.0 mg/ml, 2.1 mg/ml, 2.2 mg/ml, 2.3 mg/ml, 2.4 mg/ml, 2.5 mg/ml, 2.6 mg/ml, 2.7 mg/ml, 2.8 mg/ml, 2.9 mg/ml, 3.0 mg/ml, 3.1 mg/ml, 3.2 mg/ml, 3.3 mg/ml, 3.4 mg/ml, 3.5 mg/ml, 3.6 mg/ml, 3.7 mg/ml, 3.8 mg/ml, 3.9 mg/ml, 4.0 mg/ml, 4.1 mg/ml, 4.2 mg/ml, 4.3 mg/ml, 4.4 mg/ml, 4.5 mg/ml, 4.6 mg/ml, 4.7 mg/ml, 4.8 mg/ml, 4.9 mg/ml, or 5.0 mg/ml. An exemplary treatment regime entails systemic administration once per every two weeks or once a month or once every 3 to 6 months. An exemplary treatment regime entails systemic administration once per every two weeks or once a month or once every 3 to 6 months, or as needed (PRN).

Antibody is usually administered on multiple occasions. Intervals between single dosages can be weekly, monthly or yearly. Intervals can also be irregular as indicated by measuring blood levels of LOX-1-binding antibody in the patient. In addition alternative dosing intervals can be determined by a physician and administered monthly or as necessary to be efficacious. In some methods of systemic administration, dosage is adjusted to achieve a plasma antibody concentration of 1-1000 μg/ml and in some methods 25-500 μg/ml. Alternatively, antibody can be administered as a sustained release formulation, in which case less frequent administration is required. Dosage and frequency vary depending on the half-life of the antibody in the patient. In general, humanized antibodies show longer half life than that of chimeric antibodies and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

EXAMPLES

The following examples are provided to further illustrate the invention but not to limit its scope. Other variants of the invention will be readily apparent to one of ordinary skill in the art and are encompassed by the appended claims.

Example 1: Preparation of Purified Recombinant Human Soluble LOX-1 for Use as an Antigen A nucleic acid sequence encoding the extracellular domain (amino acid residues 61-273) of human LOX-1 polypeptide with N-terminal signal peptide from human CD33, purification tag (EFHR), and BirA biotinylation sequence (GLNDIFEAQKIEWHE) (SEQ ID NO 144) was subcloned into the mammalian cell expression vector pRS5a. The resulting plasmid, pRS5a_APP-Avi-human-sLOX-1(61-273), was transiently transfected into HEK293T cells using standard polyethylenimine (PEI) transfection methods. Cells were propagated in suspension culture in Novartis medium M11V3 (Bioconcept) and transfection was carried out at $1.4\times10^6$ cells/nil final cell concentration in 5 liters media using a Wave Bioreactor.

Five hours after transfection, 5 liters of ExCell VPRO serum-free media (Sigma) was added. Cells were grown at 37° C. and 5% $CO_2$ for 10 days. Cells were then harvested by centrifugation, followed by filtration with a 0.22 micron sterile filter. The clarified supernatant was passed over a 20 mL anti-APP affinity resin (Novartis proprietary) equilibrated with PBS. The column was washed with PBS until baseline absorbance at 280 nm was reached. The column was then washed with 10 column volumes of PBS containing 1% Triton X-100 and 0.3% tri-n-butylphosphate, followed by 25 column volumes PBS. The sLOX-1 protein was then eluted with 50 mM sodium citrate, pH 3.0, and the fractions were neutralized with $1/10^{th}$ volume of 1M Tris, pH 9.0. Relevant fractions were pooled and exhaustively dialyzed against PBS, then aliquoted and flash frozen in liquid nitrogen. Analytical sizing analysis showed the purified soluble LOX-1 protein material to be >95% dimer form, which is the expected form of this protein.

Example 2: Preparation of Human LOX-1 Transfected HEK293 Cells

To test the binding specificity and functional activity of anti-LOX1 specific antibodies, HEK293 cells stably over-expressing human LOX-1 were generated. Using standard Lipofectamine 2000 transfection methods, HEK293-6E cells were transfected with a mammalian expression plasmid encoding full-length human LOX-1 cDNA and hygromycin resistance. Transfected cultures were evaluated for surface expression of LOX-1 by flow cytometry on day three post transfection and then subjected to hygromycin selection (200 μg/ml) to enrich for stably expressing cells. Clonal populations were obtained by two sequential rounds of limiting dilution and expression was confirmed by flow cytometry. Only clones maintaining stable LOX-1 expression for more than four weeks in culture were selected and used in subsequent antibody characterization assays.

Example 3: Preparation of Monoclonal Antibodies

Recombinant human LOX-1 protein was prepared in-house as described in Example 1, and was used as immunogen for the generation of anti-LOX-1 hybridoma clones. The LOX-1 antigen in PBS was mixed with an equal volume of Freund's adjuvant to enhance the immune response in Balb/c mice. A complete Freund's adjuvant (Sigma F5881) was used for the first injection and an incomplete Freund's adjuvant (Sigma F5506) for the subsequent immunizations.

Animal immunizations and sample collection were carried out according to the IACUC-approved standard animal use protocols. Briefly, female Balb/c VAF mice at the age of 5-6 weeks (Charles River Laboratories) were immunized with the antigen emulsion of human LOX-1 protein and adjuvant. The mice were subcutaneously immunized for 4 times with approximately 20 μg protein in 100 μL of the antigen-adjuvant mixture per animal. The injections were performed every 2-3 weeks to develop immune responses in the animals. Three days before cell fusion for the hybridoma generation, the mice were intraperitoneally boosted one more time with the same dose of LOX-1 antigen mixed with incomplete Freund's adjuvant, and were sacrificed for the spleen collection under sterilized surgical conditions on the day of cell fusion.

Spleens from the immunized mice were ground between two sterile and frosted microscopic slides to prepare for single cell suspension in RPMI-1640 medium. The spleen cells were pelleted and washed twice with RPMI-1640 medium. For cell fusions to generate hybridoma clones, the splenocytes were mixed and fused with murine myeloma P3X63Ag8.653 cells (Kearney J. F. et al., 1979. J. Immunol., 123:1548-1550 using polyethylene glycol-1500 as fusogen according to standard fusion protocols (Zhang C. 2012. Methods Mol. Biol. 901:117-135). Following cell fusions and centrifugation, the cells were suspended in complete RPMI-1640 medium (200 mL/spleen) containing hypoxanthine-aminopterin-thymidine (HAT) supplement (Sigma H-0262), and were plated into 96-well flat-bottom plates (Corning-Costar 3596) at 200 μL of cell suspension per well.

Following incubation at 37° C., 5% CO2 for 3-4 days, 100 μL of culture supernatant were removed from each well of the plates and replaced with an equal volume of complete RPMI-1640 medium containing hypoxanthine-thymidine (HT) supplement (Sigma H-0137). The plates continued to be incubated in an atmosphere of 5% CO2 at 37° C. until hybridoma clones had grown large enough colonies to enable antibody screening.

Example 4: Hybridoma Screening, Subcloning and Selection

On week 2 post-fusion, when hybridoma cells had grown to be half-confluent in the plate wells and the supernatant had changed to an orange color, hybridoma supernatants were sampled from the plates for antibody screening by immunoassays, such as immunofluorescence flow cytometry for cell-based LOX-1 antigens or ELISA for LOX-1 protein antigen. For primary screening, hybridoma supernatants were tested by flow cytometry using LOX-1-transfected 293-6E cells versus non-transfected cells. Briefly, human LOX-1-transfected 293-6E cells, or the non-transfected cells, were respectively incubated with 50 μL of hybridoma supernatant, followed by labeling with fluorescein-AffiniPure Fab fragment goat anti-mouse IgG (H+L) conjugate (Jackson ImmunoResearch Laboratories), and analyzed by flow cytometry with Becton Dickinson FACSCalibur in an automatic mode.

By flow cytometric analysis, hybridoma clones that reacted with LOX-1-transfected 293-6E cells but not with non-transfected cells were identified and selected from fusion plates. The desired hybridoma clones were expanded in T12 plates for further characterization. Hybridoma clone of interest was subcloned by limiting dilution and microscopically picking single colonies to attain a monoclonal population that produces a LOX-1-specific monoclonal antibody. The selected hybridoma subclones were expanded in T12 plates and frozen for cryopreservation or used for monoclonal antibody production. The isotypes of specific monoclonal antibodies derived from hybridoma clones was determined by using commercially-available isotyping reagents.

On the basis of screening results, a panel of 24 human LOX-1-specific hybridoma clones was identified and selected from the immunization of mice with human LOX-1 antigen. One of these hybridoma clones, Clone 39.1E2E10 (abbreviated as E2E10, and herein referred to as E2E10 or murine parental), produced a monoclonal antibody of IgG1 with a kappa light chain, and was selected as one of the lead candidates for antibody sequencing and humanization based on its LOX-1 binding properties.

Example 5: Screening of Monoclonal Antibodies for Inhibition of OxLDL Binding to LOX-1

LOX-1 antibodies were purified from hybridoma supernatants using standard methods (e.g., Protein A affinity chromatography).

Purified APP-Avi-soluble human soluble LOX-1(61-273) protein prepared as described in Example 1 was biotinylated as follows: purified soluble LOX-1 protein (8-10 mg) in 50 mM Bicine pH 8.3 buffer at a final concentration of approximately 1 mg/mL was incubated in the presence of 10 mM ATP, 10 mM magnesium acetate, 0.1 mM biotin, and BirA biotin ligase (Avidity) at 30° C. for 1 hr and then placed at 4° C. overnight. The protein was then purified using a 5200 Superdex 16/60 column equilibrated with PBS. Relevant fractions were pooled and the protein was concentrated to approximately 1 mg/mL concentration, aliquoted, and flash frozen in liquid nitrogen. Percent biotinylation was assessed by mass spectrometry peptide mapping of unbiotinylated and biotinylated samples. Typically, the biotinylation yield was >95%, and unbiotinylated material was not detected. Analytical sizing analysis showed the biotinylated material to be 100% dimer form, which is the expected form of this protein.

The biotinylated soluble LOX-1 protein was then diluted to 2.5 μg/mL concentration in PBS, and 0.1 mL of this solution was added to wells of a NeutrAvidin 96-well plate (Pierce catalog number 15128), and the plate was then incubated overnight at 4° C. The plate was washed three times with PBS, and then blocked by adding 0.3 mL per well of 25% Block Ace (AbD Serotec catalog number BUF029) and incubating the plate at room temperature for 2 hours with gentle shaking. The plate was then washed once with PBS. Serial dilutions of LOX-1 antibodies diluted in 1% BSA/PBS were prepared, and 0.1 mL of diluted antibodies added to the plate. The plate was incubated for 1 hour at room temperature, then washed three times with PBS. Next, 0.1 mL of oxLDL (high binding OxLDL, Kalen Biomedical catalog number 770212-7) diluted in 1% BSA'PBS to a final concentration of 2 ug/mL.

To generate an oxLDL standard curve, various concentrations of oxLDL were tested in the absence of LOX-1 antibody, using a top concentration of 20 ug/mL oxLDL. The plate was then incubated for 2 hours at room temperature, and the plate then washed three times with PBS. 0.1 mL/well of HRP-conjugated anti-ApoB100 antibody (The Binding Site, Inc., catalog number PP086) diluted 1:1000 in 1% BSA/PBS was then added, and incubated for 2 hours at room temperature. The plate was washed 6 times with PBS. 0.1 mL/well TMB substrate was then added and the plate was incubated for 10 minutes at room temperature. Stop solution (2N sulfuric acid, 50 µL/well) was added to each well, and the optical absorbance at 450 nm measured using an appropriate plate reader.

Example 6: Humanization of Monoclonal Antibodies

Mouse monoclonal antibody E2E10 was Humaneered™ to bring its protein sequence closer to a human germline sequence and decrease its immunogenicity. Humaneering™ technology is available through KaloBios of South San Francisco, Antibody Humaneering™ generates engineered human antibodies with V-region sequences that have high homology to a human germline sequence while still retaining the specificity and affinity of the parent or reference antibody (U.S. Patent Publ. 2005/0255552 and 2006/0134098). The process first identifies the minimum antigen binding specificity determinants (BSDs) in the heavy and light chain variable regions of a reference Fab (typically sequences within the heavy chain CDR3 and the light chain CDR3). As these heavy and light chain BSDs are maintained in all libraries constructed during the Humaneering™ process, each library is epitope-focused, and the final, fully Humaneered™ antibodies retain the epitope specificity of the original mouse antibody.

Next, cassette libraries which a portion of the heavy or light chain variable region of the mouse Fab is replaced with a library of human sequences) are generated. A bacterial secretion system is used to express members of the library as antibody Fab fragments, and the library is screened for Fabs that bind antigen using a colony-lift binding assay (CLBA). Positive clones are further characterized to identify those with the highest affinity. Identified human cassettes supporting binding in the context of residual murine sequences are then combined in a final library screen to generate completely human V-regions.

The resulting Humaneered™ Fabs have V-segment sequences derived from human libraries, retain the short BSD sequences identified within the CDR3 regions, and have human germline Framework 4 regions. These Fabs are converted to full IgGs by cloning the variable regions of the heavy and light chains into IgG expression vectors. Fully Humaneered™ antibodies generated in this process retain the binding specificity of the parent, murine antibody, typically have equivalent or higher affinity for antigen than the parent antibody, and have V-regions with a high degree of sequence identity compared with human germline antibody genes at the protein level.

Heavy and light chain compositions of Humaneered™ LOX-1 antibodies FF1, FF3, FF4, FF5, and FF6, and their percent similarity to the closest human germline sequence are shown in Table 2.

TABLE 2

Heavy and Light Chain Compositions of LOX-1 Antibodies and Percent Similarity to Closest Human Germline Sequence (HC = heavy chain. LC = light chain)

| Fab | HC | HC % Vh1-O2 | LC | LC % Vk1-L5 |
|---|---|---|---|---|
| FF1 | 28 + Tested | 90 | 28Lc | 94 |
| FF3 | 28 + All | 92 | 28Lc | 94 |
| FF4 | 28 + All | 92 | 21Lc | 93 |
| FF5 | 28 + All | 92 | 62lc | 90 |
| FF6 | 28 + All | 92 | 62Lc | 90 |

Example 7: LOX-1 Antibody Inhibition of OxLDL Binding to LOX-1 Protein

Figure 1B:
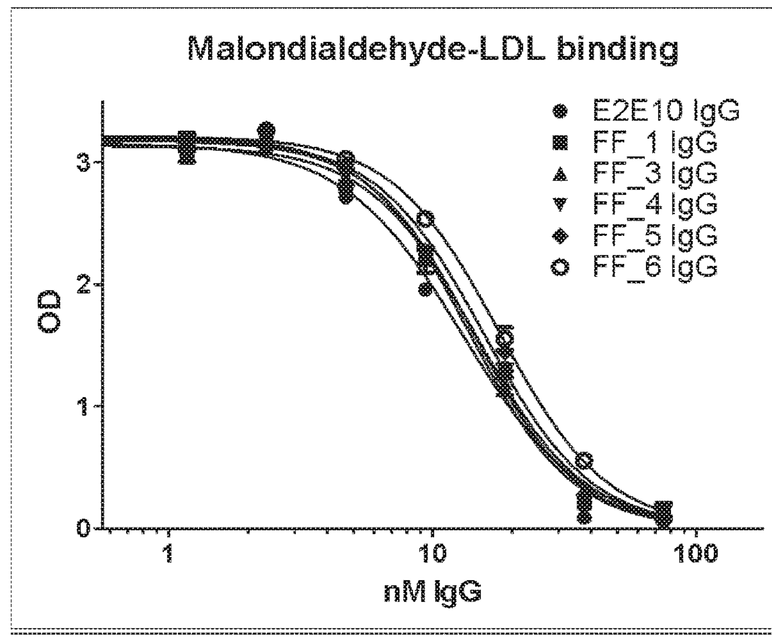
Figure 1C:
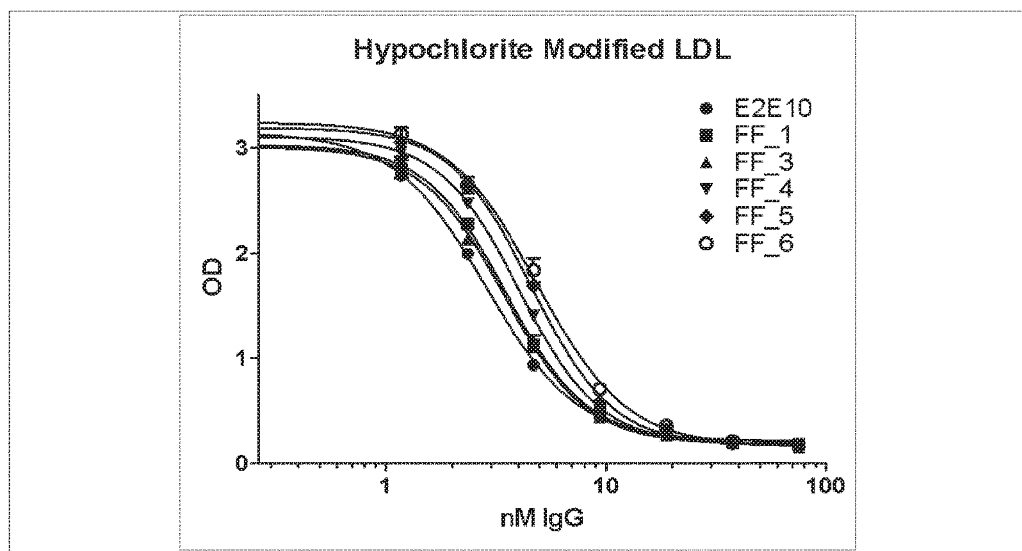

The ability of LOX-1 antibodies to inhibit oxLDL binding to LOX-1 protein was determined using the method described in Example 4. In addition to "high binding OxLDL" from Kalen Biomedical (catalog number 770212-7), which is generated by copper sulfate mediated oxidation of LDL, two other forms of modified LDL were tested in this assay: malondialdehyde modified LDL (Academy Bio-Medical Co. catalog number 20P-MD-L105) and hypochlorite modified LDL. Hypochlorite modified LDL was prepared according to the following procedure. Human LDL (Kalen Biomedical catalog number 770200-4) was diluted with PBS to a final concentration of 0.25 mg/mL. Sodium hypochlorite (NaOCl, JT Baker catalog number 9416-01) was then added to 0.1 mM final concentration. The solution was incubated at room temperate for 4 hours, then quenched by adding L-methionine to a final concentration of reaction by adding 5 µl of 100 mM Mehionine per 200 µl total volume. Representative data showing inhibition of modified LDL binding to LOX-1 by LOX-1 antibodies is shown in FIGS. 1A-1C, and described in Table 3.

TABLE 3

LOX-1 Antibody Inhibition of OxLDL Binding to LOX-1 Protein (table with IC50 values).

| | LLG783 (FF1) | LLG785 (FF3) | LLG786 (FF4) | LLG787 (FF5) | LLG788 (FF6) | E2E10 (murine parental) |
|---|---|---|---|---|---|---|
| Inhibition of huLOX-1 binding to copper-sulfate-oxidized LDL ($IC_{50}$, nM) | 7 | 8 | 8 | 10 | 12 | 6 |

TABLE 3-continued

LOX-1 Antibody Inhibition of OxLDL Binding to LOX-1 Protein (table with IC50 values).

| | LLG783 (FF1) | LLG785 (FF3) | LLG786 (FF4) | LLG787 (FF5) | LLG788 (FF6) | E2E10 (murine parental) |
|---|---|---|---|---|---|---|
| Inhibition of huLOX-1 binding to malon-dialdehyde-modified LDL ($IC_{50}$, nM) | 15 | 14 | 14 | 17 | 18 | 13 |
| Inhibition of huLOX-1 binding to hypochlorite modified LDL ($IC_{50}$, nM) | 4 | 3 | 4 | 5 | 5 | 3 |
| dil-OxLDL binding to LOX-1 on cells (IC50, nM) | 5.5 | 3.3 | 5.0 | 4.1 | 5.9 | 4.0 |
| Binding of biotinylated LOX-1 antibodies to Human Neutrophils ($EC_{50}$, μg/mL) | 0.15 | 0.13 | 0.23 | 0.08 | 0.28 | 0.04 |

Example 8: LOX-1 Antibody Inhibition of OxLDL Binding to LOX-1/HEK293 Cells

The huLOX-1/HEK293 cells were maintained in DMEM containing 10% FBS and 1% Penicillin-Streptomycin as an adherent monolayer in T flasks containing 20 ml culture medium per 75 $cm^2$ surface area. The cells were incubated in a humidified incubator at 5% $CO_2$ and 37° C., and sub-cultivated every 2-3 days. To passage the cells, the culture medium is removed, and the monolayer is washed once with 10-20 ml pre-warmed PBS. After washing, 1 ml of pre-warmed TrypLE Express is added, and the cells were incubated at 37° C. for 5 min. Pre-warmed fresh culture medium was then added.

Figure 2:
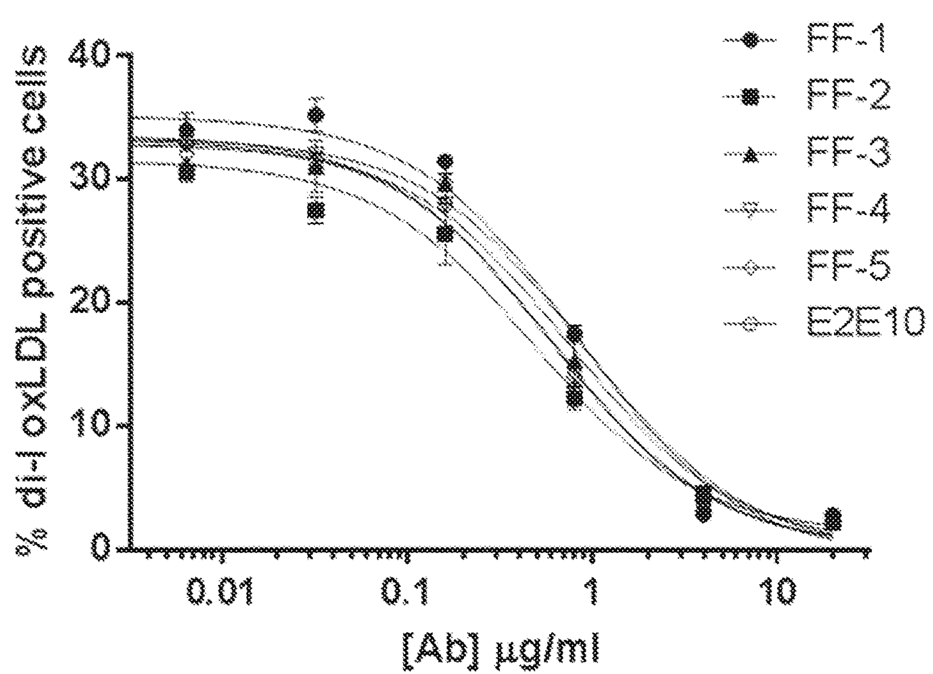
FIG. 2 depicts LOX-1 antibodies inhibiting dil-labeled OxLDL binding to human LOX-1 transfected HEK293 cells.

The huLOX-1/HEK293 cells were resuspended at $1\times10^6$ cells/mL and seeded 50 μL per well into a 96-well V-bottom plate ($5\times10^4$ cells per well). LOX-1 or irrelevant control antibodies in assay medium (DMEM+10% FBS) were then added to the cells. Typical final antibody concentrations ranged from 0.006 μg/mL to 20 μg/mL. The cells were incubated at 37° C. for 1 hour, then washed twice with warm HBSS. Dil-oxLDL (human dil-labeled "High Oxidized" LDL, Kalen Biomedical, catalog number 770262-9; Dil is 1,1'-dioctadecyl-3,3,3',3'-tetramethylindocarbocyanine perchlorate) in 50 ul assay medium was then added to a final concentration 30 to 100 μg/mL. The cells were then incubated at 37° C. for 2 hours, and then washed twice with FACS buffer (2% FBS in PBS). Cells were then analyzed for intensity of Di-I fluorescence by flow cytometry, as depicted in FIG. 2 and Table 3.

Example 9: OxLDL Induced Reactive Oxygen Species (ROS) Production Assay

LOX-1 antibodies or irrelevant control antibodies were incubated at 2× final concentration either alone or in the presence of a $(Fab)_2$ cross-linker (polyclonal goat anti-human IgG Fe $(Fab)_2$, Abeam catalog number ab98526)) in 0.05 mL assay medium (DMEM+10% FBS) and incubated at room temperature for 15 min. The $(Fab)_2$ cross-linker to LOX-1 antibody ratio was varied and included 1:1 and 1:2 ratios. In dose response experiments with LOX-1 or control antibody alone (without cross-linker), antibody concentrations ranging from 0.005 μg/mL to 20 μg/mL were used. In experiments comparing antibody alone to antibody with cross-linker, antibody concentrations ranging from 0.03 μg/mL to 20 μg/mL were used.

Figure 3:
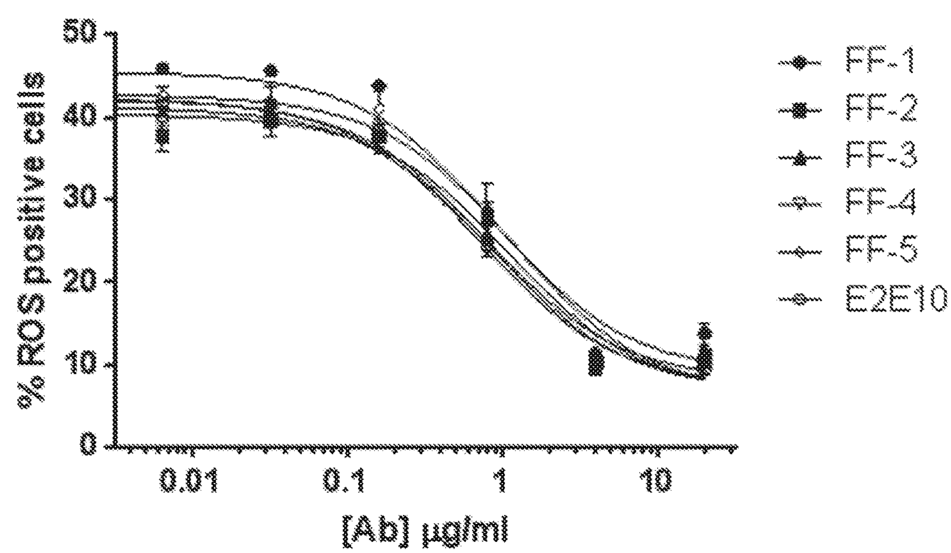
FIG. 3 depicts a dose response curve of LOX-1 antibody inhibition of oxLDL induced reactive oxygen species (ROS) production in human LOX-1 transfected HEK293 cells.
Figure 4A:
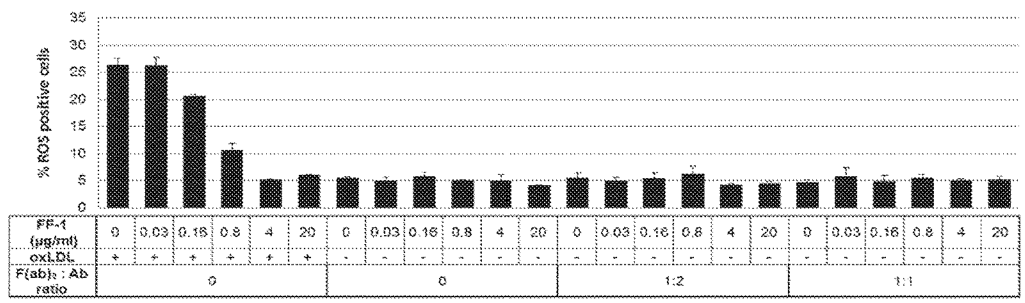
FIGS. 4A-4F demonstrate LOX-1 antibodies (antibodies alone or in the presence of a cross-linking $Fab_2$) inhibiting oxLDL induced reactive oxygen species (ROS) production in human LOX-1 transfected HEK293 cells.
Figure 4B:
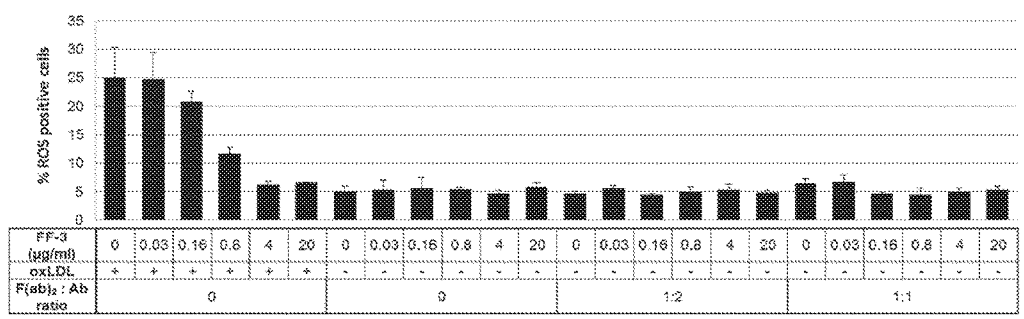
Figure 4C:
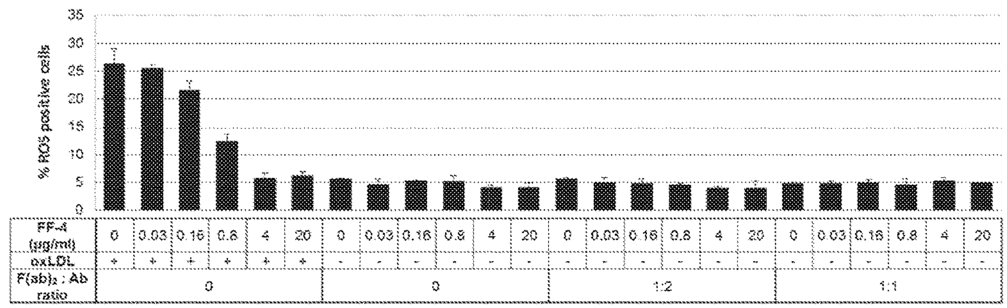
Figure 4D:
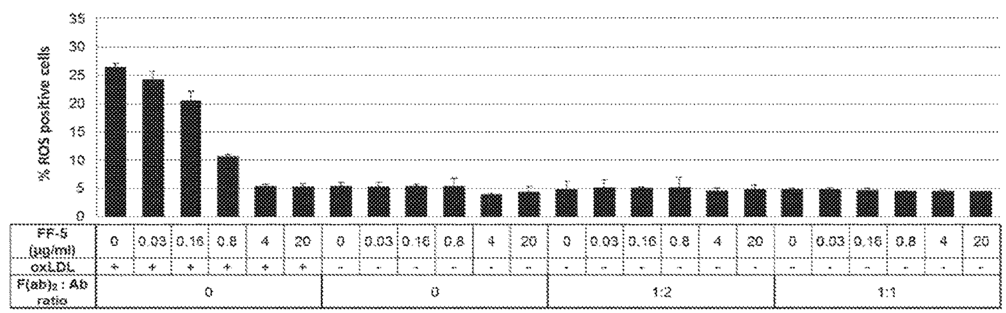
Figure 4E:
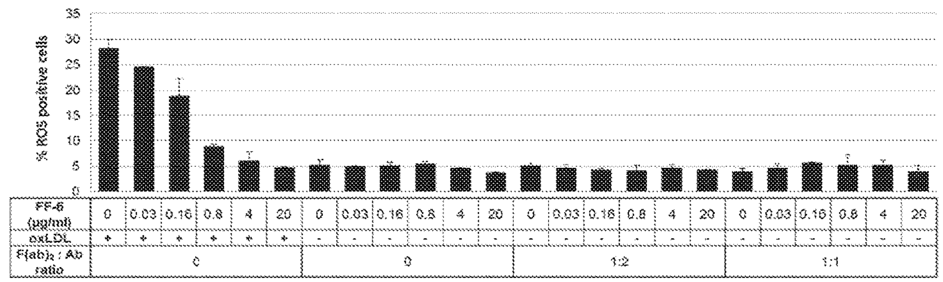
Figure 4F:
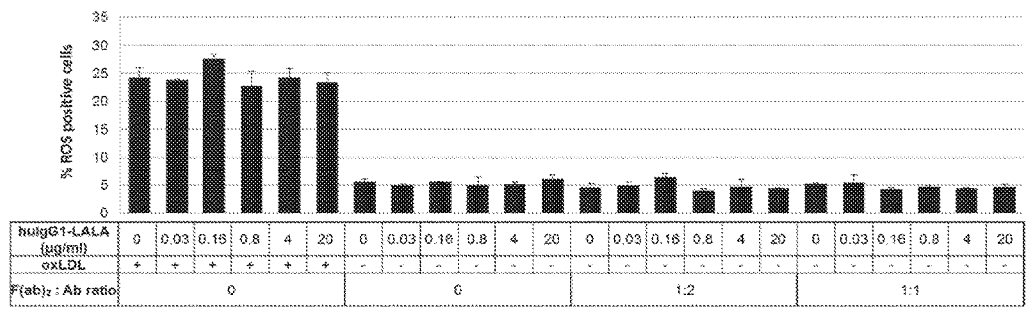

Cells expressing human LOX-1 (huLOX1/HEK293) were dissociated using TrypLE Express (Invitrogen catalof number 12605-010) and washed once with PBS. The cells were then resuspended at $2\times10^6$ cells/mL in assay medium (DMEM+10% FBS) and seeded at 50 μl/well ($1\times10^6$ cells/well) into a 96-well V-bottom plate (Costar catalog number 3894). 50 μl/well of LOX-1 (or control) antibody solution with or without cross-linking Fab (prepared as described above) was added and the mixture was incubated for 15 min at 37° C. OxLDL (0.1 mL/well in assay buffer, "High oxLDL" from Kalen, catalog number 770252-7) was added to a final concentration of 25 μg/mL, and the resulting mixture was incubated for 100 min at 37'C. H2DCFDA was diluted in assay medium and 0.1 mL/well added to a final concentration of 5-10 μM, and the mixture incubated for 15 min at 37° C. The cells were then washed once with 200 μl/well of HBSS containing calcium and magnesium, once with 200 μl/well of cold FACS buffer (2% FBS in PBS), and the cells were resuspended in 50-100 μL/well of cold FACS buffer. The fluorescence generated as a result of H2DCFDA oxidation was measured using a flow cytometer (excitation: 488 nm, emission: 500/530 nm). Exemplary results are shown in FIGS. 3 and 4, and Table 4.

TABLE 4

LOX-1 antibodies inhibit oxLDL induced reactive oxygen species (ROS) production in human LOX-1 transfected HEK293 cells (table with IC50 values), with no evidence for LOX-1 agonist activity (antibody alone or antibody + cross-linking $Fab_2$)

| | FF1 | FF3 | FF4 | FF5 | FF6 | E2E10 (murine parental) |
|---|---|---|---|---|---|---|
| Reactive oxygen species (ROS) generation in huLOX-1/HEK293 cells ($IC_{50}$, nM) | 6.0 | 7.4 | 5.3 | 4.8 | 7.9 | 5.7 |

TABLE 4-continued

LOX-1 antibodies inhibit oxLDL induced reactive oxygen species (ROS) production in human LOX-1 transfected HEK293 cells (table with IC50 values), with no evidence for LOX-1 agonist activity (antibody alone or antibody + cross-linking $Fab_2$)

| | FF1 | FF3 | FF4 | FF5 | FF6 | E2E10 (murine parental) |
|---|---|---|---|---|---|---|
| LOX-1 agonism? | No | No | No | No | No | No |
| LOX-1 agonism (antibody + anti-human Fab2 at 1:2 Fab2 to antibody molar ratio) | No | No | No | No | No | No |
| LOX-1 agonism (antibody + anti-human Fab2 at 1:1 Fab2 to antibody molar ratio) | No | No | No | No | No | No |

As seen in FIGS. 4A-4F, LOX-1 antibodies inhibit oxLDL induced reactive oxygen species (ROS) production in human LOX-1 transfected HEK293 cells. In the absence of oxLDL, LOX-1 antibodies (antibodies alone or in the presence of a cross-linking $Fab_2$) do not induce ROS production. An isotype control antibody has no effect on oxLDL induced ROS production in human LOX-1 transfected HEK293 cells.

Example 10: LOX-1 Antibodies Bind to Native LOX-1 Primary Human Neutrophils

LOX-1 antibodies were biotinylated using a kit from Thermo Scientific (EZ-Link Micro NHS-PEO4-Biotinylation Kit; Thermo Scientific catalog number 21955). Antibodies in PBS buffer at 0.5-1.0 mg/mL concentration were incubated with a 50-fold molar excess of NHS-biotin reagent at room temperature for 60 min. The biotinylated antibody was then separated from excess biotinylation reagent using a desalting spin column equilibrated in PBS and used according to the manufacturer's instructions (Zeba Desalt Spin Column 7K MWCO, Thermo Scientific catalog number 89882). The concentration of the biotinylated antibody was determined based on measurement of the absorbance at 280 nm.

Neutrophils were isolated from blood samples obtained from healthy donors using standard methods. Briefly, human whole blood was collected in a vial containing EDTA. To 10 mL of the blood sample, 10 mL of Sedimentation Buffer (3% dextran, 0.9% sodium chloride) was added, and the resulting solution was gently mixed and allowed to stand at room temperature for 20 minutes. The top layer comprising leukocyte-rich plasma was centrifuged at 1200 rpm (250-500×g) for 10 minutes at 4° C. The supernatant was discarded, and the cell pellet immediately resuspended in 10 mL of 0.9% sodium chloride at room temperature. The resulting cell suspension was carefully transferred to a 50 mL conical tube containing 10 mL Ficoll-Paque, layering the cell suspension on top of the Ficoll-Paque, and the tube was then centrifuged at 1400 rpm (400×g) for 30 minutes at room temperature. The top layer was the discarded. To the resulting cell pellet, 10 mL 0.2% ice-cold sodium chloride was added, and the mixture was incubated for exactly 30 seconds to lyse red blood cells; 10 mL of ice-cold 1.6% sodium chloride was added to restore isotonicity. The cell suspension was then centrifuged at 1200 rpm (250-500 rpm) for 5 minutes. The supernatant was then discarded, and the red blood cell lysis procedure repeated once more. The resulting cell pellet was resuspended in FACS buffer (2 mM EDTA, 1% BSA, and 0.2% sodium azide in PBS) at a cell density of $2\times10^6$ cells/mL.

Figure 5:
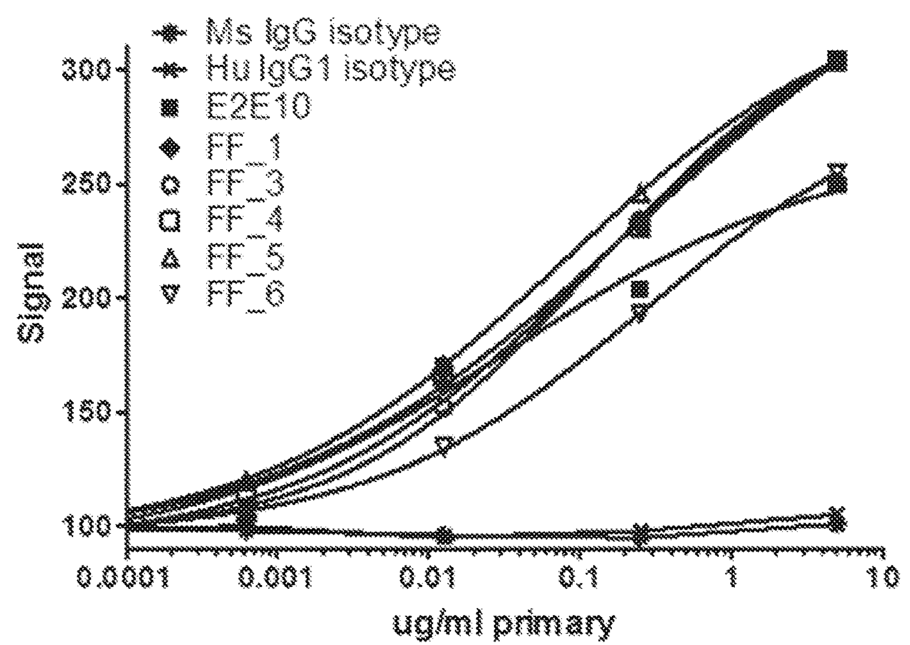
FIG. 5 depicts OX-1 antibodies binding to LOX-1 on the surface of human neutrophils.

The cell suspension containing freshly isolated human neutrophils was transferred (50 ul/well) to wells of a 96-well V-bottom plate ($1\times10^5$ cells/well) (Costar, catalog number 3894). Blocking buffer (4% normal rabbit serum diluted in FACS buffer (2 mM EDTA, 1% BSA, and 0.2% sodium azide in PBS) (50 ul/well) was added and the plate was incubated on ice for 30 minutes. Biotinylated LOX-1 antibody (10 μl) in FACS buffer was then added to the wells at final concentrations ranging from 1 ng/ml to 5 ug/mL, and the plate was incubated on ice for 30 minutes. The plate was then centrifuged at 1200 rpm (250-300×g) for 3 minutes and supernatant was discarded. The cells were then washed twice with 0.2 mL FACS buffer, and then 0.1 mL of PE-streptavidin (BD Pharmingen catalog number 554061) diluted at 1:250 in FACS buffer was added, and the plate incubated on ice for 30 minutes. The plate was then centrifuged again, supernatant discarded, and the cells washed twice with 0.2 mL FACS buffer. Cells were then resuspended in 0.1 mL of fixing buffer (FACS buffer with 2% paraformaldehyde) and analyzed using a FACS instrument. To determine an EC50 value for neutrophil binding by LOX-1 antibodies, the LOX-1 staining intensity determined by FACS was plotted vs. the concentration of the antibody as shown in FIG. 5 and Table 3.

Example 11: Epitope Mapping by Hydrogen/Deuterium Exchange Mass Spectrometry

Hydrogen-deuterium exchange (HDx) in combination with mass spectrometry (MS) (Woods, 2001) was used to map the binding site of antibody E2E10 on LOX-1. In HDx, exchangeable amide hydrogens of proteins are replaced by deuterium. This process is sensitive to protein structure/dynamics and solvent accessibility and, therefore, able to report on ligand binding. The non-invasive nature of HDxMS, high sensitivity, ability to work with large proteins, and the high resolution with which binding sites can be mapped sets it apart from other methods. The goal of these experiments was the identification of the epitope of E2E10 on LOX1.

Automated HDx/MS experiments were performed using methods similar to those described in the literature (Chalmers, 2006). A LEAP Technologies Pal HTS liquid-handler (LEAP Technologies, Carrboro, N.C.) was used for all liquid handling operations. The liquid-handler was controlled by automation scripts written in LEAP Shell and was housed in a refrigerated enclosure maintained at 2° C. A 6-port injection valve and a wash station were mounted on the liquid-handler rail and facilitated sample injection into the chromatographic system and syringe washing. For on-line digestion, an enzyme column (Poroszyme immobilized pepsin, 20×2.1×30 mm, ABI, Foster City, Calif.) was placed in line between the injection valve and a trapping cartridge. The chromatographic system, consisting of two additional valves (15 kPSI Valco, Houston, Tex.), a 4 μL EXP Halo C18 reversed-phase trap cartridge (Optimize Technologies Inc., Oregon City, Oreg.), and an analytical column (300 μm ID, Halo 2.7 μm 018, Michrom Bioresources Inc.), was housed in a separate cooled enclosure that was mounted in front of the source of the LTQ-Orbitrap mass spectrometer (Thermo Scientific, San Jose, Calif.). The temperature of the enclosure housing the chromatographic system was maintained at 0° C. by peltier coolers.

For non-deuterated and deuterated controls, 10 μL of human soluble LOX-1 solution (0.73 mg/mL) was diluted with 15 μL of 50 mM triethanolamine buffer (pH 7.8). Complexes were prepared by mixing 10 μL of LOX-1 solution (0.73 mg/mL) with an equimolar amount of E2E10 and the appropriate amount of 50 mM triethanolamine buffer (pH 7.8) to bring the total volume to 25 μL. After forming complexes, the solutions were allowed to incubate for 30 min. To initiate the exchange reaction, 75 μL of $D_2O$ buffer ($D_2O$ in 150 mM NaCl, Cambridge Isotopes Laboratories) was added and allowed to exchange for 10 min. The pH of the mixture was then lowered with the addition of 0.25 mL of reduction buffer (8 M Urea, 2 M Thiourea, 0.25 M TCEP, pH 2.5) to reduce disulfide bonds and slow down the exchange rate, effectively freezing the exchange state of the sample. After 10 min. of reduction, the mixture was diluted with 0.5 mL of quench buffer (50 mM Glycine, pH 2.5). Next, 0.5 mL of the sample was injected through an inline digestion column onto a trap, and analyzed by LC-MS as described below.

The chromatography system uses two separate HPLC pumps to perform in-line digestion, trap the digested peptides onto a C18 trap column, and elute trapped peptides through an analytical column into the mass spectrometer. The "loading" pump (Surveyor MS pump, Thermo Scientific, San Jose, Calif.), operated at a flow rate of 125 μL/min (0.05% TFA), transferred samples from the PAL injection valve sample loop (500 μL), through the pepsin column, and into the reversed-phase trap cartridge. After a 6 min. loading step, a "load" valve was switched to allow buffer (0.25% formic acid) from the "gradient" pump (Nano Acquity, Waters Corp., Milford, Mass.) to flow through the trap at a flow rate of 20 μL/min for a 3 min. desalting period. After the desalting step, a "desalt" valve was switched to facilitate elution of peptides from the trap and onto the analytical column and into the ion source of the mass spectrometer. The gradient pump delivered a gradient of 0 to 40% B over 20 min. followed by 40% to 75% B over 5 min. The total time for the gradient was 30 min. The gradient pump buffer compositions were A: 99.75:0.25% v/v ($H_2O$:formic acid) and B: 99.75:0.25% v/v (acetonitrile:formic acid).

Proteolytic peptides were sequenced by tandem mass spectrometry (MS/MS). The same method was used for the acquisition of non-deuterated LOX-1, deuterated LOX-1, and all of the deuterated complex samples even though only MS2 data from the non-deuterated LOX1 run were used for peptide identification. For these acquisitions, MS/MS were acquired in the LTQ and MS scans were acquired in the Orbitrap. Acquisitions in the Orbitrap were acquired at a resolution of 60,000 over the m/z range of 400-2000. The instrument parameters used for all experiments included a spray voltage of 3.5 kV, a maximum injection time of 1000 ms, LTQ AGC target for MS of 50,000 ions and an FTMS AGC target for MS of 1,000,000 ions. To initiate data processing, Orbitrap .RAW files were converted into .mzXML files (Pedrioli 2004) using an in-house program (RawXtract). Subsequently, .mzXML files were converted into .mzBIN files and tandem MS acquisitions were searched using SEQUEST (ThermoElectron). SEQUEST results were filtered using DTASelect (Tabb 2002). Using the peptide sequence identifications, an in-house written program (Deutoronomy) was used to automatically extract chromatograms for each identified sequence ion and generate average spectra over a specified m/z range and retention time window. Average spectra were then smoothed and centroided to determine the average deuterium incorporation. After the initial automated processing, the quality and centroiding of each average spectrum was manually validated or corrected using an interactive data viewer built into Deutoronomy.

The HDxMS mapping experiment identified three regions of LOX1 that were significantly protected. Major protection was observed for the peptide $F_{228}RVRGAVSQTYPSGTCAYI_{246}$ (SEQ ID NO.:3). Minor protection of the peptides $N_{100}ELKEMIETL_{109}$ and $S_{207}RRNPSYPWLWE_{218}$ was also observed (SEQ ID NO.: 4 and 5, respectively). The protected regions were mapped onto a the crystal structure of human soluble LOX-1 C-terminal lectin-like domain (CTLD) obtained from the protein data bank (1YPQ). One of the protected regions, $N_{100}ELKEMIETL_{109}$ (SEQ ID NO.: 4), is not present in the LOX-1 CTLD crystal structure. The peptide $F_{228}RVRGAVSQTYPSGTCAYI_{246}$ (SEQ ID NO.: 3) maps to the face of the LOX-1 molecule implicated in ligand binding by published site directed mutagenesis studies (Ohki et al. (2005) *Structure,* 13: 905-917). The results therefore indicate that E2E10 likely acts as a competitive inhibitor of LOX-1 ligand binding to LOX-1. Since the humaneering process used to convert E2E10 to the humanized variants FF1, FF3, FF4, FF5, and FF6 is very unlikely to change the epitope specificity of the antibody (see Example 6), these results also identify the primary binding site of FF1, FF3, FF4, FF5, and FF6 on LOX-1.

Change in deuterium incorporation of LOX-1 derived peptides due to E2E10 binding to LOX-1 is shown in Table 5.

TABLE 5

| LOX-1 Epitope | SEQ ID NO: | Change in deuterium incorporation |
|---|---|---|
| EFRHGLNDIF | 124 | 0 |
| EFRHGLNDIFE | 125 | 0 |
| EAQKIEWHESQVSDL | 126 | 0 |
| AQKIEWHESQVSDL | 127 | 0 |
| LTQEQANLTHQKKKLEGQISARQQAEEASQESENELKE | 128 | 0 |
| LTQEQANLTHQKKKLEGQISARQQAEEASQESENELKEMIETL | 129 | -2 |
| ASQESENELKEMIETL | 130 | -1 |
| NELKEMIETL | 131 | -2 |
| FSSGSFNWEKSQEKC | 132 | 0 |
| FSSGSFNWEKSQEKCLSL | 133 | 0 |
| IQQAISY | 134 | 0 |
| SRRNPSYPWLWEDGSPLMPHL | 135 | -1 |
| WEDGSPLMPHL | 136 | 0 |
| FRVRGAVSQTYPSGTCAYIQRGAVYAENCILAAFSICQKKANLRAQ | 137 | -9 |

TABLE 5-continued

| LOX-1 Epitope | SEQ ID NO: | Change in deuterium incorporation |
|---|---|---|
| YIQRGAVYAEN | 138 | 0 |
| IQRGAVYAEN | 139 | 0 |
| AAFSICQKKANL | 140 | 0 |
| AAFSICQKKANLRAQ | 141 | 0 |
| FSICQKKANL | 142 | 0 |
| FSICKKANLRAQ | 143 | 0 |

Example 12: Preparation of Purified Recombinant Cynomolgus Monkey Soluble LOX-1 for Use in LOX-1 Antibody Binding Assays To determine the nucleotide and amino acid sequences of cynomolgus monkey LOX-1, total RNAs were extracted from organs obtained from 3 individual monkeys: 3 organs from one individual from Zyagen/GW, and 12 organs from 2 individuals from Covance, Inc. The total RNAs were then used for PCR amplification, using primers from the untranslated region which were designed according to public databases (Uniprot, NCBI). Standard sequencing methods were used to determine the nucleic acid sequences of the amplified LOX-1 mRNAs. Within the extracellular domain of cynomolgus monkey LOX-1 (corresponding to amino acids 61-273), the cynomolgus LOX-1 amino acid sequences derived from the 3 individual monkeys were identical.

A nucleic acid sequence encoding the extracellular domain (amino acid residues 61-273) of cynomolgus monkey LOX-1 polypeptide with N-terminal signal peptide from human CD33, purification tag (EFHR), and BirA biotinylation sequence (GLNDIFEAQKIEWHE) (SEQ ID NO 144) was subcloned into the mammalian cell expression vector pRS5a. Expression and purification of cynomolgus monkey soluble LOX-1 was carried out using the same methods described for human soluble LOX-1 in Example 1. The amino acid sequence of mature APP-Avi-soluble cynomolgus monkey LOX-1(61-273) is shown in Table 6. For some experiments, cynomolgus monkey soluble LOX-1 protein was biotinylated using the same method described for human soluble LOX-1 in Example 5.

TABLE 6

| SEQ ID 6: Amino Acid Sequence of mature APP-Avi-soluble cynomolgus monkey LOX-1 (61-273) (APP and Avi tags underlined) |
|---|
| <u>EFRHGLNDIFEAQKIEWHE</u>SQVSNLLKQQQTNLTHQKNKLEGQISARQQA EEASQESQNELKEMIETLAWKLNEKSKEQMELHHQNLNLQETLKRVANCS APCPQDWIWHEENCYLFSTGSFNWEKSQEKCLSLDAKLLKINSTADLDFI QQAISYSSFPFWMGLSRRNPSYPWLWEDGSPLMPHLFRIRGAVSQTYPSG TCAYIQRGAVYAENCILAAFSICQKKANLRAQ |

Example 12

Antibody Dissociation Constant Determination by BIACORE™ Binding Assay

For murine LOX-1 antibody E2E10 binding to human and cynomolgus monkey LOX-1, a BIACORE™ T200 was primed with fresh, filtered running buffer (lx HBS-EP+(GE catalog number BR-1006-60)). A CM5 chip (GE catalog number BR-1005-30) was prepared using a mouse antibody capture kit (GE catalog number BR-1008-38) and an amine coupling kit (GE catalog number BR-1000-50). Briefly, a new chip was activated with EDC/NHS at 10 ul/min for 420 sec. Anti-mouse IgG antibody was immobilized at 30 ug/ml in 10 mM acetate pH 5.0 at 10 ul/min for 420 sec. The chip surface was deactivated with 1M ethanolamine solution (10 ul/min for 420 sec) and then conditioned three times with 10 mM Glycine-HCl, pH 1.5 (GE catalog number BR-1003-54) at 60 ul/min for 30 sec.

A method run was programmed to measure kinetics of human or cynomolgus monkey soluble LOX-1 binding to anti-LOX-1 antibody. 5 startup cycles were run as follows: 1) running buffer for 30 sec at 60 ul/min, 2) Running buffer for 350 sec with 350 sec dissociation at 60 ul/min, extra wash with regeneration buffer (Glycine-HCl pH 1.5, 0.05% P20 (GE catalog number BR-1000-54)), 3) Regeneration buffer for 60s at 60 ul/min, 4) Regeneration buffer for 35s at 60 ul/min, extra wash with running buffer and including a carry-over control.

For sample cycles, 1) Ms-anti-Hu LOX-1 mAb was captured on flow cell 2, 3, or 4 for a pre-determined amount of time that allowed for capture of approximately 20RUs at 10 ul/min. Flow cell 1 was used as a reference, 2) running buffer for 30s at 60 ul/min, 3) human soluble LOX-1 or cynomolgus monkey soluble LOX-1 diluted in running buffer at various concentrations (with at least two duplicate samples and multiple buffer blanks for 350 sec at 60 ul/min, with either 750 sec or 3000 sec dissociation time), 4) regeneration buffer for 60 sec at 60 ul/min, 5) running buffer for 35s at 60 ul/min, extra wash with running buffer and including a carry-over control. Data were analyzed using buffer blanks, reference blank, and a 1:1 binding model for curve fitting in order to determine association and dissociation rate constants (ka and kd) and equilibrium binding constants (KD) (see results for E2E10 in Tables 7-8).

Surface plasmon resonance measurements quantifying the interaction of humanized LOX-1 antibodies with human or cynomolgus monkey LOX-1 were done with the optical biosensor BIAcore T200 on a CM5 chip. Goat-anti-hIgG (gamma) (Invitrogen H10500) was coated at 3,000 RU on the CM5 chip in acetate buffer, pH 4.0. The running buffer used was PBS, pH 7.4 (filtered, degassed). Test antibodies were loaded into individual flow cells at a concentration of 1 ug/mL at a flow rate of 10 uL/min. The target number of IgG capture was between 20-30 RU, in HBS-EP buffer (0.01M HEPES, pH 7.4, 0.15M NaCl, 3 mM EDTA, 0.05% P20). Human or cynomolgus monkey soluble LOX-1 was diluted to a concentration of 33 nM in HBS-EP buffer, then diluted serially (1:3) down to a concentration of 0.137 nM. This represents six different concentrations of human or cynomolgus monkey LOX-1. The antigen was introduced into individual flow cells at a flow rate of 30 uL/min. Parameters for association time were set at 700 seconds and dissociation time was set at 5,400 seconds. Data were analyzed using buffer blanks, reference blank, and a 1:1 binding model for curve fitting in order to determine association and dissociation rate constants (ka and kd) and equilibrium binding constants (KD) (see results for FF1, FF3, FF4, FF5, and FF6 in Tables 7-8).

TABLE 7

Dissociation Constants ($K_D$) of LOX-1 Antibodies Binding to Human Soluble LOX-1 Determined By Biacore Kinetic Binding Assays

| | FF1 | FF3 | FF4 | FF5 | FF6 | E2E10 (murine parental) |
|---|---|---|---|---|---|---|
| $k_a$ ($M^{-1}s^{-1}$) | $1.0 \times 10^6$ | $1.0 \times 10^6$ | $2.2 \times 10^6$ | $1.1 \times 10^5$ | $6.8 \times 10^6$ | $1.7 \times 10^6$ |
| $k_d$ ($s^{-1}$) | $1.9 \times 10^{-5}$ | $2.0 \times 10^{-6}$ | $5.2 \times 10^{-6}$ | $3.6 \times 10^{-5}$ | $2.3 \times 10^{-5}$ | $3.2 \times 10^{-5}$ |
| $K_D$, pM | 19 | 21 | 2 | 34 | 34 | 18 |

TABLE 8

Dissociation Constants ($K_D$) of LOX-1 Antibodies Binding to Cynomolgus Monkey Soluble LOX-1 Determined By Biacore Kinetic Binding Assays

| | FF1 | FF3 | FF4 | FF5 | FF6 | E2E10 (murine parental) |
|---|---|---|---|---|---|---|
| $k_a$ ($M^{-1}s^{-1}$) | $1.1 \times 10^6$ | $7.7 \times 10^5$ | $2.1 \times 10^6$ | $1.4 \times 10^6$ | $9.5 \times 10^5$ | $1.7 \times 10^6$ |
| $k_d$ ($s^{-1}$) | $1.3 \times 10^{-5}$ | $1.7 \times 10^{-5}$ | $2.6 \times 10^{-6}$ | $4.8 \times 10^{-5}$ | $5.0 \times 10^{-5}$ | $2.5 \times 10^{-5}$ |
| $K_D$, pM | 12 | 23 | 1 | 35 | 53 | 15 |

Example 13: Antibody Dissociation Constant Determination by Solution Equilibrium Titration (SET) Assay The following SET protocol was used to determine KD value for biotinylated E2E10 binding to human soluble LOX-1. A 96-well MSD plate (Standard Bind plate, MSD catalog number L15XA-3) was coated with 50 uL 0.25 ug/mL human soluble LOX-1 in PBS by overnight incubation at 4° C. The solution-phase samples were prepared by titration of human soluble LOX-1 in SET diluent (PBS, 0.5% BSA, 0.1% Tween-20, 0.1% Triton X-100) in a polypropylene V-bottom 96-well plate. This dilution series was combined 1:1 (100 μL total) with biotinylated E2E10 diluted in SET diluent, and the samples were incubated overnight at room temperature with shaking.

The coated MSD plate was washed three times with wash buffer (PBS, 0.05% Tween-20) using a plate washer and then inverted and blotted on a Kimwipe to remove residual liquid. The plate was then blocked with 200 uL/well SET blocking buffer (PBS, 2% BSA, 0.1% Tween-20, 0.1% Triton X-100) and incubated for 1 hr with gentle shaking. The plate was washed once. 25 μL/well of the solution-phase equilibrium binding sample was added to the plate, in duplicate, and incubated for 30 min with shaking. The plate was washed three times. 25 μL/well Streptavidin SULFO-TAG (MSD catalog number R32AD-1) diluted 1:500 in SET diluent was added to the plate and incubated for 1 hr with gentle shaking. The plate was washed three times, 100 μL Read Buffer T (MSD catalog number R92TC-1) was added to the plate and read on an MSD SECTOR Imager 6000. The KD values were determined by fitting the data to the following equation:

$$Y=(B\max/(CAb/2))*((CAb/2)-((((((CAg+CAb)+KD)/2)-((((((CAg+CAb)+KD)\hat{}2)/4)-(CAg*CAb))\hat{}0.5))\hat{}2)/(2*CAb))).$$

where Bmax is the signal when no LOX-1 protein is present in solution, CAb is the constant concentration of LOX-1 antibody in solution, CAg is the concentration of soluble LOX-1 in solution, and KD is the equilibrium binding constant.

For humanized LOX-1 antibodies FF1, FF3, FF4, FF5, and FF6, the following solution equilibrium titration (SET) assay protocol was used to determine $K_D$ values. The assays were performed in a 96-well polypropylene plate (Thermo Scientific, Catalog no. AB-1127) as follows. A constant concentration of LOX-1 antibody (1 pM) was mixed with different concentrations of non-biotinylated human or cynomolgus monkey LOX-1 protein (3-fold serial dilution ranging from 1 nM to 0.017 pM) in SET buffer (PBS, pH 7.4 without $CaCl_2$ or $MgCl_2$, Gibco, catalog no. P7949; 0.5% w/v bovine serum albumin, fatty acid free, Calbiochem, catalog no. 26575; and 0.02% v/v Tween-20, Sigma, catalog no. P7949). The final reaction volume was 80 mL. The plate was sealed using an adhesive film (WVR, catalog no. 60941-062) and incubated at 22° C. for 14 hours with constant shaking (300 rpm).

Figure 6A:
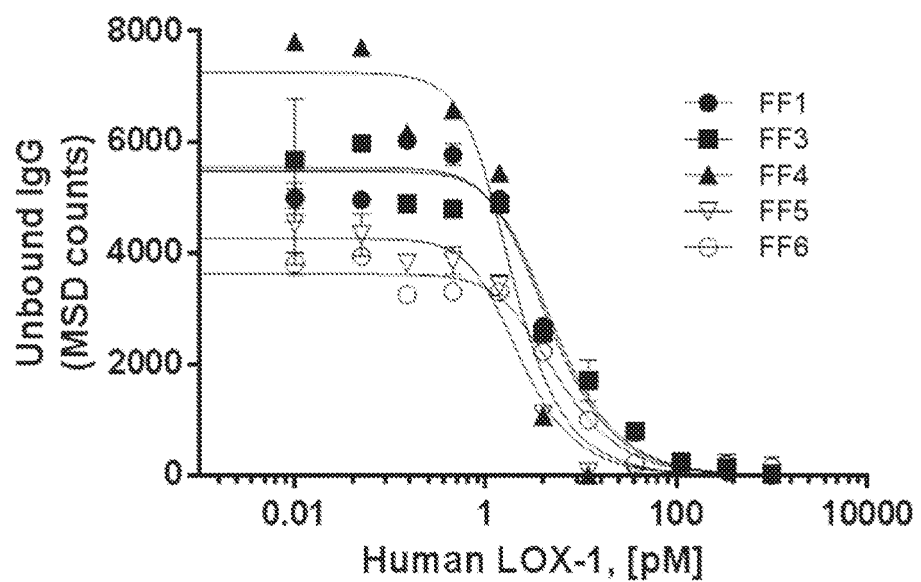
FIGS. 6A-6B depict antibody dissociation constant ($K_D$) determination by solution equilibrium titration (SET) assays with human or cynomolgus monkey APP-Avi-LOX-1 proteins.
Figure 6B:
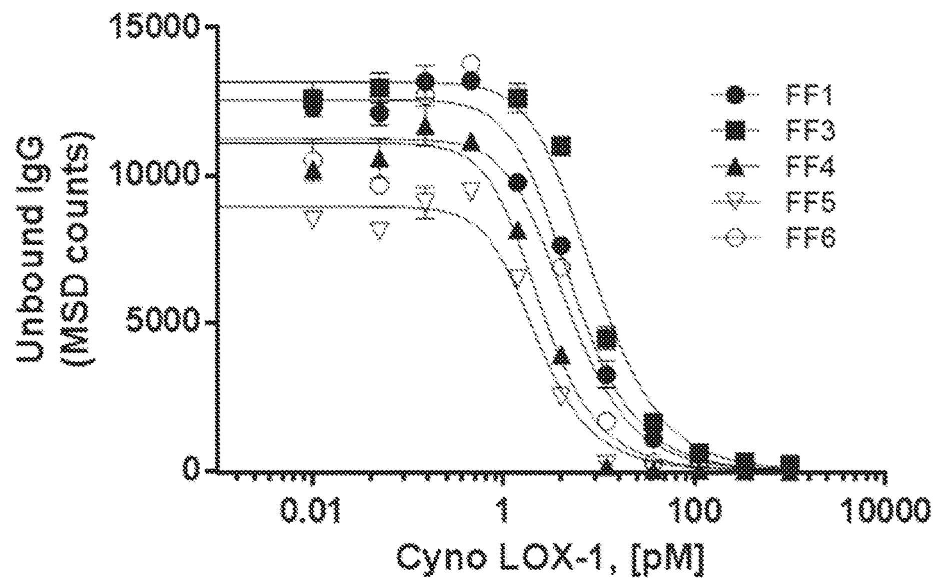

During the same period, a 384-well streptavidin-coated MSD plate (Meso Scale Discovery, catalog no. L21SA) was blocked by incubating the plate with 50 μL blocking buffer (PBS, pH 7.4, 5% w/v bovine serum albumuin) per well overnight at 4° C. The blocked MSD plate was then washed 3 times with wash buffer (PBS, pH 7.4 and 0.05% v/v Tween-20) using a plate washer (BioTek). Following washing, biotinylated human or cynomolgus monkey soluble LOX-1 protein (25 pM, 15 μL per well) was immobilized on the surface by incubation at 22° C. for one hour with constant shaking (600 rpm). The plate was then washed 3 times as described earlier. In some experiments, non-biotinylated soluble human LOX-1 protein was used (R&D systems, catalog no. 1798-LX-050) was used; in this case the LOX-1 protein was immobilized by overnight incubation at 1 nM concentration in a standard MSD plate (MSD, catalog no. L21XA). The equilibrium binding reactions (15 μL per well) were then applied to the MSD plate with immobilized LOX-1 and incubated for 30 min. The unbound material was removed by washing the plate, and the captured antibody was detected by adding 15 μL per well of a 1:500 dilution of Sulfa-tagged goat anti-human IgG (Mesa Scale Discovery, catalog no. R3AJ-1). The plate was then incubated for one hour with constant shaking (600 rpm). The plate was washed 3 times, and then 15 of 1×MSD read buffer T (Meso Scale Discovery, catalog no. R92TC-2) was added and the plate was developed using a Sector Imager 6000 (Mesa Scale Discovery). The data were transferred to Excel for analysis and plotted using GraphPad Prism v5. The $K_D$ values were determined by fitting the data to the following equation:

$$Y=(B\max/(CAb/2))*((CAb/2)-((((((CAg+CAb)+KD)/2)-((((((CAg+CAb)+KD)^2)/4)-(CAg*CAb))^0.5))^2)/(2*CAb))).$$

where Bmax is the signal when no LOX-1 protein is present in solution, CAb is the constant concentration of LOX-1 antibody in solution, CAg is the concentration of soluble LOX-1 in solution, and KD is the equilibrium binding constant. Results for FF1, FF3, FF4, FF5, FF6 and E2E10 are shown in Table 9 and FIG. 6).

TABLE 9

LOX-1 Antibody Dissociation Constants ($K_D$) Determination By Solution Equilibrium Titration (SET) Assays

| Soluble LOX-1 | FF1 | FF3 | FF4 | FF5 | FF6 | E2E10 (mouse parental) |
|---|---|---|---|---|---|---|
| Human Soluble APP-Avi-LOX-1 ($K_D$, pM by SET) | 1.8 | 1.6 | 0.5 | 0.7 | 2.3 | 2 |
| Human Soluble $His_9$-LOX-1 from R&D Systems ($K_D$, pM by SET) | 3.1 | 2.3 | 0.7 | 0.8 | 2.0 | ND |

TABLE 9-continued

LOX-1 Antibody Dissociation Constants ($K_D$) Determination By Solution Equilibrium Titration (SET) Assays

| Soluble LOX-1 | FF1 | FF3 | FF4 | FF5 | FF6 | E2E10 (mouse parental) |
|---|---|---|---|---|---|---|
| Cynomolgus Monkey Soluble APP-Avi-LOX-1 ($K_D$, pM by SET) | 1.8 | 3.4 | 0.7 | 0.6 | 1.6 | ND |

INCORPORATION BY REFERENCE

All references cited herein, including patents, patent applications, papers, text books, and the like, and the references cited therein, to the extent that they are not already, are hereby incorporated herein by reference in their entirety.

EQUIVALENTS

The foregoing written specification is considered to be sufficient to enable one skilled in the art to practice the invention. The foregoing description and examples detail certain preferred embodiments of the invention and describe the best mode contemplated by the inventors. It will be appreciated, however, that no matter how detailed the foregoing may appear in text, the invention may be practiced in many ways and the invention should be construed in accordance with the appended claims and any equivalents thereof.

The invention claimed is:

1. A method of treating a a subject afflicted with a lectin-type oxidized low density lipoprotein receptor 1 (LOX-1)-disorder that is a cardiovascular disorder, the method comprising administering to the subject an effective amount of a pharmaceutical composition comprising an isolated antibody or antigen-binding fragment thereof that specifically binds to human LOX-1, wherein said antibody or fragment comprises a heavy chain variable region (VH) comprising complementarity determining regions HCDR1, HCDR2, and HCDR3, and a light chain variable region (VL) comprising complementarity determining regions LCDR1, LCDR2, and LCDR3, and wherein (i) the HCDR1 comprises the amino acid sequence of SEQ ID NO: 8, 28, 48, 68, or 88; the HCDR2 comprises the amino acid sequence of SEQ ID NO: 9, 29, 49, 69, or 89; the HCDR3 comprises the amino acid sequence of SEQ ID NO: 10, 30, 50, 70, or 90; the LCDR1 comprises the amino acid sequence of SEQ ID NO: 18, 38, 58, 78, or 98; the LCDR2 comprises the amino acid sequence of SEQ ID NO: 19, 39, 59, 79, or 99; and the LCDR3 comprises the amino acid sequence of SEQ ID NO: 20, 40, 60, 80, or 100; or (ii) the HCDR1 comprises the amino acid sequence of SEQ ID NO: 11, 31, 51, 71, or 91; the HCDR2 comprises the amino acid sequence of SEQ ID NO: 12, 32, 52, 72, or 92; the HCDR3 comprises the amino acid sequence of SEQ ID NO: 13, 33, 53, 73, or 93; the LCDR1 comprises the amino acid sequence of SEQ ID NO: 21, 41, 61, 81, or 101; the LCDR2 comprises the amino acid sequence of SEQ ID NO: 22, 42, 62, 82, or 102; and the LCDR3 comprises the amino acid sequence of SEQ ID NO: 23, 43, 63, 83, or 103.

2. The method of claim 1, wherein the subject is afflicted with one or more of intermittent claudication and Rutherford Class II/III Claudication.

3. The method of claim 1, wherein the subject is afflicted with angina.

4. The method of claim 1, wherein the subject is afflicted with atherosclerosis, arteriosclerosis, hypertension, myocardial infarction, vascular oxidative stress, myocardial ischemia, ischemia-reperfusion, diabetic nephropathy, cardiomyopathy, heart failure, peripheral artery disease (PAD), coronary heart disease, claudication, angina, coronary artery disease (CAD), stroke, or abnormal-endothelium-dependent vasodilation.

5. The method of claim 4, wherein the subject is administered another agent for the prevention, treatment, or improvement of the LOX-1-disorder.

6. The method of claim 5, wherein the another agent is a statin.

7. The method of claim 4, wherein (i) the HCDR1 comprises the amino acid sequence of SEQ ID NO: 8, the HCDR2 comprises the amino acid sequence of SEQ ID NO: 9, the HCDR3 comprises the amino acid sequence of SEQ ID NO: 10, the LCDR1 comprises the amino acid sequence of SEQ ID NO: 18, the LCDR2 comprises the amino acid sequence of SEQ ID NO: 19, and the LCDR3 comprises the amino acid sequence of SEQ ID NO: 20; or (ii) the HCDR1 comprises the amino acid sequence of SEQ ID NO: 11, the HCDR2 comprises the amino acid sequence of SEQ ID NO: 12, the HCDR3 comprises the amino acid sequence of SEQ ID NO: 13, the LCDR1 comprises the amino acid sequence of SEQ ID NO: 21, the LCDR2 comprises the amino acid sequence of SEQ ID NO: 22, and the LCDR3 comprises the amino acid sequence of SEQ ID NO: 23.

8. The method of claim 4, wherein:

(i) the HCDR1 comprises the amino acid sequence of SEQ ID NO: 8, the HCDR2 comprises the amino acid sequence of SEQ ID NO: 9, and the HCDR3 comprises the amino acid sequence of SEQ ID NO: 10; the LCDR1 comprises the amino acid sequence of SEQ ID NO: 18, the LCDR2 comprises the amino acid sequence of SEQ ID NO: 19, and the LCDR3 comprises the amino acid sequence of SEQ ID NO: 20;

(ii) the HCDR1 comprises the amino acid sequence of SEQ ID NO: 28, the HCDR2 comprises the amino acid sequence of SEQ ID NO: 29, and the HCDR3 comprises the amino acid sequence of SEQ ID NO: 30; the LCDR1 comprises the amino acid sequence of SEQ ID NO: 38, the LCDR2 comprises the amino acid sequence of SEQ ID NO: 39, and LCDR3 comprises the amino acid sequence of SEQ ID NO: 40;

(iii) the HCDR1 comprises the amino acid sequence of SEQ ID NO: 48, the HCDR2 comprises the amino acid sequence of SEQ ID NO: 49, and the HCDR3 comprises the amino acid sequence of SEQ ID NO: 50; the LCDR1 comprises the amino acid sequence of SEQ ID NO: 58, the LCDR2 comprises the amino acid sequence of SEQ ID NO: 59, and the LCDR3 comprises the amino acid sequence of SEQ ID NO: 60;

(iv) the HCDR1 comprises the amino acid sequence of SEQ ID NO: 68, the HCDR2 comprises the amino acid sequence of SEQ ID NO: 69, and the HCDR3 comprises the amino acid sequence of SEQ ID NO: 70; the LCDR1 comprises the amino acid sequence of SEQ ID NO: 78, the LCDR2 comprises the amino acid sequence of SEQ ID NO: 79, and the LCDR3 comprises the amino acid sequence of SEQ ID NO: 80;

(v) the HCDR1 comprises the amino acid sequence of SEQ ID NO: 88, the HCDR2 comprises the amino acid sequence of SEQ ID NO: 89, and the HCDR3 comprises the amino acid sequence of SEQ ID NO: 90; the LCDR1 comprises the amino acid sequence of SEQ ID NO: 98, the LCDR2 comprises the amino acid sequence of SEQ ID NO: 99, and the LCDR3 comprises the amino acid sequence of SEQ ID NO: 100;

(vi) the HCDR1 comprises the amino acid sequence of SEQ ID NO: 108, the HCDR2 comprises the amino acid sequence of SEQ ID NO: 109, and the HCDR3 comprises the amino acid sequence of SEQ ID NO: 110; the LCDR1 comprises the amino acid sequence of SEQ ID NO: 116, the LCDR2 comprises the amino acid sequence of SEQ ID NO: 117, and the LCDR3 comprises the amino acid sequence of SEQ ID NO: 118;

(vii) the HCDR1 comprises the amino acid sequence of SEQ ID NO: 11, the HCDR2 comprises the amino acid sequence of SEQ ID NO: 12, and the HCDR3 comprises the amino acid sequence of SEQ ID NO: 13; the LCDR1 comprises the amino acid sequence of SEQ ID NO: 21, the LCDR2 comprises the amino acid sequence of SEQ ID NO: 22, and the LCDR3 comprises the amino acid sequence of SEQ ID NO: 23;

(viii) the HCDR1 comprises the amino acid sequence of SEQ ID NO: 31, the HCDR2 comprises the amino acid sequence of SEQ ID NO: 32, and the HCDR3 comprises the amino acid sequence of SEQ ID NO: 33; the LCDR1 comprises the amino acid sequence of SEQ ID NO: 41, the LCDR2 comprises the amino acid sequence of SEQ ID NO: 42, and the LCDR3 comprises the amino acid sequence of SEQ ID NO: 43;

(ix) the HCDR1 comprises the amino acid sequence of SEQ ID NO: 51, the HCDR2 comprises the amino acid sequence of SEQ ID NO: 52, and the HCDR3 comprises the amino acid sequence of SEQ ID NO: 53; the LCDR1 comprises the amino acid sequence of SEQ ID NO: 61, the LCDR2 comprises the amino acid sequence of SEQ ID NO: 62, and the LCDR3 comprises the amino acid sequence of SEQ ID NO: 63;

(x) the HCDR1 comprises the amino acid sequence of SEQ ID NO: 71, the HCDR2 comprises the amino acid sequence of SEQ ID NO: 72, and the HCDR3 comprises the amino acid sequence of SEQ ID NO: 73; the LCDR1 comprises the amino acid sequence of SEQ ID NO: 81, the LCDR2 comprises the amino acid sequence of SEQ ID NO: 82, and the LCDR3 comprises the amino acid sequence of SEQ ID NO: 83;

(xi) the HCDR1 comprises the amino acid sequence of SEQ ID NO: 91, the HCDR2 comprises the amino acid sequence of SEQ ID NO: 92, and the HCDR3 comprises the amino acid sequence of SEQ ID NO: 93; the LCDR1 comprises the amino acid sequence of SEQ ID NO: 101, the LCDR2 comprises the amino acid sequence of SEQ ID NO: 102, and the LCDR3 comprises the amino acid sequence of SEQ ID NO: 103; or (xii) the HCDR1 comprises the amino acid sequence of SEQ ID NO: 111, the HCDR2 comprises the amino acid sequence of SEQ ID NO: 112, and the HCDR3 comprises the amino acid sequence of SEQ ID NO: 113; the LCDR1 comprises the amino acid sequence of SEQ ID NO: 119, the LCDR2 comprises the amino acid sequence of SEQ ID NO: 120, and the LCDR3 comprises the amino acid sequence of SEQ ID NO: 121.

9. The method of claim 4, wherein:

(i) the VH comprises the amino acid sequence of SEQ ID NO: 14 and the VL comprises the amino acid sequence of SEQ ID NO: 24;

(ii) the VH comprises the amino acid sequence of SEQ ID NO: 34 and the VL comprises the amino acid sequence of SEQ ID NO: 44;

(iii) the VH comprises the amino acid sequence of SEQ ID NO: 54 and the VL comprises the amino acid sequence of SEQ ID NO: 64;

(iv) the VH comprises the amino acid sequence of SEQ ID NO: 74 and the VL comprises the amino acid sequence of SEQ ID NO: 84;

(v) the VH comprises the amino acid sequence of SEQ ID NO: 94 and the VL comprises the amino acid sequence of SEQ ID NO: 104; or (vi) the VH comprises the amino acid sequence of SEQ ID NO: 114 and the VL comprises the amino acid sequence of SEQ ID NO: 122.

10. The method of claim 4, wherein the antibody comprises a heavy chain and a light chain, wherein:

(i) the heavy chain comprises the amino acid sequence of SEQ ID NO: 16 and the light chain comprises the amino acid sequence of SEQ ID NO: 26;

(ii) the heavy chain comprises the amino acid sequence of SEQ ID NO: 36 and the light chain comprises the amino acid sequence of SEQ ID NO: 46;

(iii) the heavy chain comprises the amino acid sequence of SEQ ID NO: 56 and the light chain comprises the amino acid sequence of SEQ ID NO: 66;

(iv) the heavy chain comprises the amino acid sequence of SEQ ID NO: 76 and the light chain comprises the amino acid sequence of SEQ ID NO: 86; or (v) the heavy chain comprises the amino acid sequence of SEQ ID NO: 96 and the light chain comprises the amino acid sequence of SEQ ID NO: 106.

11. The method of claim 1, wherein the subject is afflicted with peripheral artery disease (PAD).

12. A method of preventing or treating a subject at risk of or afflicted with a LOX-1-disorder, the method comprising administering to the subject an effective amount of a pharmaceutical composition comprising an isolated antibody or antigen-binding fragment thereof that specifically binds to human LOX-1, wherein the LOX-1-disorder is atherosclerosis, arteriosclerosis, hypertension, myocardial infarction, vascular oxidative stress, myocardial ischemia, ischemia-reperfusion, diabetic nephropathy, cardiomyopathy, heart failure, peripheral artery disease (PAD), coronary heart disease, claudication, angina, coronary artery disease (CAD), stroke, or abnormal-endothelium-dependent vasodilation;

wherein said antibody or fragment comprises a heavy chain variable region (VH) comprising complementarity determining regions HCDR1, HCDR2, and HCDR3, and a light chain variable region (VL) comprising complementarity determining regions LCDR1, LCDR2, and LCDR3, and wherein (i) the HCDR1 comprises the amino acid sequence of SEQ ID NO: 8, 28, 48, 68, or 88; the HCDR2 comprises the amino acid sequence of SEQ ID NO: 9, 29, 49, 69, or 89; the HCDR3 comprises the amino acid sequence of SEQ ID NO: 10, 30, 50, 70, or 90; the LCDR1 comprises the amino acid sequence of SEQ ID NO: 18, 38, 58, 78, or 98; the LCDR2 comprises the amino acid sequence of SEQ ID NO: 19, 39, 59, 79, or 99; and the LCDR3 comprises the amino acid sequence of SEQ ID NO: 20, 40, 60, 80, or 100; or (ii) the HCDR1 comprises the amino acid sequence of SEQ ID NO: 11, 31, 51, 71, or 91; the HCDR2 comprises the amino acid sequence of SEQ ID NO: 12, 32, 52, 72, or 92; the HCDR3 comprises the amino acid sequence of SEQ ID NO: 13, 33, 53, 73, or 93; the LCDR1 comprises the amino acid sequence of SEQ ID NO: 21, 41, 61, 81, or 101; the LCDR2 comprises the amino acid sequence of SEQ ID NO: 22, 42, 62, 82, or 102; and the LCDR3 comprises the amino acid sequence of SEQ ID NO: 23, 43, 63, 83, or 103.

13. The method of claim 12, wherein the LOX-1-disorder is peripheral artery disease (PAD).

14. The method of claim 13, wherein (i) the HCDR1 comprises the amino acid sequence of SEQ ID NO: 8, the HCDR2 comprises the amino acid sequence of SEQ ID NO: 9, the HCDR3 comprises the amino acid sequence of SEQ ID NO: 10, the LCDR1 comprises the amino acid sequence of SEQ ID NO: 18, the LCDR2 comprises the amino acid sequence of SEQ ID NO: 19, and the LCDR3 comprises the amino acid sequence of SEQ ID NO: 20; or (ii) the HCDR1 comprises the amino acid sequence of SEQ ID NO: 11, the HCDR2 comprises the amino acid sequence of SEQ ID NO: 12, the HCDR3 comprises the amino acid sequence of SEQ ID NO: 13, the LCDR1 comprises the amino acid sequence of SEQ ID NO: 21, the LCDR2 comprises the amino acid sequence of SEQ ID NO: 22, and the LCDR3 comprises the amino acid sequence of SEQ ID NO: 23.

15. The method of claim 12, wherein the LOX-1-disorder is claudication.

16. The method of claim 15, wherein (i) the HCDR1 comprises the amino acid sequence of SEQ ID NO: 8, the HCDR2 comprises the amino acid sequence of SEQ ID NO: 9, the HCDR3 comprises the amino acid sequence of SEQ ID NO: 10, the LCDR1 comprises the amino acid sequence of SEQ ID NO: 18, the LCDR2 comprises the amino acid sequence of SEQ ID NO: 19, and the LCDR3 comprises the amino acid sequence of SEQ ID NO: 20; or (ii) the HCDR1 comprises the amino acid sequence of SEQ ID NO: 11, the HCDR2 comprises the amino acid sequence of SEQ ID NO: 12, the HCDR3 comprises the amino acid sequence of SEQ ID NO: 13, the LCDR1 comprises the amino acid sequence of SEQ ID NO: 21, the LCDR2 comprises the amino acid sequence of SEQ ID NO: 22, and the LCDR3 comprises the amino acid sequence of SEQ ID NO: 23.

17. The method of claim 12, wherein (i) the HCDR1 comprises the amino acid sequence of SEQ ID NO: 8, the HCDR2 comprises the amino acid sequence of SEQ ID NO: 9, the HCDR3 comprises the amino acid sequence of SEQ ID NO: 10, the LCDR1 comprises the amino acid sequence of SEQ ID NO: 18, the LCDR2 comprises the amino acid sequence of SEQ ID NO: 19, and the LCDR3 comprises the amino acid sequence of SEQ ID NO: 20; or (ii) the HCDR1 comprises the amino acid sequence of SEQ ID NO: 11, the HCDR2 comprises the amino acid sequence of SEQ ID NO: 12, the HCDR3 comprises the amino acid sequence of SEQ ID NO: 13, the LCDR1 comprises the amino acid sequence of SEQ ID NO: 21, the LCDR2 comprises the amino acid sequence of SEQ ID NO: 22, and the LCDR3 comprises the amino acid sequence of SEQ ID NO: 23.

18. The method of claim 12, wherein:

(i) the HCDR1 comprises the amino acid sequence of SEQ ID NO: 8, the HCDR2 comprises the amino acid sequence of SEQ ID NO: 9, and the HCDR3 comprises the amino acid sequence of SEQ ID NO: 10; the LCDR1 comprises the amino acid sequence of SEQ ID NO: 18, the LCDR2 comprises the amino acid sequence of SEQ ID NO: 19, and the LCDR3 comprises the amino acid sequence of SEQ ID NO: 20;

(ii) the HCDR1 comprises the amino acid sequence of SEQ ID NO: 28, the HCDR2 comprises the amino acid sequence of SEQ ID NO: 29, and the HCDR3 comprises the amino acid sequence of SEQ ID NO: 30; the LCDR1 comprises the amino acid sequence of SEQ ID NO: 38, the LCDR2 comprises the amino acid sequence of SEQ ID NO: 39, and LCDR3 comprises the amino acid sequence of SEQ ID NO: 40;

(iii) the HCDR1 comprises the amino acid sequence of SEQ ID NO: 48, the HCDR2 comprises the amino acid sequence of SEQ ID NO: 49, and the HCDR3 comprises the amino acid sequence of SEQ ID NO: 50; the LCDR1 comprises the amino acid sequence of SEQ ID NO: 58, the LCDR2 comprises the amino acid sequence of SEQ ID NO: 59, and the LCDR3 comprises the amino acid sequence of SEQ ID NO: 60;

(iv) the HCDR1 comprises the amino acid sequence of SEQ ID NO: 68, the HCDR2 comprises the amino acid sequence of SEQ ID NO: 69, and the HCDR3 comprises the amino acid sequence of SEQ ID NO: 70; the LCDR1 comprises the amino acid sequence of SEQ ID NO: 78, the LCDR2 comprises the amino acid sequence of SEQ ID NO: 79, and the LCDR3 comprises the amino acid sequence of SEQ ID NO: 80;

(v) the HCDR1 comprises the amino acid sequence of SEQ ID NO: 88, the HCDR2 comprises the amino acid sequence of SEQ ID NO: 89, and the HCDR3 comprises the amino acid sequence of SEQ ID NO: 90; the LCDR1 comprises the amino acid sequence of SEQ ID NO: 98, the LCDR2 comprises the amino acid sequence of SEQ ID NO: 99, and the LCDR3 comprises the amino acid sequence of SEQ ID NO: 100;

(vi) the HCDR1 comprises the amino acid sequence of SEQ ID NO: 108, the HCDR2 comprises the amino acid sequence of SEQ ID NO: 109, and the HCDR3 comprises the amino acid sequence of SEQ ID NO: 110; the LCDR1 comprises the amino acid sequence of SEQ ID NO: 116, the LCDR2 comprises the amino acid sequence of SEQ ID NO: 117, and the LCDR3 comprises the amino acid sequence of SEQ ID NO: 118;

(vii) the HCDR1 comprises the amino acid sequence of SEQ ID NO: 11, the HCDR2 comprises the amino acid sequence of SEQ ID NO: 12, and the HCDR3 comprises the amino acid sequence of SEQ ID NO: 13; the LCDR1 comprises the amino acid sequence of SEQ ID NO: 21, the LCDR2 comprises the amino acid sequence of SEQ ID NO: 22, and the LCDR3 comprises the amino acid sequence of SEQ ID NO: 23;

(viii) the HCDR1 comprises the amino acid sequence of SEQ ID NO: 31, the HCDR2 comprises the amino acid sequence of SEQ ID NO: 32, and the HCDR3 comprises the amino acid sequence of SEQ ID NO: 33; the LCDR1 comprises the amino acid sequence of SEQ ID NO: 41, the LCDR2 comprises the amino acid sequence of SEQ ID NO: 42, and the LCDR3 comprises the amino acid sequence of SEQ ID NO: 43;

(ix) the HCDR1 comprises the amino acid sequence of SEQ ID NO: 51, the HCDR2 comprises the amino acid sequence of SEQ ID NO: 52, and the HCDR3 comprises the amino acid sequence of SEQ ID NO: 53; the LCDR1 comprises the amino acid sequence of SEQ ID NO: 61, the LCDR2 comprises the amino acid sequence of SEQ ID NO: 62, and the LCDR3 comprises the amino acid sequence of SEQ ID NO: 63;

(x) the HCDR1 comprises the amino acid sequence of SEQ ID NO: 71, the HCDR2 comprises the amino acid sequence of SEQ ID NO: 72, and the HCDR3 comprises the amino acid sequence of SEQ ID NO: 73; the LCDR1 comprises the amino acid sequence of SEQ ID NO: 81, the LCDR2 comprises the amino acid sequence of SEQ ID NO: 82, and the LCDR3 comprises the amino acid sequence of SEQ ID NO: 83;

(xi) the HCDR1 comprises the amino acid sequence of SEQ ID NO: 91, the HCDR2 comprises the amino acid sequence of SEQ ID NO: 92, and the HCDR3 comprises the amino acid sequence of SEQ ID NO: 93; the LCDR1 comprises the amino acid sequence of SEQ ID NO: 101, the LCDR2 comprises the amino acid sequence of SEQ ID NO: 102, and the LCDR3 comprises the amino acid sequence of SEQ ID NO: 103; or (xii) the HCDR1 comprises the amino acid sequence of SEQ ID NO: 111, the HCDR2 comprises the amino acid sequence of SEQ ID NO: 112, and the HCDR3 comprises the amino acid sequence of SEQ ID NO: 113; the LCDR1 comprises the amino acid sequence of SEQ ID NO: 119, the LCDR2 comprises the amino acid sequence of SEQ ID NO: 120, and the LCDR3 comprises the amino acid sequence of SEQ ID NO: 121.

19. The method of claim 18, wherein the antibody or fragment thereof is a monoclonal antibody, human antibody, humanized antibody, single chain antibody, Fab fragment, Fv fragment, F(ab)2 fragment, or scFv fragment.

20. The method of claim 18, wherein the antibody or fragment thereof is an IgG1 isotype.

21. The method of claim 12, wherein:

(i) the VH comprises the amino acid sequence of SEQ ID NO: 14 and the VL comprises the amino acid sequence of SEQ ID NO: 24;

(ii) the VH comprises the amino acid sequence of SEQ ID NO: 34 and the VL comprises the amino acid sequence of SEQ ID NO: 44;

(iii) the VH comprises the amino acid sequence of SEQ ID NO: 54 and the VL comprises the amino acid sequence of SEQ ID NO: 64;

(iv) the VH comprises the amino acid sequence of SEQ ID NO: 74 and the VL comprises the amino acid sequence of SEQ ID NO: 84;

(v) the VH comprises the amino acid sequence of SEQ ID NO: 94 and the VL comprises the amino acid sequence of SEQ ID NO: 104; or (vi) the VH comprises the amino acid sequence of SEQ ID NO: 114 and the VL comprises the amino acid sequence of SEQ ID NO: 122.

22. The method of claim 12, wherein the antibody comprises a heavy chain and a light chain, wherein:

(i) the heavy chain comprises the amino acid sequence of SEQ ID NO: 16 and the light chain comprises the amino acid sequence of SEQ ID NO: 26;

(ii) the heavy chain comprises the amino acid sequence of SEQ ID NO: 36 and the light chain comprises the amino acid sequence of SEQ ID NO: 46;

(iii) the heavy chain comprises the amino acid sequence of SEQ ID NO: 56 and the light chain comprises the amino acid sequence of SEQ ID NO: 66;

(iv) the heavy chain comprises the amino acid sequence of SEQ ID NO: 76 and the light chain comprises the amino acid sequence of SEQ ID NO: 86; or (v) the heavy chain comprises the amino acid sequence of SEQ ID NO: 96 and the light chain comprises the amino acid sequence of SEQ ID NO: 106.

23. The method of claim 12, wherein the subject is a human subject.

24. The method of claim 12, wherein the pharmaceutical composition is administered subcutaneously.

25. The method of claim 12, wherein the pharmaceutical composition is administered intravenously.

26. The method of claim 12, wherein (i) the VH comprises an amino acid sequence having at least 90% sequence identity to the amino acid sequence of SEQ ID NO: 14 and the VL comprises an amino acid sequence having at least 90% sequence identity to the amino acid sequence of SEQ ID NO: 24;

(ii) the VH comprises an amino acid sequence having at least 90% sequence identity to the amino acid sequence of SEQ ID NO: 34 and the VL comprises an amino acid sequence having at least 90% sequence identity to the amino acid sequence of SEQ ID NO: 44;

(iii) the VH comprises an amino acid sequence having at least 90% sequence identity to the amino acid sequence of SEQ ID NO: 54 and the VL comprises an amino acid sequence having at least 90% sequence identity to the amino acid sequence of SEQ ID NO: 64;

(iv) the VH comprises an amino acid sequence having at least 90% sequence identity to the amino acid sequence of SEQ ID NO: 74 and the VL comprises an amino acid sequence having at least 90% sequence identity to the amino acid sequence of SEQ ID NO: 84;

(v) the VH comprises an amino acid sequence having at least 90% sequence identity to the amino acid sequence of SEQ ID NO: 94 and the VL comprises an amino acid sequence having at least 90% sequence identity to the amino acid sequence of SEQ ID NO: 104; or (vi) the VH comprises an amino acid sequence having at least 90% sequence identity to the amino acid sequence of SEQ ID NO: 114 and the VL comprises an amino acid sequence having at least 90% sequence identity to the amino acid sequence of SEQ ID NO: 122.

27. A method of preventing or treating a LOX-1-disorder comprising administering to a subject in need thereof an effective amount of a pharmaceutical composition comprising an isolated antibody or antigen-binding fragment thereof that specifically binds to human LOX-1, wherein the LOX-1-disorder is atherosclerosis, arteriosclerosis, hypertension, myocardial infarction, vascular oxidative stress, myocardial ischemia, ischemia-reperfusion, diabetic nephropathy, cardiomyopathy, heart failure, peripheral artery disease (PAD), coronary heart disease, claudication, angina, coronary artery disease (CAD), stroke, or abnormal-endothelium-dependent vasodilation; and wherein said antibody or fragment comprises VH comprising the amino acid sequence of SEQ ID NO: 14, and a VL comprising the amino acid sequence of SEQ ID NO: 24.

28. The method of claim 27, wherein said antibody or fragment comprises a heavy chain comprising the amino acid sequence of SEQ ID NO: 16 and a light chain comprising the amino acid sequence of SEQ ID NO: 26.

29. The method of claim 28, wherein the LOX-1-disorder is peripheral artery disease (PAD).

30. The method of claim 28, wherein the LOX-1-disorder is claudication.

31. The method of claim 30, wherein the LOX-1-disorder is intermittent claudication or Rutherford Class II/III claudication.

32. The method of claim 28, wherein the subject is administered another agent for the prevention, treatment, or improvement of the LOX-1-disorder.

33. The method of claim 32, wherein the another agent is a statin.

34. The method of claim 27, wherein the LOX-1-disorder is peripheral artery disease (PAD).

35. The method of claim 27, wherein the LOX-1-disorder is claudication.

36. The method of claim 35, wherein the LOX-1-disorder is intermittent claudication or Rutherford Class II/III claudication.

37. The method of claim 27, wherein the subject is administered another agent for the prevention, treatment, or improvement of the LOX-1-disorder.

38. The method of claim 37, wherein the another agent is a statin.

39. The method of claim 27, wherein the antibody or fragment thereof is a monoclonal antibody, human antibody, humanized antibody, single chain antibody, Fab fragment, Fv fragment, F(ab)2 fragment, or scFv fragment.

40. The method of claim 27, wherein the antibody or fragment thereof is an IgG1 isotype.

41. The method of claim 27, wherein the subject is a human subject.

* * * * *